United States Patent
Huber et al.

(10) Patent No.: US 9,775,037 B2
(45) Date of Patent: *Sep. 26, 2017

(54) INTRA-PREMISES CONTENT AND EQUIPMENT MANAGEMENT IN A FEMTOCELL NETWORK

(71) Applicant: AT&T Mobility II LLC, Atlanta, GA (US)

(72) Inventors: Kurt Donald Huber, Kennesaw, GA (US); William Gordon Mansfield, Sugar Hill, GA (US); Judson John Flynn, Decatur, GA (US)

(73) Assignee: AT&T MOBILITY II LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/235,099

(22) Filed: Aug. 11, 2016

(65) Prior Publication Data

US 2016/0353351 A1 Dec. 1, 2016

Related U.S. Application Data

(63) Continuation of application No. 14/286,414, filed on May 23, 2014, which is a continuation of application (Continued)

(51) Int. Cl.
*H04W 40/02* (2009.01)
*G06F 19/00* (2011.01)
(Continued)

(52) U.S. Cl.
CPC ........ *H04W 12/06* (2013.01); *G06F 19/3406* (2013.01); *G06Q 20/102* (2013.01);
(Continued)

(58) Field of Classification Search
CPC ............. G06Q 20/1235; G06Q 20/322; G06Q 20/3223; G06Q 20/387; G06Q 20/405;
(Continued)

(56) References Cited

U.S. PATENT DOCUMENTS 5,564,016 A 10/1996 Korenshtein
5,745,559 A 4/1998 Weir
(Continued)

FOREIGN PATENT DOCUMENTS

CN 1429005 A 7/2003
CN 101017554 8/2007
(Continued)

OTHER PUBLICATIONS

Office Action dated Dec. 23, 2016 for U.S. Appl. No. 15/179,970, 17 pages.
(Continued)

*Primary Examiner* — Donald Mills
*Assistant Examiner* — Henry Baron
(74) *Attorney, Agent, or Firm* — Amin, Turocy & Watson, LLP

(57) ABSTRACT

Traffic and signaling is routed between a set of networked femto access points (APs) and devices served there from, and content and equipment that is part of a network functionally coupled to the set of networked femto APs is managed. Networked equipment spans a network deployed within the coverage area spanned by the set of femto APs. A routing platform functionally couples the networked equipment and the femto AP to enable content manipulation amongst a mobile device and the equipment. Routing platform also affords remote control of the networked equipment. Delivery of advertisement and monetary incentive(s) can be provided through the routing platform to the equipment. Routing platform further provides security features
(Continued)

related to operation of specific equipment and wireless services supplied via the routing platform.

20 Claims, 37 Drawing Sheets

Related U.S. Application Data

No. 13/554,710, filed on Jul. 20, 2012, now Pat. No. 8,787,342, which is a continuation of application No. 12/465,580, filed on May 13, 2009, now Pat. No. 8,274,958.

(60) Provisional application No. 61/052,813, filed on May 13, 2008.

(51) Int. Cl.

| | |
|---|---|
| *H04L 29/06* | (2006.01) |
| *H04W 12/06* | (2009.01) |
| *H04W 12/08* | (2009.01) |
| *H04W 4/12* | (2009.01) |
| *H04W 48/04* | (2009.01) |
| *G06Q 20/12* | (2012.01) |
| *G06Q 20/32* | (2012.01) |
| *G06Q 20/38* | (2012.01) |
| *G06Q 20/40* | (2012.01) |
| *G06Q 30/02* | (2012.01) |
| *G06Q 30/06* | (2012.01) |
| *H04W 48/08* | (2009.01) |
| *H04W 48/20* | (2009.01) |
| *H04W 48/16* | (2009.01) |
| *H04W 4/02* | (2009.01) |
| *H04L 12/24* | (2006.01) |
| *H04W 8/22* | (2009.01) |
| *H04W 88/08* | (2009.01) |
| *H04W 8/20* | (2009.01) |
| *H04W 48/02* | (2009.01) |
| *H04W 64/00* | (2009.01) |
| *H04W 68/02* | (2009.01) |
| *H04L 5/00* | (2006.01) |
| *H04W 4/04* | (2009.01) |
| *H04B 1/3822* | (2015.01) |
| *G06Q 20/10* | (2012.01) |
| *H04M 15/00* | (2006.01) |
| *H04W 4/24* | (2009.01) |
| *H04W 4/14* | (2009.01) |
| *H04W 84/04* | (2009.01) |
| *G06F 3/0484* | (2013.01) |
| *H04W 88/02* | (2009.01) |
| *H04W 88/06* | (2009.01) |

(52) U.S. Cl.
CPC ......... *G06Q 20/1235* (2013.01); *G06Q 20/32* (2013.01); *G06Q 20/322* (2013.01); *G06Q 20/3223* (2013.01); *G06Q 20/387* (2013.01); *G06Q 20/405* (2013.01); *G06Q 30/02* (2013.01); *G06Q 30/0222* (2013.01); *G06Q 30/0261* (2013.01); *G06Q 30/0601* (2013.01); *H04B 1/3822* (2013.01); *H04L 5/0048* (2013.01); *H04L 41/0803* (2013.01); *H04L 63/04* (2013.01); *H04L 63/0853* (2013.01); *H04L 63/0876* (2013.01); *H04L 63/101* (2013.01); *H04L 63/102* (2013.01); *H04L 63/108* (2013.01); *H04M 15/73* (2013.01); *H04W 4/02* (2013.01); *H04W 4/023* (2013.01); *H04W 4/027* (2013.01); *H04W 4/046* (2013.01); *H04W 4/12* (2013.01); *H04W 4/14* (2013.01); *H04W 4/24* (2013.01); *H04W 8/20* (2013.01); *H04W 8/22* (2013.01); *H04W 12/08* (2013.01); *H04W 40/02* (2013.01); *H04W 48/02* (2013.01); *H04W 48/04* (2013.01); *H04W 48/08* (2013.01); *H04W 48/16* (2013.01); *H04W 48/20* (2013.01); *H04W 64/006* (2013.01); *H04W 68/02* (2013.01); *H04W 88/08* (2013.01); *G05B 2219/2614* (2013.01); *G06F 3/0484* (2013.01); *H04L 2209/80* (2013.01); *H04W 84/045* (2013.01); *H04W 88/02* (2013.01); *H04W 88/06* (2013.01)

(58) Field of Classification Search
CPC ............... G06Q 30/02; G06Q 30/0222; G06Q 30/0261; G06Q 30/0601; H04B 1/3822; H04L 63/101; H04L 63/108; H04W 12/08; H04W 48/202; H04W 48/16; H04W 4/02
See application file for complete search history.

(56) References Cited

U.S. PATENT DOCUMENTS

| | | |
|---|---|---|
| 5,864,764 A | 1/1999 | Thro et al. |
| 5,956,715 A | 9/1999 | Glasser et al. |
| 5,983,097 A | 11/1999 | Kakinuma et al. |
| 6,052,594 A | 4/2000 | Chuang et al. |
| 6,151,505 A | 11/2000 | Larkins |
| 6,208,659 B1 | 3/2001 | Govindarajan et al. |
| 6,219,786 B1 | 4/2001 | Cunningham et al. |
| 6,256,504 B1 | 7/2001 | Tell et al. |
| 6,266,537 B1 | 7/2001 | Kashitani et al. |
| 6,295,454 B1 | 9/2001 | Havinis et al. |
| 6,363,261 B1 | 3/2002 | Raghavan |
| 6,477,367 B1 | 11/2002 | Kim |
| 6,483,852 B1 | 11/2002 | Jacquet et al. |
| 6,484,096 B2 | 11/2002 | Wong |
| 6,512,478 B1 | 1/2003 | Chien |
| 6,681,099 B1 | 1/2004 | Keranen et al. |
| 6,710,651 B2 | 3/2004 | Forrester |
| 6,718,023 B1 | 4/2004 | Zolotov |
| 6,768,722 B1 | 7/2004 | Katseff et al. |
| 7,080,139 B1 | 7/2006 | Briggs et al. |
| 7,142,861 B2 | 11/2006 | Murai |
| 7,146,153 B2 | 12/2006 | Russell |
| 7,155,526 B2 | 12/2006 | Chaudhary et al. |
| 7,209,739 B1 | 4/2007 | Narayanabhatla |
| 7,218,912 B2 | 5/2007 | Erskine et al. |
| 7,277,410 B2 | 10/2007 | Horneman |
| 7,317,931 B2 | 1/2008 | Guo |
| 7,370,356 B1 | 5/2008 | Guo |
| 7,437,755 B2 | 10/2008 | Farino et al. |
| 7,493,390 B2 | 2/2009 | Bobde et al. |
| 7,496,383 B2 | 2/2009 | Kurata |
| 7,509,124 B2 | 3/2009 | O'Neil |
| 7,516,219 B2 | 4/2009 | Moghaddam et al. |
| 7,551,574 B1 | 6/2009 | Peden et al. |
| 7,558,251 B1 | 7/2009 | Huang et al. |
| 7,574,731 B2 | 8/2009 | Fascenda et al. |
| 7,613,444 B2 | 11/2009 | Lindqvist et al. |
| 7,614,078 B1 | 11/2009 | Stieglitz et al. |
| 7,623,857 B1 | 11/2009 | O'Neil |
| 7,633,910 B2 | 12/2009 | Zhun et al. |
| 7,751,826 B2 | 7/2010 | Gardner |
| 7,761,526 B2 | 7/2010 | Pounds et al. |
| 7,768,983 B2 | 8/2010 | Nylander et al. |
| 7,885,644 B2 | 2/2011 | Gallagher et al. |
| 7,929,537 B2 | 4/2011 | Vasudevan et al. |
| 7,929,970 B1 | 4/2011 | Gunasekara |
| 7,941,144 B2 | 5/2011 | Nylander et al. |
| 7,995,994 B2 | 8/2011 | Khetawat et al. |
| 8,041,335 B2 | 10/2011 | Khetawat et al. |

(56) References Cited

U.S. PATENT DOCUMENTS

| | | | |
|---|---|---|---|
| 8,064,909 B2* | 11/2011 | Spinelli | H04W 36/36 |
| | | | 455/436 |
| 8,103,285 B2 | 1/2012 | Kalhan et al. | |
| 8,108,923 B1 | 1/2012 | Satish et al. | |
| 8,265,685 B2 | 9/2012 | Vikberg et al. | |
| 8,437,745 B2 | 5/2013 | Theppasaandra et al. | |
| 8,509,778 B2 | 8/2013 | Buchmayer et al. | |
| 8,510,801 B2 | 8/2013 | Majumdar et al. | |
| 8,522,312 B2 | 8/2013 | Huber et al. | |
| 8,743,776 B2 | 6/2014 | Gurajala et al. | |
| 8,774,155 B2 | 7/2014 | Passarella et al. | |
| 8,856,878 B2 | 10/2014 | Wohlert | |
| 2001/0021884 A1 | 9/2001 | Shinyagaito | |
| 2001/0029425 A1 | 10/2001 | Myr | |
| 2002/0044639 A1 | 4/2002 | Shioda et al. | |
| 2002/0077115 A1 | 6/2002 | Ruutu et al. | |
| 2002/0098837 A1 | 7/2002 | Ferrario et al. | |
| 2002/0107018 A1 | 8/2002 | Nakamura et al. | |
| 2002/0120723 A1 | 8/2002 | Forth et al. | |
| 2002/0123365 A1 | 9/2002 | Thorson | |
| 2002/0142791 A1 | 10/2002 | Chen et al. | |
| 2002/0159545 A1 | 10/2002 | Ramesh et al. | |
| 2002/0169986 A1 | 11/2002 | Lortz | |
| 2002/0196187 A1 | 12/2002 | Holt | |
| 2003/0028621 A1 | 2/2003 | Furlong et al. | |
| 2003/0101254 A1 | 5/2003 | Sato | |
| 2003/0109271 A1 | 6/2003 | Lewis et al. | |
| 2003/0125042 A1 | 7/2003 | Olrik et al. | |
| 2003/0125044 A1 | 7/2003 | Deloach | |
| 2003/0125048 A1 | 7/2003 | Lockhart et al. | |
| 2003/0133558 A1 | 7/2003 | Kung et al. | |
| 2003/0139180 A1 | 7/2003 | McIntosh et al. | |
| 2003/0142637 A1 | 7/2003 | Khawer et al. | |
| 2003/0144793 A1 | 7/2003 | Melaku et al. | |
| 2003/0153302 A1 | 8/2003 | Lewis et al. | |
| 2003/0185375 A1 | 10/2003 | Albal | |
| 2004/0003285 A1 | 1/2004 | Whelan | |
| 2004/0027278 A1 | 2/2004 | Park | |
| 2004/0111382 A1 | 6/2004 | Haji-Ioannou | |
| 2004/0125781 A1 | 7/2004 | Walter et al. | |
| 2004/0139201 A1 | 7/2004 | Chaudhary et al. | |
| 2004/0165546 A1 | 8/2004 | Roskind | |
| 2004/0203846 A1 | 10/2004 | Caronni et al. | |
| 2004/0235455 A1 | 11/2004 | Jiang | |
| 2004/0236702 A1 | 11/2004 | Fink et al. | |
| 2004/0258003 A1 | 12/2004 | Kotot et al. | |
| 2004/0264428 A1 | 12/2004 | Choi et al. | |
| 2005/0003797 A1 | 1/2005 | Baldwin | |
| 2005/0009499 A1 | 1/2005 | Koster | |
| 2005/0020216 A1 | 1/2005 | Bune | |
| 2005/0024201 A1 | 2/2005 | Culpepper et al. | |
| 2005/0026650 A1 | 2/2005 | Russell | |
| 2005/0030929 A1 | 2/2005 | Swier | |
| 2005/0075114 A1 | 4/2005 | Dennison et al. | |
| 2005/0108257 A1 | 5/2005 | Ishii et al. | |
| 2005/0108529 A1 | 5/2005 | Juneau | |
| 2005/0135375 A1 | 6/2005 | Hurtta et al. | |
| 2005/0143057 A1 | 6/2005 | Shiraga et al. | |
| 2005/0144279 A1 | 6/2005 | Wexelblat | |
| 2005/0160276 A1 | 7/2005 | Braun et al. | |
| 2005/0172148 A1 | 8/2005 | Ying | |
| 2005/0177645 A1 | 8/2005 | Dowling et al. | |
| 2005/0223389 A1 | 10/2005 | Klein et al. | |
| 2005/0239448 A1 | 10/2005 | Bayne | |
| 2005/0239498 A1 | 10/2005 | Dorenbosch et al. | |
| 2005/0250527 A1 | 11/2005 | Jugl | |
| 2005/0254451 A1 | 11/2005 | Grosbach | |
| 2005/0255893 A1 | 11/2005 | Jin et al. | |
| 2005/0259654 A1 | 11/2005 | Faulk, Jr. | |
| 2005/0269402 A1 | 12/2005 | Spitzer et al. | |
| 2005/0283518 A1 | 12/2005 | Sargent | |
| 2006/0003775 A1 | 1/2006 | Bull et al. | |
| 2006/0031387 A1 | 2/2006 | Hamzeh et al. | |
| 2006/0031493 A1 | 2/2006 | Cugi | |
| 2006/0046647 A1 | 3/2006 | Parikh et al. | |
| 2006/0074814 A1 | 4/2006 | Lovell et al. | |
| 2006/0075098 A1 | 4/2006 | Becker et al. | |
| 2006/0101019 A1 | 5/2006 | Nelson et al. | |
| 2006/0107327 A1 | 5/2006 | Sprigg et al. | |
| 2006/0182074 A1 | 8/2006 | Kubler et al. | |
| 2006/0223498 A1 | 10/2006 | Gallagher et al. | |
| 2006/0224750 A1 | 10/2006 | Davies et al. | |
| 2006/0244589 A1 | 11/2006 | Schranz | |
| 2006/0281457 A1 | 12/2006 | Huotari et al. | |
| 2007/0002844 A1 | 1/2007 | Ali | |
| 2007/0008894 A1 | 1/2007 | Lynch et al. | |
| 2007/0025245 A1 | 2/2007 | Porras et al. | |
| 2007/0032225 A1 | 2/2007 | Konicek et al. | |
| 2007/0032269 A1 | 2/2007 | Shostak | |
| 2007/0041350 A1 | 2/2007 | Famolari | |
| 2007/0066318 A1 | 3/2007 | Danzeisen et al. | |
| 2007/0074272 A1 | 3/2007 | Watanabe | |
| 2007/0094601 A1 | 4/2007 | Greenberg et al. | |
| 2007/0094716 A1 | 4/2007 | Farino et al. | |
| 2007/0097093 A1 | 5/2007 | Oshita et al. | |
| 2007/0097938 A1 | 5/2007 | Nylander et al. | |
| 2007/0097939 A1 | 5/2007 | Nylander et al. | |
| 2007/0097983 A1 | 5/2007 | Nylander et al. | |
| 2007/0099561 A1 | 5/2007 | Voss | |
| 2007/0104166 A1 | 5/2007 | Rahman et al. | |
| 2007/0109101 A1 | 5/2007 | Colby | |
| 2007/0111706 A1 | 5/2007 | Kumar et al. | |
| 2007/0123253 A1 | 5/2007 | Simongini et al. | |
| 2007/0124802 A1 | 5/2007 | Anton et al. | |
| 2007/0129045 A1 | 6/2007 | Aerrabotu | |
| 2007/0133563 A1 | 6/2007 | Hundscheidt et al. | |
| 2007/0150732 A1 | 6/2007 | Suzuki et al. | |
| 2007/0155421 A1 | 7/2007 | Alberth et al. | |
| 2007/0167175 A1 | 7/2007 | Wong | |
| 2007/0183427 A1 | 8/2007 | Nylander et al. | |
| 2007/0184815 A1 | 8/2007 | Aebi | |
| 2007/0199076 A1 | 8/2007 | Rensin et al. | |
| 2007/0220252 A1 | 9/2007 | Sinko et al. | |
| 2007/0225029 A1 | 9/2007 | Abusch-Magder | |
| 2007/0232332 A1 | 10/2007 | Holur | |
| 2007/0258418 A1 | 11/2007 | Wurtenberger et al. | |
| 2007/0263608 A1 | 11/2007 | Han et al. | |
| 2007/0270152 A1 | 11/2007 | Nylander et al. | |
| 2007/0275739 A1 | 11/2007 | Blackburn | |
| 2007/0287501 A1 | 12/2007 | Hoshina | |
| 2007/0297373 A1 | 12/2007 | Saifullah et al. | |
| 2008/0043972 A1 | 2/2008 | Ruetschi et al. | |
| 2008/0049702 A1 | 2/2008 | Meylan et al. | |
| 2008/0065752 A1 | 3/2008 | Ch'ng et al. | |
| 2008/0070547 A1 | 3/2008 | Schreyer | |
| 2008/0072292 A1 | 3/2008 | Narjala | |
| 2008/0076386 A1 | 3/2008 | Khetawat | |
| 2008/0076392 A1 | 3/2008 | Khetawat et al. | |
| 2008/0076393 A1 | 3/2008 | Khetawat et al. | |
| 2008/0076398 A1 | 3/2008 | Mate et al. | |
| 2008/0076412 A1 | 3/2008 | Khetawat et al. | |
| 2008/0076419 A1 | 3/2008 | Khetawat et al. | |
| 2008/0076420 A1 | 3/2008 | Khetawat et al. | |
| 2008/0076425 A1 | 3/2008 | Khetawat et al. | |
| 2008/0081636 A1 | 4/2008 | Nylander et al. | |
| 2008/0082538 A1 | 4/2008 | Meijer et al. | |
| 2008/0084291 A1* | 4/2008 | Campion | G08B 29/145 |
| | | | 340/514 |
| 2008/0119160 A1 | 5/2008 | Andriantsiferana et al. | |
| 2008/0126531 A1 | 5/2008 | Setia et al. | |
| 2008/0132239 A1 | 6/2008 | Khetawat et al. | |
| 2008/0133742 A1 | 6/2008 | Southiere et al. | |
| 2008/0141348 A1 | 6/2008 | Hovnanian | |
| 2008/0151807 A1 | 6/2008 | Meier et al. | |
| 2008/0155649 A1 | 6/2008 | Maler et al. | |
| 2008/0162489 A1 | 7/2008 | Reponen et al. | |
| 2008/0168099 A1 | 7/2008 | Skaf | |
| 2008/0181184 A1 | 7/2008 | Kezys | |
| 2008/0207170 A1 | 8/2008 | Khetawat et al. | |
| 2008/0242280 A1 | 10/2008 | Shapiro et al. | |
| 2008/0244148 A1 | 10/2008 | Nix et al. | |
| 2008/0254792 A1 | 10/2008 | Ch'ng | |
| 2008/0261602 A1 | 10/2008 | Livneh | |
| 2008/0274753 A1 | 11/2008 | Attar et al. | |

(56) References Cited

U.S. PATENT DOCUMENTS

| | | |
|---|---|---|
| 2008/0281687 A1 | 11/2008 | Hurwitz et al. |
| 2008/0282327 A1 | 11/2008 | Winget et al. |
| 2008/0293382 A1 | 11/2008 | Lubenski et al. |
| 2008/0293433 A1 | 11/2008 | Wallis |
| 2008/0299984 A1 | 12/2008 | Shimomura |
| 2008/0299992 A1 | 12/2008 | Eitan et al. |
| 2008/0305792 A1 | 12/2008 | Khetawat et al. |
| 2008/0305801 A1 | 12/2008 | Burgess et al. |
| 2008/0305834 A1 | 12/2008 | Janiszewski et al. |
| 2008/0318551 A1 | 12/2008 | Palamara et al. |
| 2009/0012898 A1 | 1/2009 | Sharma et al. |
| 2009/0031006 A1 | 1/2009 | Johnson et al. |
| 2009/0037973 A1 | 2/2009 | Gustave et al. |
| 2009/0042593 A1 | 2/2009 | Yavuz et al. |
| 2009/0046632 A1 | 2/2009 | Nanda et al. |
| 2009/0046665 A1 | 2/2009 | Robson et al. |
| 2009/0047945 A1 | 2/2009 | Zhang |
| 2009/0059822 A1 | 3/2009 | Morrill et al. |
| 2009/0061821 A1 | 3/2009 | Chen et al. |
| 2009/0061873 A1 | 3/2009 | Bao et al. |
| 2009/0077620 A1 | 3/2009 | Ravi et al. |
| 2009/0082010 A1 | 3/2009 | Lee |
| 2009/0082020 A1 | 3/2009 | Ch'ng et al. |
| 2009/0092080 A1 | 4/2009 | Balasubramanian et al. |
| 2009/0092081 A1 | 4/2009 | Balasubramanian et al. |
| 2009/0092096 A1 | 4/2009 | Czaja |
| 2009/0092097 A1 | 4/2009 | Nylander et al. |
| 2009/0093232 A1 | 4/2009 | Gupta et al. |
| 2009/0094351 A1 | 4/2009 | Gupta et al. |
| 2009/0094680 A1 | 4/2009 | Gupta et al. |
| 2009/0097436 A1 | 4/2009 | Vasudevan et al. |
| 2009/0098871 A1 | 4/2009 | Gogic |
| 2009/0109979 A1 | 4/2009 | Tong |
| 2009/0111499 A1 | 4/2009 | Bosch |
| 2009/0119750 A1 | 5/2009 | Sembugamoorthy et al. |
| 2009/0122773 A1 | 5/2009 | Gogic |
| 2009/0124262 A1 | 5/2009 | Vela et al. |
| 2009/0129336 A1 | 5/2009 | Osborn et al. |
| 2009/0129350 A1 | 5/2009 | Khandekar et al. |
| 2009/0131050 A1 | 5/2009 | Osborn |
| 2009/0131098 A1 | 5/2009 | Khandekar et al. |
| 2009/0135749 A1 | 5/2009 | Yang |
| 2009/0135794 A1 | 5/2009 | Su et al. |
| 2009/0156213 A1 | 6/2009 | Spinelli et al. |
| 2009/0161682 A1 | 6/2009 | Johnson et al. |
| 2009/0163216 A1 | 6/2009 | Hoang et al. |
| 2009/0163224 A1 | 6/2009 | Dean |
| 2009/0164547 A1 | 6/2009 | Ch'ng et al. |
| 2009/0170440 A1 | 7/2009 | Eyuboglu et al. |
| 2009/0170528 A1 | 7/2009 | Bull et al. |
| 2009/0180428 A1 | 7/2009 | Viswanath |
| 2009/0191844 A1 | 7/2009 | Morgan et al. |
| 2009/0191845 A1 | 7/2009 | Morgan et al. |
| 2009/0210324 A1 | 8/2009 | Bhogal |
| 2009/0213825 A1 | 8/2009 | Gupta et al. |
| 2009/0215429 A1 | 8/2009 | Caldwell et al. |
| 2009/0215452 A1 | 8/2009 | Balasubramanian et al. |
| 2009/0221303 A1 | 9/2009 | Soliman |
| 2009/0233574 A1 | 9/2009 | Shinozaki |
| 2009/0245176 A1 | 10/2009 | Balasubramanian et al. |
| 2009/0247157 A1 | 10/2009 | Yoon et al. |
| 2009/0253421 A1 | 10/2009 | Camp et al. |
| 2009/0253432 A1 | 10/2009 | Willey et al. |
| 2009/0257434 A1 | 10/2009 | Song et al. |
| 2009/0279701 A1 | 11/2009 | Moisand et al. |
| 2009/0288152 A1 | 11/2009 | Huber |
| 2009/0291667 A1 | 11/2009 | Vakil et al. |
| 2009/0299788 A1 | 12/2009 | Huber et al. |
| 2009/0325634 A1 | 12/2009 | Bienas et al. |
| 2010/0022266 A1 | 1/2010 | Villier |
| 2010/0027469 A1 | 2/2010 | Gurajala et al. |
| 2010/0040026 A1 | 2/2010 | Melkesetian |
| 2010/0048165 A1 | 2/2010 | Caldwell et al. |
| 2010/0056104 A1 | 3/2010 | Butler |
| 2010/0075658 A1 | 3/2010 | Hou |
| 2010/0113067 A1 | 5/2010 | Fullam et al. |
| 2010/0157941 A1 | 6/2010 | Raghothaman |
| 2010/0167771 A1 | 7/2010 | Raghothaman et al. |
| 2010/0167777 A1 | 7/2010 | Raghothaman et al. |
| 2010/0260068 A1 | 10/2010 | Bhatt et al. |
| 2010/0271962 A1 | 10/2010 | Han |
| 2011/0055928 A1 | 3/2011 | Brindza |
| 2011/0086614 A1 | 4/2011 | Brisebois et al. |
| 2011/0134837 A1 | 6/2011 | Wang et al. |
| 2011/0177794 A1 | 7/2011 | Nylander et al. |
| 2011/0200022 A1 | 8/2011 | Annamalai |
| 2011/0280154 A1 | 11/2011 | Silverstrim et al. |
| 2012/0135712 A1 | 5/2012 | Bari |
| 2012/0258711 A1 | 10/2012 | Bao et al. |
| 2013/0165079 A1 | 6/2013 | Gogic |

FOREIGN PATENT DOCUMENTS

| | | |
|---|---|---|
| CN | 101175333 A | 5/2008 |
| EP | 2286569 | 2/2011 |
| GB | 2425291 A | 10/2006 |
| GB | 2425921 A | 11/2006 |
| JP | 20010264096 | 9/2001 |
| JP | 2003022303 | 1/2003 |
| JP | 2003088521 | 10/2003 |
| JP | 2004112324 | 4/2004 |
| JP | 2005073147 | 3/2005 |
| JP | 2005215849 | 8/2005 |
| JP | 20060674143 | 3/2006 |
| JP | 2008048055 | 2/2008 |
| WO | 02-14987 A2 | 2/2002 |
| WO | 2005076964 A2 | 8/2005 |
| WO | 2007015067 A2 | 2/2007 |
| WO | 2007040449 A1 | 4/2007 |
| WO | 2008047039 A1 | 4/2008 |

OTHER PUBLICATIONS

Office Action dated Nov. 28, 2016 for U.S. Appl. No. 15/179,970, 80 pages.
Office Action dated Jan. 18, 2017 for U.S. Appl. No. 12/276,120, 104 pages.
Office Action dated Jan. 23, 2017 for U.S. Appl. No. 12/465,585, 8 pages.
Office Action dated Nov. 1, 2012 for U.S. Appl. No. 12/276,058, 59 pages.
Office Action dated Nov. 5, 2012 for U.S. Appl. No. 12/484,072, 52 pages.
Office Action dated Nov. 20, 2012 for U.S. Appl. No. 12/275,878, 28 pages.
Japanese Office Action mailed Sep. 13, 2012 for Japanese Patent Application No. 2011-509669, 10 pages.
Canadian Office Action mailed Oct. 30, 2012 for Canadian Patent Application No. 2,722,324, 3 pages.
Japanese Office Action mailed Sep. 13, 2012 for Japanese Patent Application No. 2011-509675, 4 pages.
Office Action dated Dec. 3, 2012 for U.S. Appl. No. 12/275,416, 33 pages.
Office Action dated Jan. 17, 2013 for U.S. Appl. No. 13/554,710, 42 pages.
Final Office Action dated Feb. 15, 2013 for U.S. Appl. No. 12/579,957.
Office Action dated Feb. 26, 2013 for U.S. Appl. No. 12/276,120, 59 pages.
Chinese Office Action for Chinese Application No. 200980117263.8 dated Feb. 16, 2013, 7 pages.
Chinese Office Action for Chinese Application No. 200980117188.5 dated Jan. 31, 2013, 11 pages.
Final Office Action dated Mar. 14, 2013 for U.S. Appl. No. 12/484,072, 34 pages.
Office Action dated Apr. 23, 2013 for U.S. Appl. No. 12/175,293, 41 pages.
Canadian Office Action mailed Mar. 26, 2013 for Canadian Patent Application No. 2,722,324, 4 pages.

(56) References Cited

OTHER PUBLICATIONS

Office Action dated Jul. 15, 2013 for U.S. Appl. No. 13/554,710, 37 pages.
Office Action dated Aug. 13, 2013 for U.S. Appl. No. 12/276,120, 66 pages.
Office Action dated Aug. 12, 2013 for U.S. Appl. No. 12/275,416, 36 pages.
Office Action dated Sep. 9, 2013 for U.S. Appl. No. 12/465,585, 45 pages.
Office Action dated Oct. 2, 2013 for U.S. Appl. No. 12/275,878, 38 pages.
Office Action dated Oct. 3, 2013 for U.S. Appl. No. 13/892,923, 62 pages.
Office Action dated Oct. 22, 2013 for U.S. Appl. No. 13/898,910, 50 pages.
Office Action dated Oct. 3, 2013 for U.S. Appl. No. 13/934,644, 17 pages.
Chinese Office Action dated Oct. 24, 2013 for Chinese Patent Application No. 200980117263.8, 13 pages.
Chinese Office Action dated Oct. 21, 2013 for Chinese Patent Application No. 200980117188.5, 11 pages.
Japanese Office Action dated Oct. 3, 2013 for Japanese Patent Application No. 2011-509669, 15 pages.
Office Action dated Dec. 12, 2013 for U.S. Appl. No. 12/276,120, 78 pages.
Notice of Allowance dated Feb. 13, 2014 for U.S. Appl. No. 12/275,878, 34 pages.
Hasan et al., "Survivable Wireless Access Network Design with Dual-homing Capabilities"; IEEE Global Telecommunications Conference, Nov. 27-Dec. 1, 2006, 5 pgs.
Japanese Office Action dated Jan. 16, 2014 for Japanese Patent Application No. 2013-026198, 8 pages.
Office Action dated Mar. 26, 2014 for U.S. Appl. No. 12/465,585, 44 pages.
Office Action dated Mar. 24, 2014 for U.S. Appl. No. 13/934,644, 50 pages.
Notice of Allowance dated Apr. 4, 2014 for U.S. Appl. No. 14/090,802, 63 pages.
Office Action dated Mar. 24, 2014 for U.S. Appl. No. 13/671,191, 63 pages.
Office Action dated Jun. 9, 2014 for U.S. Appl. No. 12/276,120, 92 Pages.
Office Action dated Jun. 11, 2014 for U.S. Appl. No. 13/675,150, 68 Pages.
Chinese Office Action dated Jun. 19, 2014 for Chinese Patent Application No. 200980117188.5, 5 Pages.
Canadian Office Action dated May 13, 2014 for Canadian Patent Application 2,722,367, 5 Pages.
Office Action dated Jun. 10, 2014 for U.S. Appl. No. 14/253,553, 16 pages.
Office Action dated Sep. 9, 2014 for U.S. Appl. No. 12/276,120, 93 pages.
Office Action dated Nov. 6, 2014 for U.S. Appl. No. 12/465,585, 43 pages.
Chinese Office Action dated Dec. 22, 2014 for Chinese Patent Application No. 200980117188.5, 4 Pages.
Office Action dated Dec. 23, 2014 for U.S. Appl. No. 13/917,153, 90 pages.
Office Action dated Feb. 4, 2015 for U.S. Appl. No. 13/949,983, 90 pages.
European Office Action dated Feb. 2, 2015 for European Patent Application No. 09747521.4, 4 pages.
Office Action dated Feb. 19, 2015 for U.S. Appl. No. 12/276,120, 90 pages.
Office Action dated Mar. 13, 2015 for U.S. Appl. No. 12/465,585, 39 Pages.
Office Action dated Apr. 17, 2015 for U.S. Appl. No. 14/286,414, 55 Pages.
Office Action dated Mar. 30, 2015 for U.S. Appl. No. 14/219,543, 81 Pages.
Office Action dated Mar. 26, 2015 for U.S. Appl. No. 14/472,012, 62 Pages.
Office Action dated May 18, 2015 for U.S. Appl. No. 14/567,839, 59 Pages.
Canadian Office Action dated Apr. 7, 2015 for Canadian Patent Application No. 2,722,367, 6 Pages.
Office Action dated May 5, 2015 for U.S. Appl. No. 14/660,549, 25 pages.
Office Action dated Jun. 29, 2015 for U.S. Appl. No. 13/949,983, 39 pages.
Office Action dated Jul. 13, 2015 for U.S. Appl. No. 14/520,274, 69 pages.
Office Action dated Jul. 22, 2015 for U.S. Appl. No. 12/276,120, 120 pages.
Chinese Office Action dated Jun. 30, 2015 for Chinese Patent Application No. 200980117188.5, 7 pages.
Office Action dated Sep. 24, 2015 for U.S. Appl. No. 14/472,012, 40 pgs.
Office Action dated Aug. 19, 2015 for U.S. Appl. No. 12/465,585, 42 pages.
Office Action dated Aug. 20, 2015 for U.S. Appl. No. 14/219,543, 43 pages.
Office Action dated Sep. 11, 2015 for U.S. Appl. No. 14/286,414, 28 pages.
Office Action dated Oct. 30, 2015 for U.S. Appl. No. 13/949,983, 19 pages.
Final Office Action dated Jan. 21, 2016 for U.S. Appl. No. 12/276,120, 108 pages.
Final Office Action dated Jan. 21, 2016 for U.S. Appl. No. 12/465,585, 28 pages.
Office Action dated Feb. 8, 2016 for U.S. Appl. No. 14/219,543, 40 pages.
Office Action dated Mar. 17, 2016 for U.S. Appl. No. 12/484,072, 97 pages.
Office Action dated Apr. 6, 2016 for U.S. Appl. No. 14/455,614, 97 pages.
Office Action dated Feb. 3, 2016 for U.S. Appl. No. 14/472,012, 42 pages.
Office Action dated Apr. 29, 2016 for U.S. Appl. No. 14/831,013, 76 pages.
European Office Action dated May 9, 2016 for European Patent Application No. 09752238.7, 2 pages.
Office Action dated Jun. 29, 2016 for U.S. Appl. No. 12/276,120, 106 pages.
Notice of Allowance mailed Jul. 22, 2016 for U.S. Appl. No. 14/472,012, 45 pages.
Notice of Allowance mailed Feb. 3, 2016 for U.S. Appl. No. 14/739,859, 73 pages.
Office Action dated Aug. 18, 2016 for U.S. Appl. No. 15/048,971, 67 pages.
Office Action dated Aug. 22, 2016 for U.S. Appl. No. 12/465,585, 8 pages.
Office Action dated Oct. 3, 2016 for U.S. Appl. No. 12/484,072, 40 pages.
International Search Report and Written Opinion dated Oct. 27, 2009 for PCT Application Serial No. PCT/US2009/043861, 14 Pages.
International Search Report and Written Opinion mailed Feb. 23, 2010, for PCT Application No. PCT/US2009/043846, 13 pages.
Office Action dated Dec. 31, 2009 for U.S. Appl. No. 11/457,129, 16 pages.
Office Action dated Apr. 17, 2009 for U.S. Appl. No. 11/276,269, 15 pages.
Office Action dated Nov. 4, 2008 for U.S. Appl. No. 11/276,269, 15 pages.
Office Action dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
Office Action dated Mar. 29, 2011 for U.S. Appl. No. 12/276,002, 37 pages.

(56) References Cited

OTHER PUBLICATIONS

Office Action dated Apr. 13, 2011 for U.S. Appl. No. 12/276,058, 40 pages.
Office Action dated Apr. 19, 2011 for U.S. Appl. No. 12/276,238, 22 pages.
Office Action dated May 5, 2011 for U.S. Appl. No. 12/275,015, 32 pages.
Office Action dated Jun. 14, 2011 for U.S. Appl. No. 12/275,878, 35 pages.
Office Action dated Jun. 22, 2011 for U.S. Appl. No. 12/484,072, 38 pages.
Office Action dated Jul. 7, 2011 for U.S. Appl. No. 12/276,257, 24 pages.
Office Action dated Jun. 28, 2011 for U.S. Appl. No. 12/275,925, 18 pages.
Office Action dated Jun. 8, 2011 for U.S. Appl. No. 12/484,026, 30 pages.
Office Action dated Aug. 18, 2011 for U.S. Appl. No. 12/275,416, 39 pages.
Office Action dated Sep. 14, 2011 for U.S. Appl. No. 12/276,002, 35 pages.
Office Action dated Oct. 5, 2011 for U.S. Appl. No. 12/276,058, 37 pages.
Office Action dated Oct. 6, 2011 for U.S. Appl. No. 12/465,483, 50 pages.
Office Action dated Oct. 4, 2011 for U.S. Appl. No. 12/484,135, 44 pages.
Office Action dated Jul. 21, 2011 for U.S. Appl. No. 12/175,293, 30 pages.
Office Action dated Oct. 24, 2011 for U.S. Appl. No. 12/275,925, 14 pages.
Office Action dated Nov. 30, 2011 for U.S. Appl. No. 12/275,878, 38 pages.
Office Action dated Dec. 1, 2011 for U.S. Appl. No. 12/275,996, 44 pages.
Office Action dated Oct. 25, 2011 for U.S. Appl. No. 12/465,580, 39 pages.
Office Action dated Nov. 8, 2011 for U.S. Appl. No. 12/465,468, 50 pages.
Office Action dated Jan. 5, 2012 for U.S. Appl. No. 12/465,585, 43 pages.
Office Action dated Dec. 28, 2011 for U.S. Appl. No. 12/175,293, 38 pages.
Office Action dated Nov. 21, 2011 for U.S. Appl. No. 12/484,026, 37 pages.
Office Action dated Dec. 14, 2011 for U.S. Appl. No. 12/484,072, 44 pages.
Office Action dated Nov. 1, 2011 for U.S. Appl. No. 12/816,087, 33 pages.
Office Action dated Mar. 5, 2012 for U.S. Appl. No. 12/465,598, 55 pages.
Office Action dated May 8, 2012 for U.S. Appl. No. 11/457,129, 38 pages.
Office Action dated Mar. 19, 2012 for U.S. Appl. No. 12/276,120, 68 pages.
Office Action dated Mar. 30, 2012 for U.S. Appl. No. 12/484,026, 30 pages.
Notice of Allowance dated Apr. 3, 2012 for U.S. Appl. No. 12/275,996, 38 pages.
Office Action dated Apr. 10, 2012 for U.S. Appl. No. 12/275,416, 32 pages.
Office Action dated Apr. 10, 2012 for U.S. Appl. No. 12/484,135, 45 pages.
Notice of Allowance dated Apr. 25, 2012 for U.S. Appl. No. 12/465,468, 35 pages.
Office Action dated Jul. 16, 2012 for U.S. Appl. No. 12/275,878, 37 pages.
Office Action dated Jul. 10, 2012 for U.S. Appl. No. 12/465,585, 32 pages.
Office Action dated Apr. 13, 2012 for U.S. Appl. No. 13/316,106, 35 pages.
Office Action dated Sep. 5, 2012 for U.S. Appl. No. 12/276,120, 49 pages.
Office Action dated Aug. 16, 2012 for U.S. Appl. No. 12/465,598, 31 pages.
Office Action dated Sep. 6, 2012 for U.S. Appl. No. 12/579,957, 51 pages.
Office Action dated Sep. 10, 2012 for U.S. Appl. No. 12/276,002, 54 pages.
Office Action dated Oct. 2, 2012 for U.S. Appl. No. 12/484,026, 29 pages.
Office Action dated Oct. 11, 2012 for U.S. Appl. No. 13/487,794, 45 pages.
Office Action dated Oct. 9, 2012 for U.S. Appl. No. 13/298,924, 51 pages.
Office Action for U.S. Appl. No. 12/276,120 dated May 15, 2017, 172 pages.
Office Action for U.S. Appl. No. 15/364,250 dated Jul. 14, 2017, 71 pages.
Office Action for U.S. Appl. No. 15/159,755 dated May 10, 2017, 88 pages.
European Office Action dated Feb. 1, 2017 for European Patent Application No. 09752238.7, 5 pages.

* cited by examiner

INTRA-PREMISES CONTENT AND EQUIPMENT MANAGEMENT IN A FEMTOCELL NETWORK

CROSS-REFERENCE TO RELATED APPLICATIONS

This application is a continuation of, and claims the benefit of priority to each of, U.S. patent application Ser. No. 14/286,414 entitled "INTRA-PREMISES CONTENT AND EQUIPMENT MANAGEMENT IN A FEMTOCELL NETWORK," filed May 23, 2014, which is a continuation of U.S. patent application Ser. No. 13/554,710 entitled "INTRA-PREMISES CONTENT AND EQUIPMENT MANAGEMENT IN A FEMTOCELL NETWORK," filed Jul. 20, 2012 (now U.S. Pat. No. 8,787,342 issued on Jul. 22, 2014), which is a continuation of U.S. patent application Ser. No. 12/465,580 entitled "INTRA-PREMISES CONTENT AND EQUIPMENT MANAGEMENT IN A FEMTOCELL NETWORK" and filed on May 13, 2009 (now U.S. Pat. No. 8,274,958 issued on Sep. 25, 2012), which claims the benefit of U.S. Provisional Patent Application No. 61/052,813 entitled "MANAGEMENT OF ACCESS TO FEMTO CELL COVERAGE" and filed on May 13, 2008. The entireties of each of these applications are incorporated herein by reference.

TECHNICAL FIELD

The subject application relates to wireless communications and, more particularly, to management of content and administration of equipment enabled by a femtocell network that serves a confined area.

BACKGROUND

Femtocells—building-based wireless access points interfaced with a wired broadband network—are generally deployed to improve indoor wireless coverage and to offload a mobility radio access network (RAN) operated by a wireless network and service provider. Femtocells typically operate in licensed portions of the electromagnetic spectrum, and generally offer plug-and-play installation. Improved indoor coverage includes stronger signal and improved reception (e.g., voice or data), ease of session or call initiation and session or call retention as well. Offloading a RAN can reduce operational and transport costs for a service provider since a lesser number of end users utilizes over-the-air (OTA) radio resources (e.g., radio frequency bands and channels), which are typically limited.

Coverage of a femtocell, or femto access point (AP), is generally intended to be confined within the bounds of an indoor compound (e.g., a residential or commercial building) in order to mitigate interference among mobile stations covered by a macrocell and terminals covered by the femto AP. Additionally, confined coverage can reduce cross-talk among terminals serviced by disparate, neighboring femtocells as well. Indoor wireless coverage improvements through femtocell also can mitigate customer attrition as long as a favorable subscriber perception regarding voice coverage and other data services with substantive delay sensitivity, or otherwise, is attained. In addition, a richer variety of wireless voice and data services can be offered to customers through a femtocell since such service offerings do not rely primarily on mobility RAN resources.

Integration of intra-premises networks such as computer servers and related accessories within a small business and wireless service(s) typically exploits telecommunication technologies with a substantive adoption threshold in view of complexities associated integration implementation. In addition, connectivity of conventional devices and systems within intra-premises network to wireless routers and access points that can provide wireless service generally is limited and thus hinders effective network integration and customer adoption of systems that can enable integrated wired and wireless services. Accordingly, prospective advantages associated with integrated service and related intra-premises networking have been marginally exploited.

DETAILED DESCRIPTION

Figure 1:
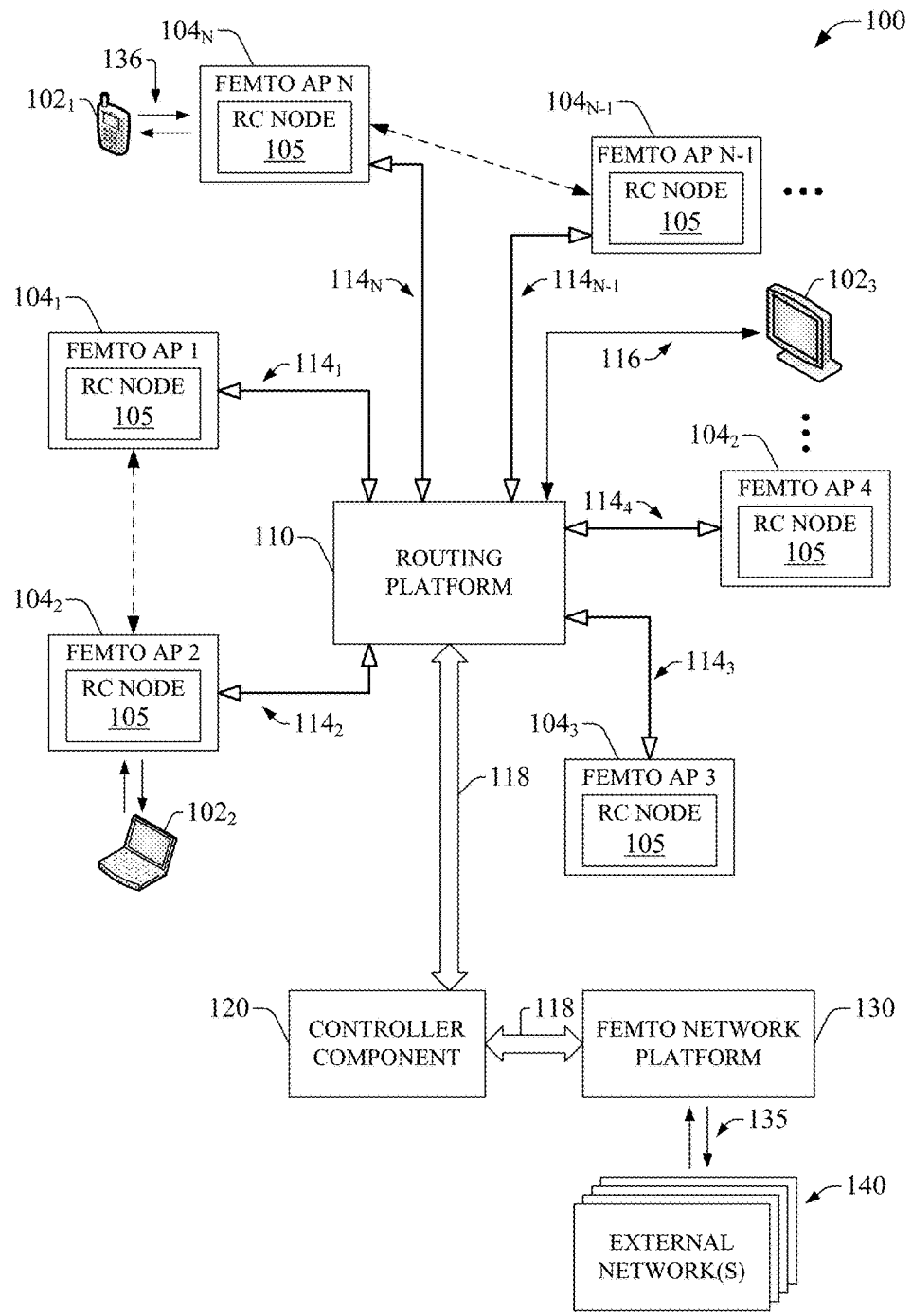
FIG. 1 illustrates a diagram of an example enterprise femto network in accordance with aspects of the subject specification.

The subject application is now described with reference to the drawings, wherein like reference numerals are used to refer to like elements throughout. In the following description, for purposes of explanation, numerous specific details are set forth in order to provide a thorough understanding of the present application. It may be evident, however, that the subject invention may be practiced without these specific details. In other instances, well-known structures and devices are shown in block diagram form in order to facilitate describing the present invention.

This application is related to co-pending U.S. patent application Ser. No. 12/465,483, entitled "LOCATION-BASED SERVICES IN A FEMTOCELL NETWORK," and filed on May 13, 2009; co-pending U.S. patent application Ser. No. 12/465,468 entitled "FEMTOCELL ARCHITECTURE FOR INFORMATION MANAGEMENT," filed on May 13, 2009; and co-pending U.S. patent application Ser. No. 12/465,585 entitled "COMMERCE AND SERVICES IN A FEMTOCELL NETWORK" and filed on May 13, 2009. The entireties of each of these applications are incorporated herein by reference As used in this application, the terms "component," "system," "architecture," "platform," "node," "layer," "selector," "interface," "module," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of non-limiting illustration, both an application running on a server and the server can be a component. One or more components may reside within a process and/or thread of execution and a component may be localized on one computer and/or distributed between two or more computers. These components also can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry that is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software or firmware that confers at least in part the functionality of the electronic components. An interface can include input/output (I/O) components as well as associated processor, application, and/or API components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," "mobile device," "subscriber station," "subscriber equipment," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B," "evolved Node B (eNode B)," home Node B (HNB)," "home access point (HAP)," or the like, are utilized interchangeably in the subject specification and drawings, and refer to a wireless network component or apparatus that serves and receives data, control, voice, video, sound, gaming, or substantially any data-stream or signaling-stream from a set of subscriber stations. It is noted that in the subject specification and drawings, context or explicit distinction provides differentiation with respect to access points or base stations that serve and receive data from a mobile device in an outdoor environment, and access points or base stations that operate in a confined, primarily indoor environment. Data and signaling streams can be packetized or frame-based flows.

Furthermore, the terms "user," "subscriber," "customer," "consumer," "prosumer," "agent," "owner" and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms) which can provide simulated vision, sound recognition and so forth. As utilized herein, the term "prosumer" indicate the following contractions: professional-consumer and producer-consumer.

Further yet, the terms "wireless network" and "network" are used interchangeably in the subject application, when context wherein the term is utilized warrants distinction for clarity purposes such distinction is made explicit. Likewise, the terms "femtocell access point", "femto access point", "femtocell," "femto" and the like also are utilized interchangeably.

The subject application provides system(s) and method(s) to route traffic and signaling between a set of networked femto access points (APs) and enable and enable management of content and equipment that is part of a network functionally coupled to the set of networked femto APs. The network and equipment thereof can be deployed within the premises wherein the set of networked femto APs operate. A femto AP in the set of networked femto APs is functionally linked to a routing platform that manages traffic and signaling, and is functionally connected to a controller component that relays at least part of data and control to a femto network platform. The femto network platform allows access to one or more external networks. Routing platform assesses billing charges associated with a call session served at least in part through one or more femto APs in the set of networked femto APs and the routing platform. Call sessions can include intra-network or inter-network communication, wherein intra-network communication can include push-to-point delivery of traffic and signaling, while inter-network communication can include exchange of data and control among a device served through an external network and a device served through a femto AP linked to the routing platform. In addition, routing platform can effect soft handover of call sessions amongst two femto APs in the set of femto APs, and it can implement hard handover of a call session between a femto AP and a component in an external network that can serve the call session.

The routing platform functionally couples the networked equipment and the set of femto APs to enable content manipulation amongst a mobile device and the equipment. Manipulation of content can include exchange of digital entities among a mobile device served through a femto AP in the set of networked femto APs and equipment that is part of the network of deployed equipment. In addition, the mobile device can push content to specific equipment and remove or reorganize content extant in the equipment.

Routing platform also affords remote control of the networked equipment. In an aspect, control can be effected through a mobile device configured to wirelessly deliver one or more authorized commands Such commands can be received by a femto AP within the set of networked femto APs and directed to the equipment via the routing platform. In addition, to such active control, the routing platform also affords passive control, which includes monitoring networked equipment in accordance at least in part with a monitoring profile.

Delivery of advertisement and monetary incentive(s) can be provided through the routing platform to the equipment. Monetary incentive(s) or advertisement are delivered to a device, wherein the incentive(s) or advertisement can be customized at least in part on at least one of location of the device within an enterprise femto network coverage area spanned through the set of networked femto APs. The device can be a mobile device that operated within the enterprise femto network or in an intra-premises network functionally couple thereto. In an aspect, the recipient mobile device can accept or reject reception of incentive(s) or advertisement. Commercial transaction(s) also can be implemented based at least in part on a commercial profile associated with a unique identifier of the mobile device. A commerce profile can be configured autonomously by a commerce component that delivers incentive(s) and enables one or more commercial transaction(s). Alternatively or additionally, a consumer associated with the mobile device can configure the commerce profile through an external network, such as the Internet. A marketing component can exploit advertisement campaign(s) and response thereto by mobile device(s) or device(s) within an intra-premises network to generate business intelligence and adjust advertisement content and delivery as well as an advertised service.

Revenue sharing also can be configured amongst an operator that manages a business in which the enterprise femto network, and associated intra-premises network(s), are deployed and a set of advertisers; revenue sharing can be based at least in part upon exchange of service unit(s) for exposure to advertisement. The set of advertisers can include at least one of advertisers internal to the business operator or a service provider, or advertisers external thereto.

Routing platform further provides security features related to operation of specific equipment and wireless services supplied via the routing platform. In an aspect, security includes manipulation of equipment based at least in part on location of a mobile device that is served through the set of network femto APs.

Aspects, features, or advantages of the subject application can be exploited in substantially any wireless telecommunication, or radio, technology; for example, Wi-Fi, Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP UMTS; High Speed Packet Access (HSPA); High Speed Downlink Packet Access (HSDPA); High Speed Uplink Packet Access (HSUPA), or LTE Advanced. Additionally, substantially all aspects of the subject application can include legacy telecommunication technologies.

It is noted that various aspects, features, or advantages of the subject application are illustrated in connection with femto access point(s) and associated femto network platform, such aspects or features also can be exploited in indoor-based base stations (e.g., home-based access point(s), enterprise-based access point(s)) that provide wireless coverage through substantially any, or any, disparate telecommunication technologies such as for example Wi-Fi (wireless fidelity) or picocell telecommunication.

FIG. 1 illustrates a diagram of an example enterprise femto network architecture 100 in accordance with aspects of the subject specification. A set of femto access points $104_1$-$104_N$, with N a natural number, can be functionally connected to a routing platform 110 that can be functionally coupled to a controller component 120, which can be operationally linked to a femto network platform 130. It should be appreciated that a single backhaul pipe 118 operationally connects routing platform 110 and controller component 120. Likewise, a single backhaul pipe 118 connects controller component 120 and femto network platform 130. In an aspect, femto network platform 130 can be functionally coupled, via one or more reference link(s) 135, to external network(s) 140, which can include service network(s) such as an internet protocol (IP) multimedia subsystem (IMS). In another aspect, in 3GPP UMTS radio technology, controller component 120 can be embodied in a radio network controller. It is noted that in one or more alternative or additional embodiments, controller component 120 can reside within femto network platform 130 or within one of external network(s) 140, in such an embodiment, femto network platform 140 can connect to routing platform 110 via the one external network among external network(s) 140. It should further be appreciated that example enterprise femto network architecture 100 enables femto APs $104_1$-$104_N$ to be mutually connected, via routing platform 110, in a mesh network configuration, also termed herein as a mesh femto network. The portion of the enterprise femto network within the coverage area spanned by femto APs $104_1$-$104_N$ is private as opposed to public such as a macrocell network.

The number of femto APs $104_\lambda$, with $\lambda=1, 2 \ldots N$, connected to the routing platform 110 can be based at least in part on at least one of a number of ports on or bandwidth available to routing platform 110. Femto APs $114_\lambda$ are functionally connected to routing platform 110 through links $114_\lambda$, which can be broadband, backhaul wired links (e.g., optical fiber backbone, twisted-pair line, T1/E1 phone line, a digital subscriber line (DSL) either synchronous or asynchronous, an asymmetric ADSL, or a coaxial cable . . . ) or a wireless (line-of-sight (LOS) or non-LOS) links. Backhaul link(s) 118 also can wired or wireless. In an aspect, in 3GPP UMTS radio technology, a link $114_\lambda$ can be embodied in at least one of an Iur interface or an Iuh interface. It is noted that the number of channel elements of a link $114_\lambda$ can be lower that the number of channel elements in backhaul link 118. Thus, the plurality of femto APs $104_1$-$104_N$ can be served via femto network platform 130, through single backhaul pipes 118, with less backhaul resources than in a conventional system in which a backhaul pipe 118 is functionally connected to each femto AP.

Femto APs $104_1$-$104_N$ are deployed within a confined coverage area, which can include either a single-floor or multi-floor facility or enterprise. Deployment plan generally minimizes dead spots and includes a number of femto APs sufficient to achieve operational redundancy, such that if one or more of the provisioned femto APs fails, disparate additional femto AP(s) functionally connected to routing platform 110 can be employed for communication. Thus, the mesh femto network can be self-healing. An enterprise can include, but is not limited to including, one of an office building; a residential complex, a business building such as department store, a bank, a restaurant, or a warehouse; a government facility; a school; a hospital; a hotel; a factory; an airport; a recreation or city park; or the like.

Figure 2A:
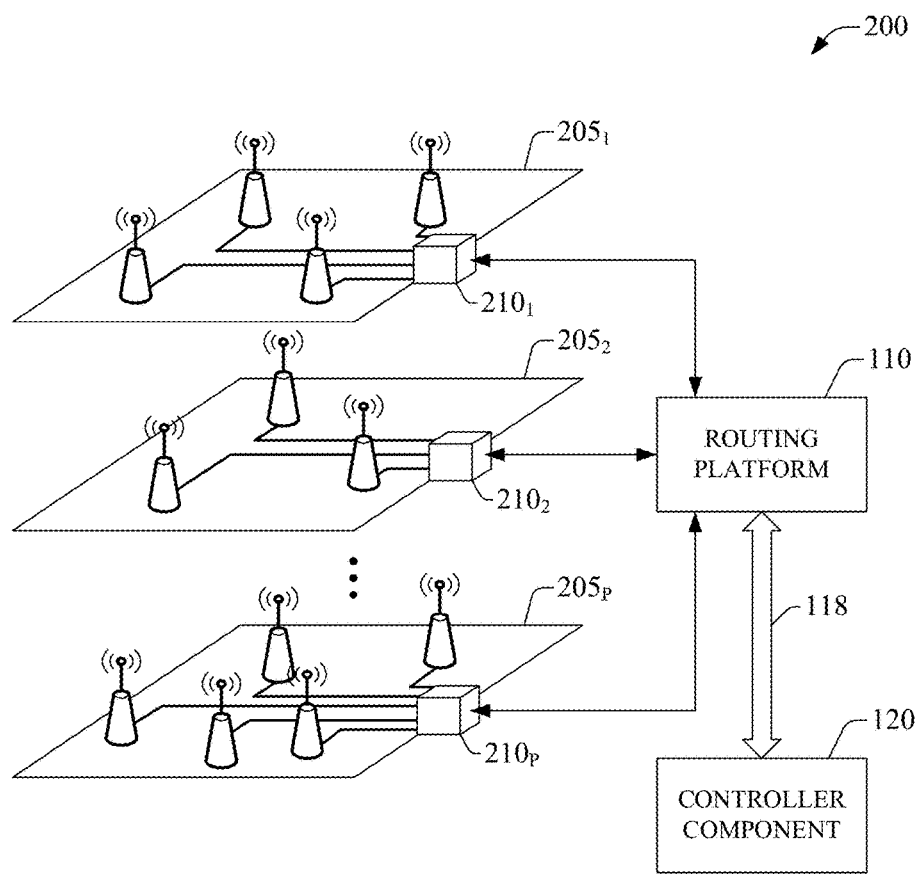
FIGS. 2A-2C illustrate, respectively, a block diagram of an example multi-coverage-area femto mesh network and a block diagram of an example femto mesh network in which routing in a multi-loci environment is decentralized, and an example femto mesh network wherein various routing platforms related to various enterprise deployments are multiplexed in accordance with aspects described herein.

As an illustration of multi-floor networked embodiments, FIG. 2A displays a block diagram of an example multi-coverage-area femto mesh network 200 in accordance with aspects described herein. Coverage areas, $205_\mu$ ($\mu=1, 2 \ldots$ P) can include indoor environments such as floors in a building and, at least partially, outdoor environments such as parking lots; terraces, decks, or verandas; or sports fields or courts. In each coverage area $205_\mu$, a network interface device (NID) $210_\mu$ centralizes broadband link(s), illustrated as thick lines without arrowheads (for clarity), from each deployed femto AP. NIDs $210_\mu$ are functionally connected to routing platform 110. Deployed femto APs can be further connected to a single backhaul pipe 116 through routing platform 220. Routing platform 220 can direct traffic among wireless devices located in disparate coverage areas. It is noted that routing functionality provided by routing platform 220 is centralized. As an example, consider a scenario in which the example enterprise femto network architecture 200 is deployed in a multi-floor building wherein multiple femto APs can be deployed on each floor, e.g., coverage area $205_\mu$, of the building. In this example, a mobile device on a first floor, e.g., $205_2$, connected to a femto AP on the first floor can establish communication (e.g., voice or data) with another mobile device on a second floor, e.g., 205P, connected to a femto AP therein, without accessing a femto network platform linked to controller component 120.

Figure 2B:
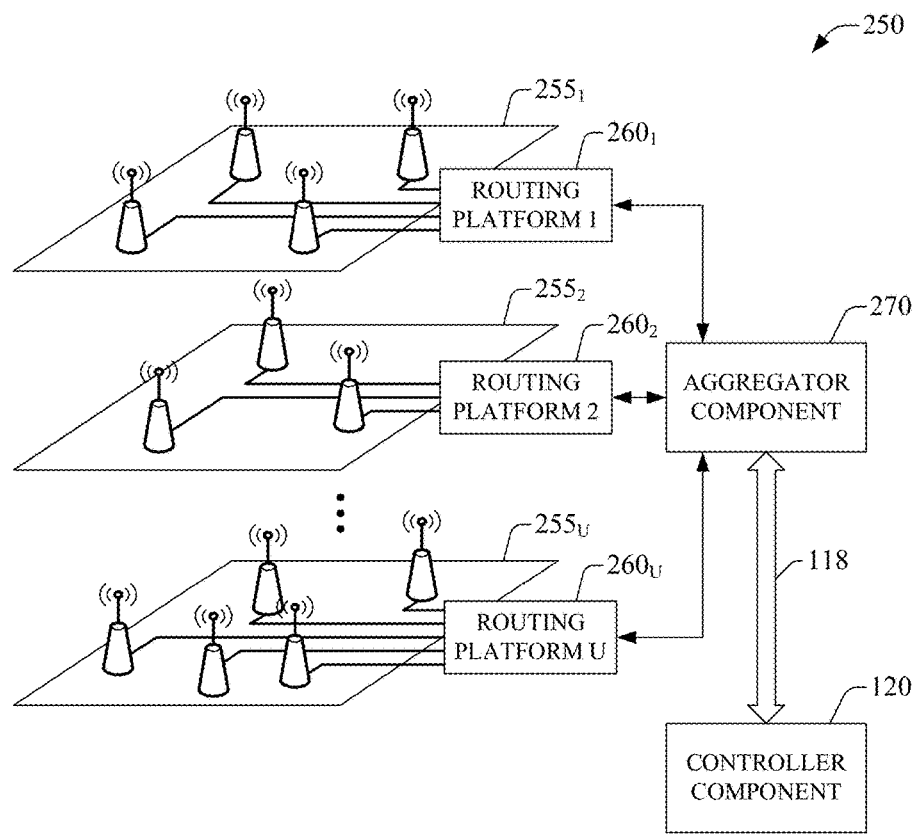

Alternatively or additionally, FIG. 2B displays a block diagram of an example femto mesh network 250 in which routing in a multi-coverage-area environment is decentralized, effected by a set of routing platforms $260_1$-$260_U$, U is a natural number, and each coverage area $255_\gamma$, with $\gamma=1, 2 \ldots U$, linked to each routing platform in the set. An aggregator component 260 interfaces the multi-area femto enterprise network architecture 250 with controller component 120. The multiple routing platforms $260_\gamma$ can communicate with each other such that configuration information with respect to femto APs associated with each routing platform and devices operationally connected to the femto APs is available to each routing platform $260_\gamma$; configuration information can enable, at least in part, internal routing of traffic. An aggregator component 270 can operate as at least one of a pass-through element or as a traffic shaping component, preserving QoS in accordance with predetermined QoS profile(s) for various types of traffic or signaling. In an aspect, aggregator component 270 also can effect routing functionality, and can act as a PBX to allow inter-enterprise communication. As illustrated, one routing platform $260_\gamma$ is deployed on each coverage area $220_\gamma$, with $\gamma=1, 2 \ldots U$, wherein each coverage area can be a floor of a building (e.g., an office building, a school, a department store) and routing platforms $260_\gamma$ on each floor can be mutually functionally connected to create an enterprise femto mesh network structure that can cover the entire building. It is noted that based at least in part on the size of a coverage area $255_\gamma$, more than a single routing platform can be deployed in the coverage area $255_\gamma$. Multiple femto APs can be functionally connected to a single routing platform $260_\gamma$, and multiple routing platforms $220_1$-$220_U$ can be connected together to create a larger mesh femto network.

Processor(s) (not shown) can provide at least part of the functionality of aggregator component 260. To operate or confer at least in part functionality to the aggregator component 260, the processor(s) can store information in, and retrieve information from, a memory (not shown). The information can include at least one of code instructions, data structures, program modules, or the like.

Figure 2C:
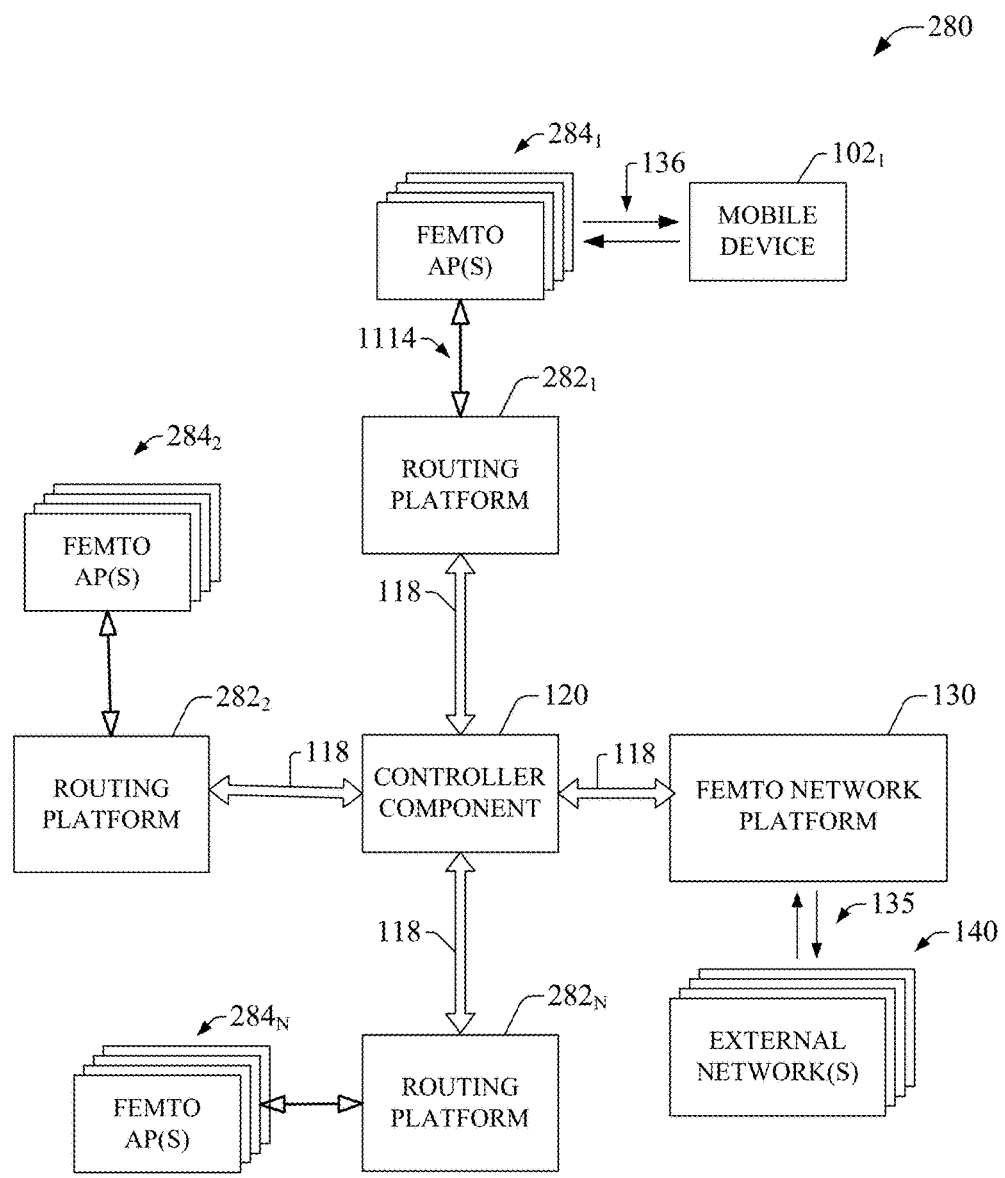

Further, FIG. 2C illustrates an example femto mesh network 280 wherein various routing platforms related to various enterprise deployments can be multiplexed by employing a single controller component 120. According to an aspect, controller component 120 can receive information from a set of routing platforms, $282_1$-$282_N$, wherein N is a natural number. Each of the routing platforms $282_1$-$282_N$ can be connected to respective sets of multiple femto APs $284_1$-$284_N$, which facilitate connectivity to/from mobile device $102_1$ connected, e.g., to a respective set of femto APs $284_1$. Each routing platform $282_1$-$282_N$ can receive data from a mobile device attached to a set of femto APs $284_1$-$284_N$ within the enterprise femto architecture or network. Moreover, routing platforms $282_1$-$282_N$ can perform an analysis to determine information associated with routing of the received data (e.g. source address, destination address, etc.). Further, a route can be determined for transferring the packet from the routing platform based in part on the analysis and/or user defined rules or policies and/or user preferences. In particular, routing platforms $282_1$-$282_N$ can determine whether a soft- (indicated with dashed lines in FIG. 1) or hard-handover can be performed. When a hard handover is to be performed, routing platforms $282_1$-$282_N$ can route the data to the femto network platform 130 controller component 120. It is noted that controller component 120 can typically include functionality of a second RNC or most any other network management component associated with the femto network platform 130, which can be embodied at least in part in a FGW. It is noted, however, that in the subject application controller component 120 does not effect any RNC function(s) or operation(s). In an aspect, as illustrated in example mesh femto network 280, controller component 130 can multiplex the set of routing platforms $282_1$-$282_N$ related to various enterprise deployments.

Figure 3:
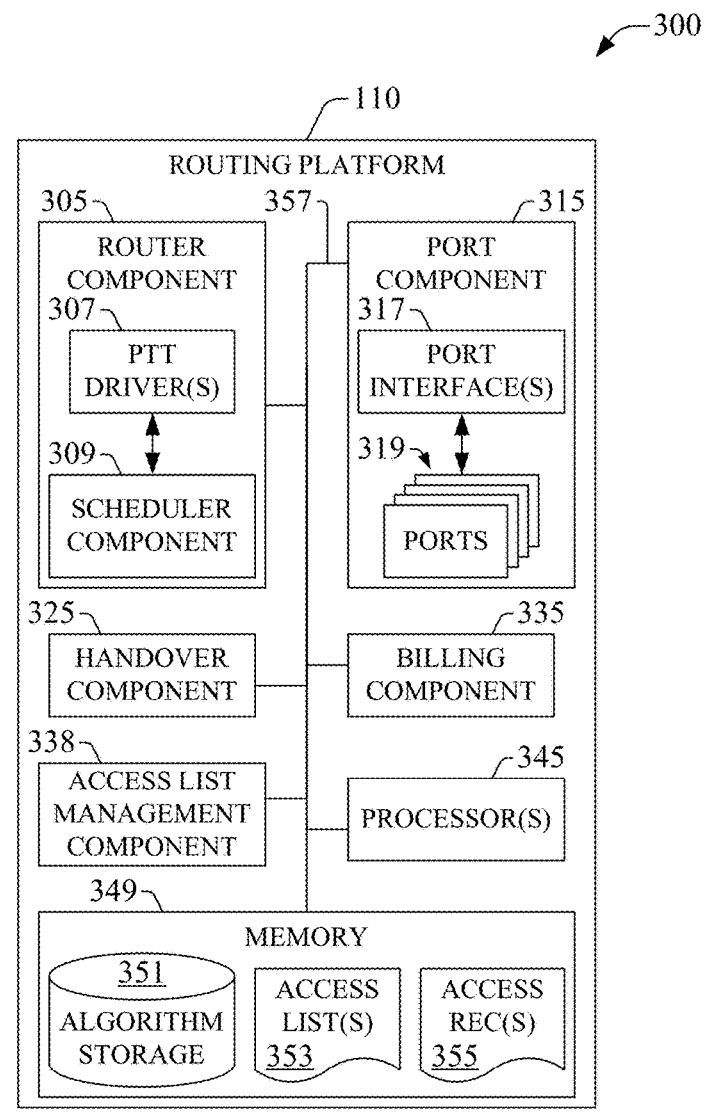
FIG. 3 displays a block diagram of an example embodiment of a routing platform that is part of an enterprise femto network architecture in accordance with aspects disclosed herein.

Connections amongst backhaul links $114_\lambda$ and routing platform 110, NIDs $210_\mu$ and routing platform 110, and routing platform 110 and aggregator component 270 can be effected through a port component 315 within routing platform 110, as illustrated in example embodiment 300 shown in FIG. 3. Port component 315 can include port interface(s) 317 to configure one or more of ports 319, which can include parallel ports (e.g., GPIB, IEEE-1284), serial ports (e.g., RS-232, V.11, USB, FireWire or IEEE-1394 . . . ), Ethernet ports, V.35 ports, X.21 ports, or dry contacts, or the like. Port interface(s) 317 can include a wireless interface such as a wireless card and associated circuitry to implement telecommunication. In addition, port interface(s) 319 can include one or more physical docks that support physical connectors for respective ports 319. Routing platform 110 can be configured, or programmed, to communicate wirelessly with one or more femto AP $104_\lambda$ rather than through routing cables. Configuration can be accomplished trough a display interface (not shown) that enables data entry in routing platform 110, or through a device such as a computer, mobile or otherwise, connected to port component 315.

As illustrated in FIG. 1, each femto AP $104_\lambda$, or femto APs illustrated in embodiments 200 and 250, that is connected to routing platform 110 can include a radio controller (RC) node 105 that includes at least part of the functionality of a radio network controller. Routing platform 110 can functionally connect RC nodes 105 between two or more femto APs deployed within example femto enterprise network system 100. As indicated supra, link(s) $114_\lambda$ can include at least an Iur interface that can route packet stream(s) between the functionally connected two or more femto APs. An RC node 105 can have substantially the same functionality as that controller component 120. However, in one or more architecture(s) or embodiment(s), RC node 105 can have less complexity than controller component 120. Having an RC node 105 in each femto AP $104_\lambda$ can result in an optimal (e.g., sub-linear) or nearly optimal (e.g., linear) scaling of processing demand at routing component with respect to the number of provisioned femto APs in the femto enterprise network architecture. Processing demand in the femto enterprise network increases due to increased routing or scheduling processing. It is noted that scheduling relates to scheduling of packet delivery rather than scheduling of radio resources, which is implemented by routing platform 110. When a femto AP is added to the femto mesh network 100, the RC node 105 associated with the femto AP can provide RNC functionality thereto and thus the mesh network. However, demand for backhaul resources, e.g., backhaul link 118, and controller component 120 does not grow with an increase in the number of femto APs functionally connected to routing component 110. Accordingly, built-in RNC functionality can improve scalability with respect to a networked configuration in which routing platform also acts as a radio network controller.

Routing platform 110 can enable user plane connections directly, and can establish communication, e.g., exchange of voice or data and signaling, between two or more femto APs, e.g., femto AP $104_2$ and $104_N$. Moreover, routing platform 110 can enable communication between mobile devices, e.g., $102_1$ and $102_2$, attached to disparate femto APs, wherein traffic and signaling associated with the communication is routed within the example femto enterprise network 100 without delivery of data or management packets to femto network platform 130. For example, routing platform 110 can direct traffic generated by mobile device $102_1$ served through femto AP $104_N$ to wireless device $102_2$ served by femto AP $104_4$.

Communication amongst mobile device $102_1$ and wireless device $102_2$ can be push-to-talk communication. Alternatively or additionally, routing platform 110 can allow push-to-talk communication between a mobile device and a pseudo-stationary tethered device such as $102_3$. It is noted that, in an aspect, routing platform 110 is traffic agnostic in that a first device, mobile or otherwise, can operate in a first radio technology disparate from a second radio technology employed by a second device, mobile or otherwise, that communicates with the first device through routing platform 110 and via respective femto APs. In an example embodiment 300, illustrated in FIG. 3, routing component 110 can include push-to-talk driver(s) 307 to enable at least in part point-to-point communication among one or more devices, mobile or otherwise in the femto mesh network 100. In view of such internal communication, for outgoing communication(s) off the example mesh femto network 100, routing platform 110 can allocate bandwidth primarily for control, or signaling, and thus traffic on the backhaul network can be substantially reduced. In addition, such communication internal to example enterprise femto network system 100 can reduce communication delay, with ensuing improvement of perceived QoS for latency-sensitive content such as multiplayer gaming, banking transactions and the like.

In an aspect, routing platform 110, via router component 305, can receive carrier-frequency information associated with channels employed for telecommunication within the coverage area of an enterprise femto network 100. Router component 305 can aggregate carrier-frequency data to form a carrier-frequency map. In an aspect, the carrier-frequency map can enable load balancing of traffic within the enterprise femto network 100 through dynamic allocation of bandwidth to specific femto APs functionally connected to the routing platform. Scheduler component 309 can signal a bandwidth allocation to a femto AP within the enterprise femto network 100.

Routing platform 110 can direct a packet received from a femto AP, e.g., $104_{N-1}$, based in part on routing information. In an aspect, routing platform 110 can receive a communication packet from one of the multiple femto APs $104_1$-$104_N$ and can determine routing information associated with the communication packet. In an aspect, the routing information can indicate that the communication packet is to be transferred to femto network platform 130. Accordingly, routing platform 110 can perform a hard handover and direct the packet to femto network platform 110 through controller component 120. In another aspect, the routing information can indicate that the packet can be transferred internally from a first femto AP, e.g., $104_N$, to a second femto AP, e.g., $104_2$, functionally connected to routing platform 110. Moreover, in such case, routing platform 110 can perform a soft handover between a first femto AP ($104_2$) and a second femto AP (e.g., $104_3$) and establish communication such that dead spots or issue scenarios can be avoided or mitigated. Furthermore, routing platform 110 can determine control information, or signaling, for traffic routed directly between femto APs and route the control information, or signaling, to femto network platform via controller component 120 through backhaul pipe 118.

In an example embodiment 300, routing platform 110 includes a router component 305 that can direct traffic and signaling among a set of deployed femto APs, e.g., femto APs $104_1$-$104_N$. Traffic can be routed in accordance at least in part with a set of one or more algorithm(s) retained in memory element 349. Router component 305 can determine a near-optimal or optimal route for a received data or management packet, to avoid network congestion within mesh femto network 100. In addition, router component 305 also can configure point-to-point communication as part of routing functions based at least in part on channel conditions. Moreover, router component 305 can utilize configured access list(s) 353 to route traffic and signaling and ensure data integrity or self-healing routing.

Access list(s) 353 can regulate, at least in part, a level of service provided to user equipment through a femto AP, e.g., $104_{N-1}$. Access list(s) can comprise at least one of whitelist(s) that at least in part identify a set of devices that can be provided wireless service through a femto AP, or blacklist(s) that can explicitly exclude one or more wireless devices from femto service. In addition, wireless devices in blacklist(s) can prompt exception handling procedures that include issuance of alarm(s), notification to authorities, tracking of device location within the enterprise femto network 100, or the like. In an aspect, access list(s) 353 can be received from femto network platform 130, in which access list(s) 353 can resided within a subscriber database and can be configured through at least one of external network(s) 140. In another aspect, routing platform 110 can include access list management component 338 which can generate or modify, at least in part, access list(s) 353 (e.g., whitelist(s) or blacklist(s)) based at least in part on signaling received from one or more femto APs within the set of femto APs deployed as part of the femto enterprise network 100. Access list(s) 353 generated through access list management component 338 can be active for a predetermined period, and after such period elapses can be deleted, either logically or physically, based at least in part on signaling received from one or more network components. Signaling can include mobile device identifier attribute(s). Access list management component 338 can either accept or reject such attribute(s) based at least in part on a set of criteria (not shown) which can be retained within memory 349. Further, for accepted mobile device identifier attribute(s), a default or initial level of access; for instance, almost all or all femto APs deployed as part of enterprise femto network 100 can provide service to an identified mobile device. Default or initial level of access can be modified subsequently based at least in part on additional signaling received by routing platform 110. As an illustration, the set of acceptance or rejection criteria can include at least one of the following. (i) Valid mobile device identifier, e.g., wireless device numbers such as IMSIs, MSISDNs, or other codes or tokens. (ii) Active mobile device identifier or identifier flagged for update; e.g., an identifier that corresponds to an old phone number that is to be updated to a current number. (iii) Status of election (e.g., opt in) or non-election (e.g., opt out) flags for inclusion in a whitelist, wherein status is conveyed, for example, via a K-bit word (K is a natural number) within an entry for the mobile device in a subscriber database. (iv) Operational capabilities of the identified mobile device (e.g., wireless technology utilized by the device such as second generation (2G), third generation (3G), or fourth generation (4G) technologies, radio frequency bands in which the mobile device can receive communications . . . ). (v) Commercial standing of the identified mobile device; e.g., good standing or outstanding bill payments, hotlined mobile device in view of recurring lack of timely payments for service, stolen device . . . ; or the like.

Furthermore, router component 305 can include a scheduler component 309 to establish quality of service (QoS) for communication among two or more devices in accordance at least in part with at least one of traffic priority profile or QoS class (e.g., best effort, maximum bit-error-rate (BER), guaranteed data rate). In an aspect, during provisioning of a femto AP, which can be effected by a provisioning server within femto network platform 130, scheduler component 309 can determine or configure at least one of quality of service (QoS) or one or more queuing functions that can facilitate management of content(s), e.g., traffic or signaling. Scheduler component 309 also can employ load-balancing techniques, which can be implemented through algorithms retained in algorithm storage 351, to enable efficient network or resource(s) utilization.

In addition, scheduler component 309 can utilize access list(s) 347 that control access to one or more femto APs by one or more mobile device to route traffic, e.g., a data packet, and signaling, e.g., a management packet, amongst femto APs in the enterprise femto architecture. In an aspect, access list(s) 347 can allow access to a femto AP, e.g., the access list is a white list, or can include black list(s), which can explicitly determine mobile devices that are denied access to service through one or more femto APs and trigger an exception handling subsequent to attachment attempt(s) effected by black listed mobile devices. In an aspect, exception handling can include authorization of attachment to a femto AP and notification of an authority, as discussed below.

To perform almost any or any handover (e.g., soft handover) internal to example mesh femto network 100 without accessing femto network platform 130, e.g., delivering signaling or traffic thereto, routing platform 110 also can configure and exploit user-plane connection(s). In an aspect, routing component 110 can exploit links 114$_\lambda$, e.g., Iur interfaces, between femto APs 104$_\lambda$ to enable soft handover. As illustrated in example embodiment 300, routing platform 110 can include a handover component 325 to administer handoff of a wireless device served by a first femto AP to a second femto AP in the femto enterprise network architecture 100. Handover component 325 can implement hard handoff or soft handoff in accordance at least in part with a set of handover criteria (not shown), which can be configurable by a wireless service provider on an event basis or as a function of time. In an aspect, soft handover can be effected at least in part based on at least one or more RF boundaries, which can be configured through a timing component, as discussed below. In example embodiment 300, memory 349 can retain handover criteria (not shown in FIG. 3).

Routing platform 110 also can enable communication of content(s), or traffic, among a device 102$_3$ served primarily via a network that is part of external network(s) 140, such as one of a non-mobile broadband internet service network, a broadband digital cable network, or a macrocell network and mobile devices served through a femto AP 104$_\lambda$. In an aspect, device 102$_3$ can be an IP television (IPTV) tuner that can receive caller identification information when a call directed to a mobile device 102$_1$ is received by routing platform 110. Such a feature can advantageous to alert a subscriber in a residence wherein the subscriber is associated with the mobile device 1021 and separated there from while the subscriber utilizes device 102$_3$. In another aspect, when the enterprise is a wholesale store, or big-box store, device 102$_3$ can be a voice-over-IP (VoIP) transceiver in a customer service platform which routing platform 110 can connect to a mobile device, e.g., 102$_2$, served through a femto AP, e.g., 104$_2$, within the enterprise femto network system 100 in order to provide customer assistance to a consumer associated with the mobile device. User equipment (UE) that operates within example enterprise femto network system 100 can include almost any or any electronic device that can connect wirelessly to a femto AP or can be linked operationally to a port within routing platform 110. In addition to example UEs provided supra, user equipment can include mobile phones; media players; digital cameras; digital media recorders such as digital video recorders (DVRs); laptop computers; personal digital assistants (PDAs); personal computers; printers; scanners; digital photo frames; navigation device such as a global positioning system (GPS) module; gaming modules; and so forth. Further, it can be appreciated the UEs can be mobile, stationary, or pseudo-stationary, and wireless or tethered.

In an aspect, during internal communication within the enterprise femto architecture 100, routing platform 110 can establish and retain a control link to femto network platform 130, e.g., to gateway node(s) therein, that can be employed by femto network platform 130, via a billing server, to process billing charges; it should be appreciated that billing processing can be effected by an application layer within one of external network(s) 140 such as an IMS network. In example embodiment 300, billing component 335 can allow to establish the control link and convey it to femto network platform 130 to update a billing database associated with a billing server that can apply, for example, different charges for internal communication within the enterprise femto network architecture 100 and external communication with femto network platform 130. Charges associated with internal communication can be lower than charges associated with external communication. The control link also can be retained in a memory, e.g., a buffer, within routing platform 110 such that if a failure occurs in femto network platform 130, internal communication within the mesh femto network 100 can continue uninterruptedly. Retained control data can be transferred to femto network platform 130 for billing purposes when it resumes operation(s).

Example enterprise femto network system 100 also can afford multiple billing schemes associated with a wireless service provider that administers the example femto network architecture 100. In example embodiment 300, billing schemes can be retained in memory 249. In an aspect, the one or more billing schemes can be dictated, at least in part, by access configuration(s) retained in access list(s) 347. In an example billing scheme, the wireless service provider can charge a fixed rate for external communication, for example, when traffic received at the router platform 102 is conveyed to the femto network platform 130 through backhaul link(s) 118, e.g., Iuh interface, whereas internal communication within the example enterprise femto network architecture 100 can be free of charge. It is noted that in such example billing scheme, the wireless service provider can charge a fee directed to operation and maintenance associated with the mesh femto network. In another example billing scheme, the wireless service provider can implement maintenance of the mesh femto network 100 free of charge, but can charge a high rate for external communication with femto network platform 130 and a low rate for internal communication within the mesh femto network. It is to be appreciated that the subject specification is not limited to the aforementioned illustrative billing scheme(s) and most any or any billing scheme can be configured and employed. The wireless service provider can configure or predefine billing charges based at least in part on criteria such as served customer segment, an implemented promotional campaign, marketplace, operational costs, or the like. In example embodiment 300, billing component 335 can configure, at least in part, and implement one or more billing schemes for served traffic within femto enterprise femto network architecture 100 or for traffic delivered to or received from a femto network platform. In addition, billing component 335 can modify such configured billing charges dynamically, e.g., as a function of time, based at least in part on operational conditions such as available network bandwidth, load of one or more deployed femto APs within an enterprise femto network system, volume of traffic manipulated by routing platform 110, or the like.

In an aspect, routing platform 110 can manage different virtual local area network(s) (VLAN(s)) such as one or more of a VLAN for voice or data traffic on user plane; a VLAN for control signaling transported through at least a portion of link(s) 1141, which can be embodied in an Iur interface; a VLAN for control signaling conveyed to femto network platform 130; or the like. In an example, routing platform 110 can enable bandwidth management for the different VLANs.

As illustrated in example embodiment 300, routing platform 110 includes processor(s) 345 configured to confer, and that confers, at least in part, functionality to substantially any or any component within routing platform 110 in accordance with one or more aspects of the subject application. Processor(s) 345 is illustrated as external to the various functional elements or components of routing platform 110; however, processor(s) 345 can be distributed amongst such various functional elements or components. Processor(s) 345 is functionally coupled to each functional element or component and to memory 349 through bus 357, which can be embodied in at least one of a memory bus, a system bus, an address bus, or one or more reference link(s) or interface(s). Processor(s) 345 can store information in, and retrieve information from, memory 349 necessary to operate and/or confer at least in part functionality to each of the components that reside within routing platform 110. The information can include at least one of code instructions, data structures, program modules, or the like.

At least an advantage of example femto enterprise architecture 100 is that it reduces at least one of backhaul network traffic or signaling among provisioned femto APs that are part of the femto enterprise network and a femto network platform, which can include controller node 120.

At least another advantage of example femto enterprise architecture 100 is that routing can be self-healing; for instance, traffic can be routed via an alternative femto AP when an intended femto AP is non-functional or radio communication thereby is otherwise impaired. In addition, data and signaling can be cached or recorded for subsequent utilization to mitigate, at least in part, communication disruption.

At least a further advantage of example enterprise femto network architecture 100 is that it can mitigate utilization of private branch exchange (PBX), or internet protocol (IP)-PBX, resources for intra-premises communication, or communication among a mobile device served through a femto wide radio access network, or a wide area network, which can be mobile or otherwise.

Figure 4:
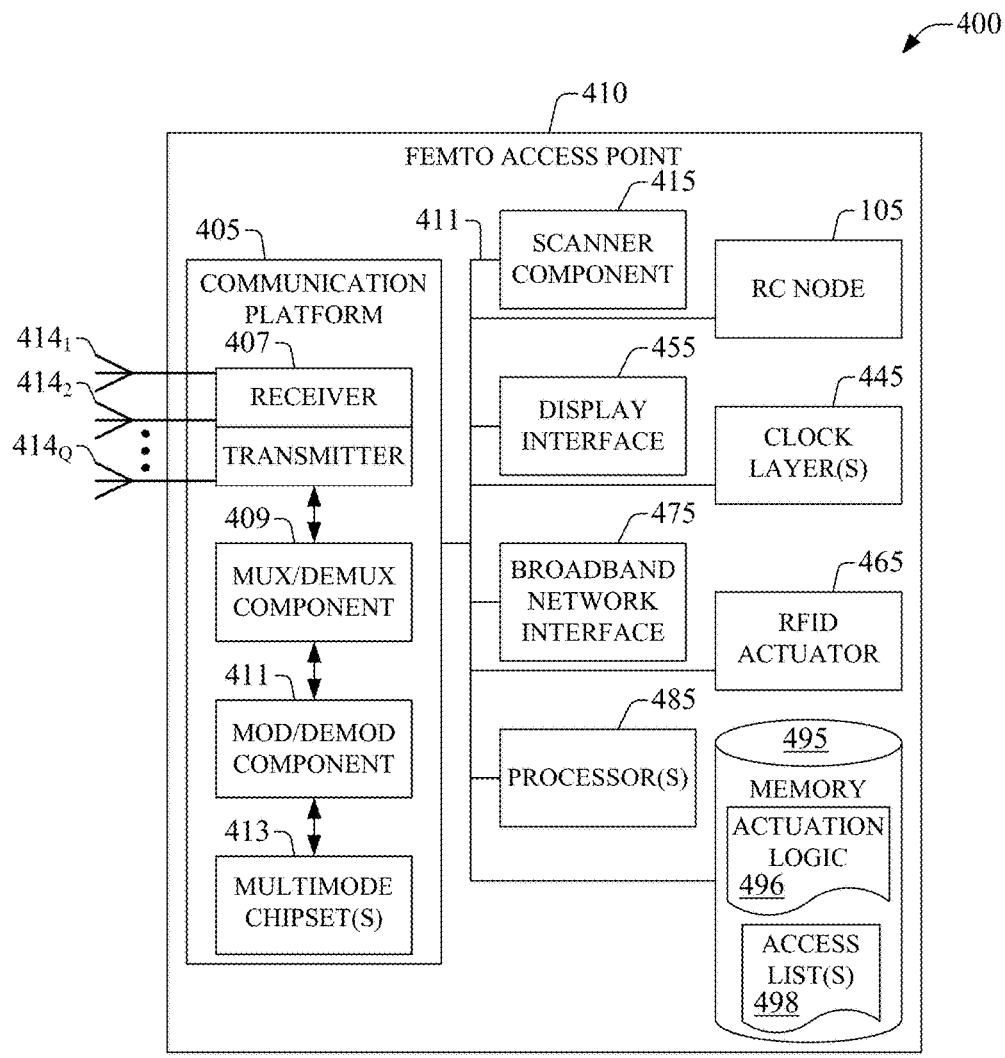
FIG. 4 illustrates an example embodiment of a femto access point that can be deployed in a femto enterprise network in accordance with aspects described herein.

FIG. 4 illustrates an example embodiment 400 of a femto access point that can be deployed in a femto enterprise network in accordance with aspects described herein. Femto AP 410 can embody one or more of femto APs $104_1$-$104_N$. In example embodiment 400, femto AP 410 can receive and transmit signal(s) from and to wireless devices like femto access points, access terminals, wireless ports and routers such as routing platform 110 and port(s) therein, or the like, through a set of antennas $414_1$-$414_Q$, with Q a natural number. The antennas $414_1$-$414_Q$ are part of communication platform 405, which comprises electronic components and associated circuitry that provide for processing and manipulation of received signal(s) and signal(s) to be transmitted. The electronic components and circuitry can include a set of one or more chipsets, e.g., multimode chipset(s) 413, that enable at least in part at least one of decoding, or deciphering, signal(s) conveyed to femto AP 410 in various disparate radio technologies, or coding of signal(s) delivered from femto AP 410 in accordance with various radio technology standards. In an aspect, communication platform 405, via at least in part multimode chipset(s) 413, can decode (i) GPS signaling such as timing messages generated, for example, by one or more deployed global navigation satellite systems (GNNSs) and relayed to femto AP 410 through a routing platform, e.g., 110 in accordance with aspects described herein; or (ii) signal(s) received from a radio frequency identification (RFID) tag upon actuation thereof.

In an aspect, communication platform 405 includes a receiver/transmitter 407 that can convert signal from analog to digital upon reception, and from digital to analog upon transmission. In addition, receiver/transmitter 407 can divide a single data stream into multiple, parallel data streams, or perform the reciprocal operation. Coupled to receiver/transmitter 407 is a multiplexer/demultiplexer 409 that facilitates manipulation of signal in time and frequency space. Electronic component 409 can multiplex information (data or traffic and control or signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 409 can scramble and spread information (e.g., codes) according to substantially any code known in the art; e.g., Hadamard-Walsh codes, Baker codes, Kasami codes, polyphase codes, and so on. A modulator/demodulator component 411 also is a part of communication platform 405, and can modulate information according to multiple modulation techniques, such as frequency modulation, amplitude modulation (e.g., M-ary quadrature amplitude modulation (QAM), with M a positive integer), phase-shift keying (PSK), and the like. In an aspect, multimode chipset(s) 413 can configure and enable mux/demux component 409 and mod/demod component to operate in accordance with protocols or standards associated various radio technologies. Processor(s) 485 also is functionally connected to communication platform 405 and can enable operations on data (e.g., symbols, bits, or chips) for multiplexing/demultiplexing, such as effecting direct and inverse fast Fourier transforms or Hadamard transforms; or modulation/demodulation of data streams.

Femto access point 410 also includes RC node 105, which can allocate radio resources, e.g., resource blocks, to a mobile device served through femto AP 410, and schedule traffic among mobile devices, and device with wireless capability, served via femto AP 410. In an aspect, RC node 105 can schedule traffic in accordance with at least one of semi-persistent scheduling, round robin, or proportional fair scheduling. Consistent with allocated radio resources, RC node 425 can select format(s) of data packet(s) and management packet(s) for traffic and signaling exchange amongst femto AP 410 and a served mobile device. In addition, RC node 105 can select a radio technology and modulation formats and coding schemes compatible therewith. In an aspect, RC node 105 can configure operation of femto AP 410 in multiple-input multiple-output (MIMO) mode of operation. Moreover, RC node 105 can determine and configure transmit power for communication effected via femto AP 410. Furthermore, RC node 105 can configure one or more of antennas $414_1$-$414_Q$ in order to attain directionality of EM radiation employed for communication, or to shape coverage area in the vicinity of femto AP 410, which can mitigate of dead-spots or weakly covered regions. Traffic and signaling can exchanged with a routing platform, e.g., 110, through RC node 105.

In embodiment 400, scanner component 415 can decode received wireless signals and thus determine at least an index that identifies a mobile device (e.g., $102_1$) attached to, or that attempts attachment to, femto AP 410 can be extracted and access can be granted or denied based at least in part on access list(s) 498. In addition, scanner component 415 can decode wireless signal(s) received as part of time-of-flight (TOF) measurements that can be employed to estimate range of a mobile device or device with wireless capability from femto AP 410. In an aspect, femto AP 410 can receive signaling that configures clock layer(s) 445 in order to conduct TOF measurements; configuration can include selection of a clock source (not shown) within clock layer(s) 425. It is noted that clock layer(s) 445 also can be configured to relay timing messages or timing information generated through an external clock. TOF measurements assess wireless signal propagation timing between a femto AP and an apparatus with wireless capability(ies); the TOF measurements can include at least one of round trip time (RTT) measurements, time or arrival (TOA) measurements, time difference of arrival (TDOA) measurements, angle of arrival (AOA) measurements, or the like.

It is noted that through at least in part communication platform 405, and multimode chipset(s) 413 therein, scanner component 415 can survey wireless signal(s) within a set of EM frequency bands that can include all EM frequency bands licensed by the service provider (e.g., personal communication services (PCS), advanced wireless services (AWS), general wireless communications service (GWCS), and so forth), all unlicensed frequency bands currently available for telecommunication (e.g., the 2.4 GHz industrial, medical and scientific band or one or more of the 5 GHz set of bands), and all EM frequency bands in operation and not licensed to the service provider. In addition, scanner component 415 can survey wireless signal(s) over a configurable and upgradable set of radio technologies that includes one or more of the following Wi-Fi, BlueTooth, IS-95, WiMAX, 3GPP2 UMB, Enhanced GPRS, 3GPP UMTS, 3GPP LTE, HSPA, HSDPA, HSUPA, or LTE Advanced. Processor(s) 485 can enable communication platform 405 to switch amongst radio technologies (e.g., IS-95, WiMAX . . . ) in order to effect telecommunication and enable a scan in accordance with configured demodulation and demultiplexing protocols associated with a radio technology; instructions necessary for implementation of such protocols can reside in memory 495. Such radio technology agility can afford to serve mobile devices, e.g., $102_1$ or $102_2$, which operate in disparate radio technologies, or collect pilot signal(s) modulated and coded in accordance to various technologies.

To conduct a scan, scanner component 415 exploits at least in part communication platform 405 and electronic components therein. In an aspect, scanner component(s) 212 can configure transceiver 407 to collect signal in a specific frequency carrier, e.g., frequency channel. Such configuration can allow determination of uplink (UL) carrier frequency, or channel number, associated with communication of mobile device(s) within the enterprise femto network 100 and in the vicinity of femto AP 410; and carrier frequency of downlink (DL) of disparate femto APs in the vicinity of femto AP 410. RC node 425 can deliver information that identifies carrier frequencies extracted through scanning the wireless environment of femto AP 410. Such carrier-frequency information is delivered to a routing platform, e.g., 110, which can aggregate it to form a carrier-frequency map of telecommunications within the coverage area of an enterprise femto network.

Scanner component 415 also can gather data on uplink (UL) signal strength and quality associated with a served mobile device, e.g., $102_1$, to effect, at least in part, handover from femto AP 410 to a disparate target femto AP. To at least that end, scanner component 415 can gather UL sounding signal(s) and analyze such signal(s) to determine DL channel quality or strength; analysis can be enabled at least in part via processor(s) 485. In an aspect, signal strength can be determined through received signal strength indicators (RSSIs) or received signal code power (RSCP), while quality can be assessed through metrics such as signal-to-noise ratio (SNR), signal-to-noise-and-interference ratio (SNIR), or energy per chip over total received power ($E_c/N_0$).

In addition, femto AP 410 includes display interface 455, which can render functions that control functionality of femto AP 410 or reveal operational conditions thereof. In addition, display interface 1812 can include a screen to convey information to an end user. In an aspect, display interface 455 can be embodied in a liquid crystal display (LCD), a plasma panel, a monolithic thin-film based electrochromic display, or the like. Moreover, display interface 455 also can include a component (e.g., speaker(s)) that facilitates communication of aural indicia, which can be employed in connection with messages that convey operational instructions to an end user or consumer. Display interface 1812 also can enable data entry (e.g., through a linked keypad or via touch gestures), which can allow femto AP 410 to receive external commands, such as restart operation, flush a memory or buffer, configure an access list, etc.

Broadband network interface 475 enables connection of femto AP 410 to a routing platform, as described herein, through broadband link(s) such as link(s) $114_\lambda$, which can enable incoming and outgoing data and signaling flow. In an aspect, broadband network interface 475 can include a port component with substantially the same or the same functional aspects or features as port component 315. Broadband network interface 1814 can be internal or external to femto AP 1805, and it can utilize display interface 1812 for at least one of end-user interaction or status information delivery. Processor(s) 485 can configure at least in part operation of one or more port(s), e.g., switching voltages in a dry contact or assignment of a logical address such as an IP address to a port, that can reside within broadband network interface 475. It is noted that RC node 425 can conduct at least part of the assignment of logical address(es) to a port within broadband network interface.

Femto AP 410 also includes an RFID actuation component 465, also termed herein RFID actuator 465, which can convey through communication platform 405 specific control packets within a pilot signal in order to stimulate an RFID tag and retrieve information therein by decoding RF packet(s) received from the RFID tag in response. Actuation protocol(s) and code sequence hypotheses for decoding information retained in an RFID tag can be included in actuation logic 496 stored in memory 495.

Memory 495 can retain data structures, code instructions and program modules, or substantially any type of software or firmware; system or device information; code sequences hypotheses, and modulation and multiplexing hypotheses; spreading and pilot transmission; femto AP floor plan configuration; and so on. Additionally, memory 495 can retain content(s) (e.g., multimedia files, subscriber-generated data); security credentials (e.g., passwords, encryption keys, digital certificates, biometric reference indicators like voice recordings, iris patterns, fingerprints); or the like.

Processor(s) 485 is functionally connected, through bus 411 to component(s), platform, interface(s), layer(s) and substantially any or any functional element that resides within femto AP 410. Bus 411 can be embodied in at least one of a memory bus, a system bus, an address bus, or one or more reference link(s) or interface(s). In an aspect, processor(s) 485 is functionally coupled, e.g., via a memory bus within at least a portion of bus 411, to memory 495 in order to store therein and retrieve there from information to operate or confer functionality to the components, platform, interface(s), layer(s) and substantially any or any functional element that reside within femto AP 410.

Figure 5:
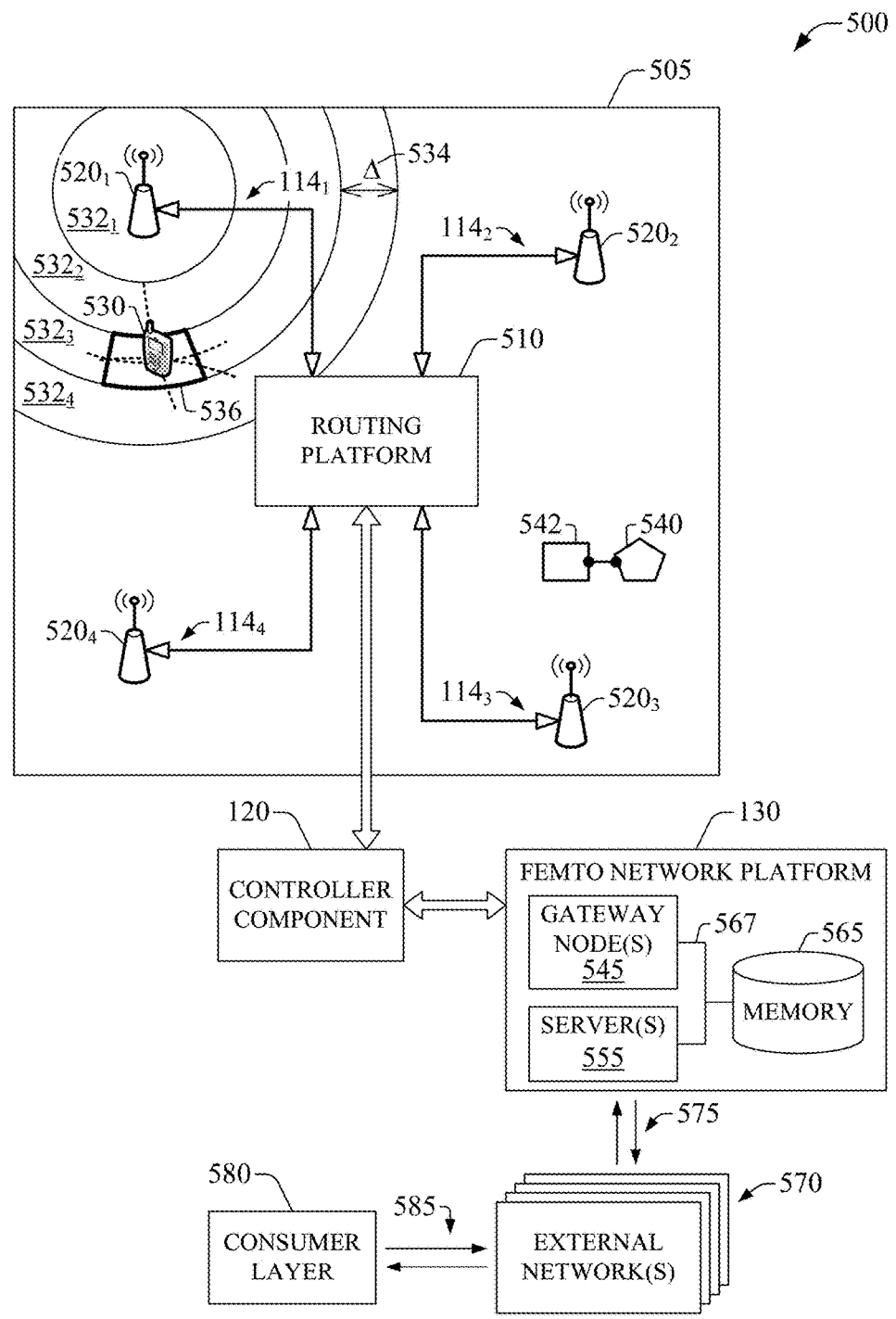
FIG. 5 illustrates a diagram of an example embodiment of a femto enterprise network architecture that enables collection of location data in accordance with aspects of the subject embodiments.

FIG. 5 illustrates a diagram of an example embodiment 500 of an enterprise femto network that enables collection of location data and utilization thereof in accordance with aspects of the subject application. Location data can include location estimate(s) of a mobile device or an entity linked to an apparatus with wireless capability. Routing platform 510 can configure, e.g., synchronize, a clock layer in each of femto APs $520_1$-$520_4$, and control, e.g., trigger or initiate, terminate, etc., time-of-flight (TOF) measurements of propagation timing of wireless signal(s), such as control signal(s), that can enable estimate(s) of distance of a mobile device (e.g., mobile 430) or an apparatus with wireless capability (e.g., 542) from one or more of femto APs $520_1$-$520_4$. Such distance, or range, estimates can allow routing platform 510 to resolve a location estimate for mobile device 530 or an apparatus 542 with wireless capability. As an example, routing platform 510 can triangulate a position of mobile device 530—dotted lines near and through mobile 530 indicate triangulation effected through femto APs $520_1$, $520_2$, and $520_3$. In addition, routing platform 510 can triangulate a position of apparatus 542 and thus produce an estimate of the position of an entity 540 linked spatially with the apparatus; for instance, the entity can be a vehicle and a navigation device thereof can be apparatus 542. A memory within routing platform 510 can retain criteria to determine whether the entity 540 spatially linked to the apparatus 542. It is noted that in a femto enterprise network that is deployed within multiple coverage areas, see example embodiment 250, a location estimate can be generated through range estimates generated via timing measurements performed by at least four femto APs. As an illustration, TOF measurements performed at least in part via femto AP $520_1$ can result in a set of TOF-bands or fringes $532_1$-$532_4$. The width Δ 532 of a TOF band is determined primarily through a timing advance (TA) established by a clock source that determines chip structure linked to the pilot wireless signal(s). It is noted that while not displayed, other femto APs also can generate a TOF-band structure as the one related to femto AP $520_1$.

Location estimate(s) can be conveyed to a consumer layer 580, which can utilize the location estimate(s) as part of a navigation or location-based service. Routing platform can deliver the location estimate(s) as at least one of a short message service (SMS) communication, a multimedia message service (MMS) communication, an unstructured supplementary service data (USSD) message, an email communication, or an instant message. In addition, location estimate(s) can be delivered through lower-level signaling such as a set of one or more bits in a packet header or in one or more control frames. In an aspect, delivery of a location estimate proceeds at least in part as described supra in connection with communication of content to femto network platform 130. A gateway node that is part of gateway node(s) 545 can communicate the location estimate to a gateway node within the external network(s) 570, which can relay the location estimate to a serving node therein in order to delivery the location estimate to the consumer layer 580. In an aspect, external network(s) 570 can be an IMS network or almost any or any packet-switched network.

Consumer layer 580 can include one or more devices operated by one or more subscribers or prosumers. As an example, consumer layer can be a mobile device associated with an owner or leaser of entity 540. In a scenario, coverage area 505 can be a parking lot, either multi-floor or single-floor, and entity 540 can be a vehicle for which routing platform 510 generates a location estimate at the time the vehicle is parked. The location estimate for the parked vehicle can be provided to consumer layer based upon various criteria such as when a registered mobile device re-enters the parking lot after the vehicle has been parked. Alternatively or additionally, the location estimate can be supplied upon demand from a subscriber associated with the vehicle and that operates a mobile device, demand for the location estimate of the vehicle can be effected by dialing a specific phone number extension for routing platform 510, delivering a SMS message or an email message, or a USSD code. As another example, consumer layer 580 can be equipment of a law enforcement agency and location estimate(s) can be supplied as part of the Communications Assistance to Law Enforcement Act (CALEA). In a scenario, a black list consisting of one or more unique identifiers for respective wireless devices can be supplied through an interface (not shown) in consumer layer 580. Routing component 510 can retain the black list in a memory, e.g., in access list(s) in example embodiment 600. When a black listed mobile device attempts attachment to a femto AP that is part of femto enterprise network, routing component 510 can alert the law enforcement equipment in consumer layer 580, for example, by delivering the location estimate of the detected blacklisted mobile device. In addition or as an alternative, when the blacklisted mobile device is detected, routing platform 510 can track location of the blacklisted mobile device within coverage area 505.

In an aspect of the subject application, to utilize high pilot transmit power to increase the number of femto APs that generate range estimates to implement triangulation, routing platform 510 can configure delivery and transport of control signal(s) employed at least in part in TOF measurements in channel(s), or frequency carrier(s), disparate from those utilized for traffic. It should be appreciated that utilization of dedicated carriers for triangulation that are disparate, e.g., orthogonal, to carriers employed for voice and data can mitigate interference that may be incurred through generation of location estimates. As an example, femto APs can convey pilot signal(s) for TOF measurements in a carrier within unlicensed electromagnetic (EM) radiation bands, whereas the femto APs can convey voice and data in a channel within a licensed EM radiation band.

Figure 6:
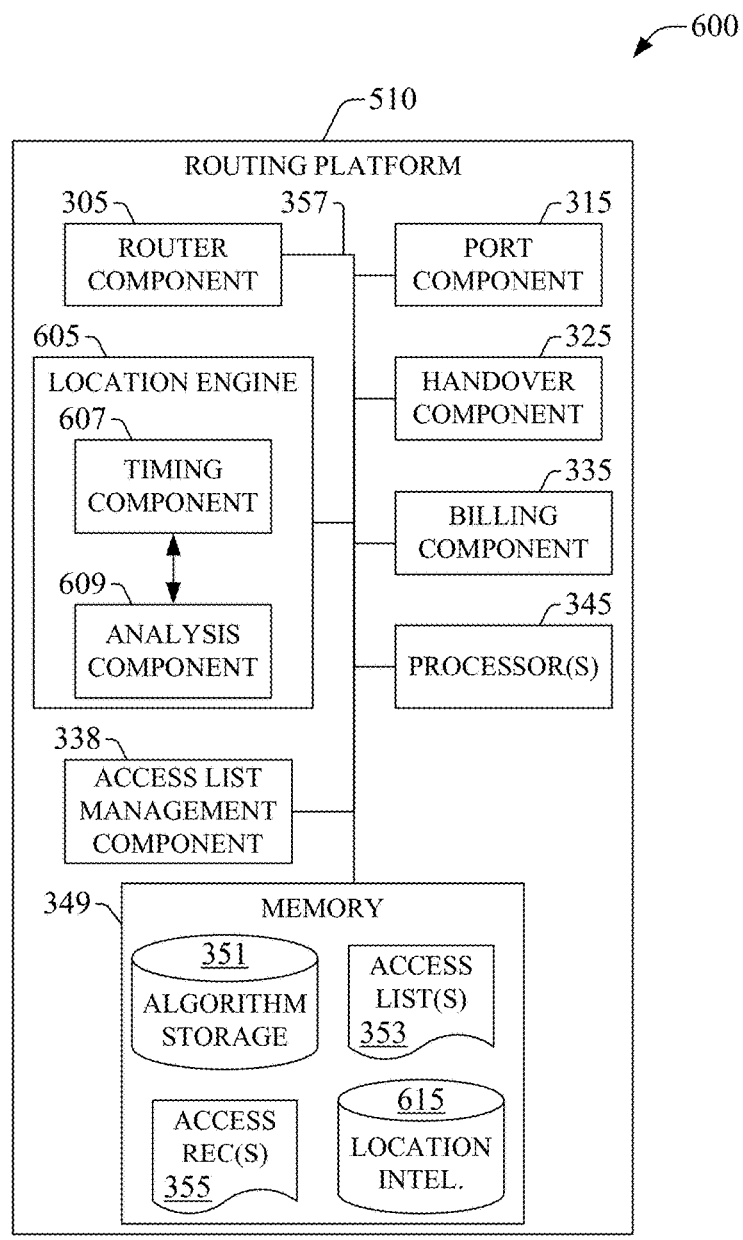
FIG. 6 illustrates a block diagram of an example embodiment of a routing platform that is part of an enterprise femto network architecture in accordance with aspects disclosed herein.

In an example embodiment of routing platform 510, illustrated in FIG. 6, location engine 605 can generate location estimate(s) through triangulation. To at least that end, timing component 607 enable routing component 510 to configure and control the TOF measurements, and analysis component 609 exploits data collected through the timing measurements to compute a location estimate through triangulation; algorithm storage 351 can retain code instructions that, when executed, implement triangulation. In an aspect, analysis component 419 can select a propagation model, retained within algorithm storage to include stochastic aspects of propagation such as multipath or other scattering, shadowing, or path loss, in a computation of a location estimate. Location estimate(s) can be retained in location intelligence 615.

Routing component 510 also can control complexity of timing configuration(s), e.g., selection of clock sources adequate for coarse resolution or fine resolution of location estimates, based at least in part on a hierarchy of resolution of generated location estimate(s) and aspects of an associated location service. (1) For specific content routing, e.g., offloaded content from a wide area network (WAN) to the enterprise femto coverage area 505, association of a unique identifier (ID) for the serving femto AP with mobile device 530 or a unique ID thereof can be sufficient; one or more of external network(s) 570 can embody the WAN. In example embodiment 600, location intelligence 615 can include a mapping of unique femto ID(s) linked to each provisioned femto AP and a deployment configuration of femto APs such as $520_1$-$520_4$. (2) To implement, at least in part, location-based handover from a first femto AP to a second femto AP, routing component 510 can select a clock source that provides a TOF-band width $\Delta$ 534 that is smaller than a characteristic spacing $\Delta'$ among provisioned femto APs that can enable the handover; for instance, $\Delta/\Delta'$=0.1 can be utilized. In example embodiment 600, selection of the clock source can be implemented at least in part through timing component 607. As an example, $\Delta'$ can be determined as an average of nearest-neighbor distances among femto APs. In addition, azimuth resolution can be implemented to further refine a location estimate to a specific tile in order to distinguish among substantially equally or equally close femto APs that are candidate for handover. Azimuth-resolved timing measurements, e.g., AOA in combination with RTT, can determine a tile such as 536 (indicated with thick lines) rather than a TOF-band, e.g., $532_3$. It should be appreciated that a set of two or more antennas in a femto AP, such as $520_1$, can be configured, by routing component 510, and employed to afford azimuth resolution; timing component 607 can enable at least in part such configuration. (3) For tracking of a mobile device 530 or an entity 540 associated to an apparatus 540 with wireless capabilities, finer resolution is necessary in order to enable triangulation of the mobile device 530 or the apparatus 540 to extract a location estimate that is highly accurate, e.g., with a resolution of the order of 1 m. To allow high-resolution triangulation, routing platform 510 can select a clock source that provides timing advance (TA) such that $\Delta$ 534 is sufficiently narrow, e.g., 1 m, to afford highly-resolved triangulation. In example embodiment 600, timing component 607 can select the clock source. Location estimate(s) can be retained in a memory that is part of routing component 510, and can be conveyed within the bounds of the coverage area of the enterprise femto network or outside such bounds.

Routing component 510 can exploit artificial intelligence (AI) or machine learning methods to infer (e.g., reason and draw a conclusion based upon a set of metrics, arguments, or known outcomes in controlled scenarios) a satisfactory or optimal timing resolution to generate a location estimate with a spatial resolution suitable to a predetermined location service. Inference can be based at least in part upon cost-utility analysis that determines the trade off between signaling cost, e.g., clock selection, triggering signaling, carrier selection and communication, versus the benefit of accurately knowing position of mobile device. In embodiment 600, timing component 607 can implement the cost-utility analysis. Machine learning methods can be retained in algorithm storage 351.

Artificial intelligence or machine-learning techniques typically apply advanced mathematical algorithms—e.g., decision trees, neural networks, regression analysis, principal component analysis (PCA) for feature and pattern extraction, cluster analysis, genetic algorithm, or reinforced learning—to a data set. In particular, handover component 254 or any component(s) therein can employ one of numerous methodologies for learning from data and then drawing inferences from the models so constructed. Such methodologies can be retained in memory 260. For example, Hidden Markov Models (HMMs) and related prototypical dependency models can be employed. General probabilistic graphical models, such as Dempster-Shafer networks and Bayesian networks like those created by structure search using a Bayesian model score or approximation can also be utilized. In addition, linear classifiers, such as support vector machines (SVMs), non-linear classifiers like methods referred to as "neural network" methodologies, fuzzy logic methodologies can also be employed. Moreover, game theoretic models (e.g., game trees, game matrices, pure and mixed strategies, utility algorithms, Nash equilibria, evolutionary game theory, etc.) and other approaches that perform data fusion, etc., can be exploited.

Figure 7A:
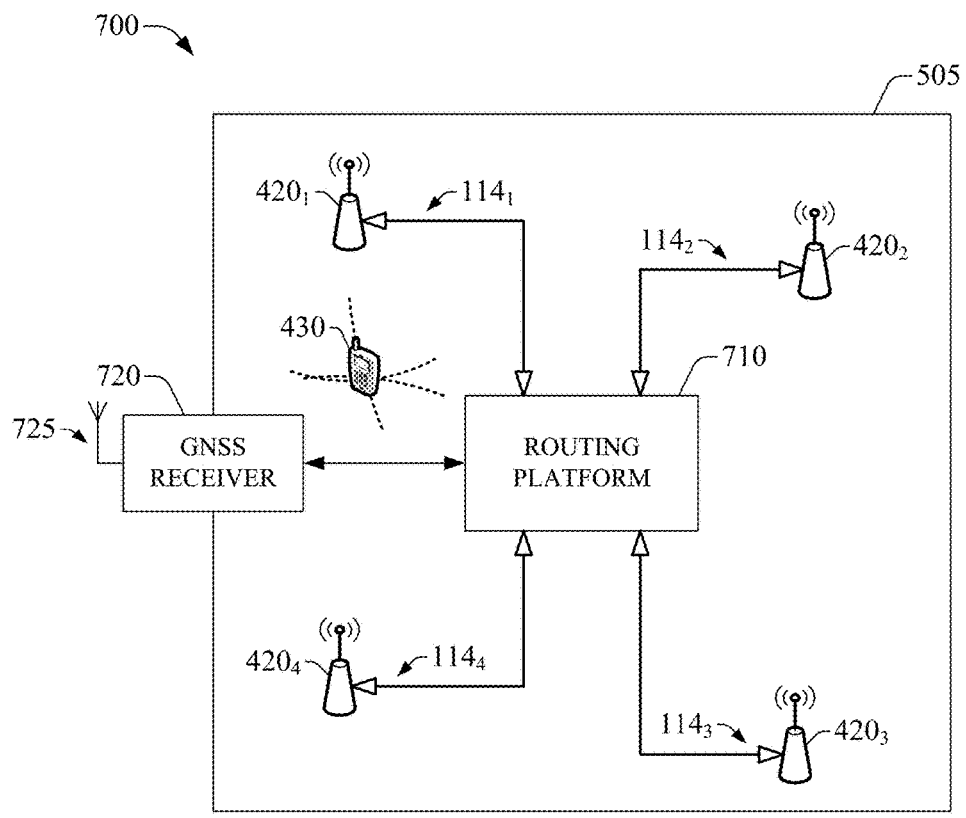
FIGS. 7A and 7B illustrates diagrams of example embodiments of a femto enterprise network architecture that enables collection of location data of a mobile in accordance with aspects of the subject embodiments.

FIG. 7A illustrates a diagram 700 of a femto enterprise network architecture that enables collection of location data of a mobile in accordance with aspects of the subject embodiments. Routing platform 610 receives timing messages, or timing reference(s), from a global navigation satellite system (GNNS) receiver component 620, also termed herein as GNSS receiver 620, which can collect timing messages from one or more satellites through one or more antenna(s) 625. In an aspect, GNSS receiver 620 can be exposed to open sky, and at least a part thereof can reside within a NID, e.g., NID $210_2$. Femto APs $520_1$-$520_4$ can time-stamp control message(s) or sounding signal(s) conveyed by mobile device 430 and thus generate range estimate(s) that allow generation of location estimates based at least in part on triangulation.

Figure 7B:
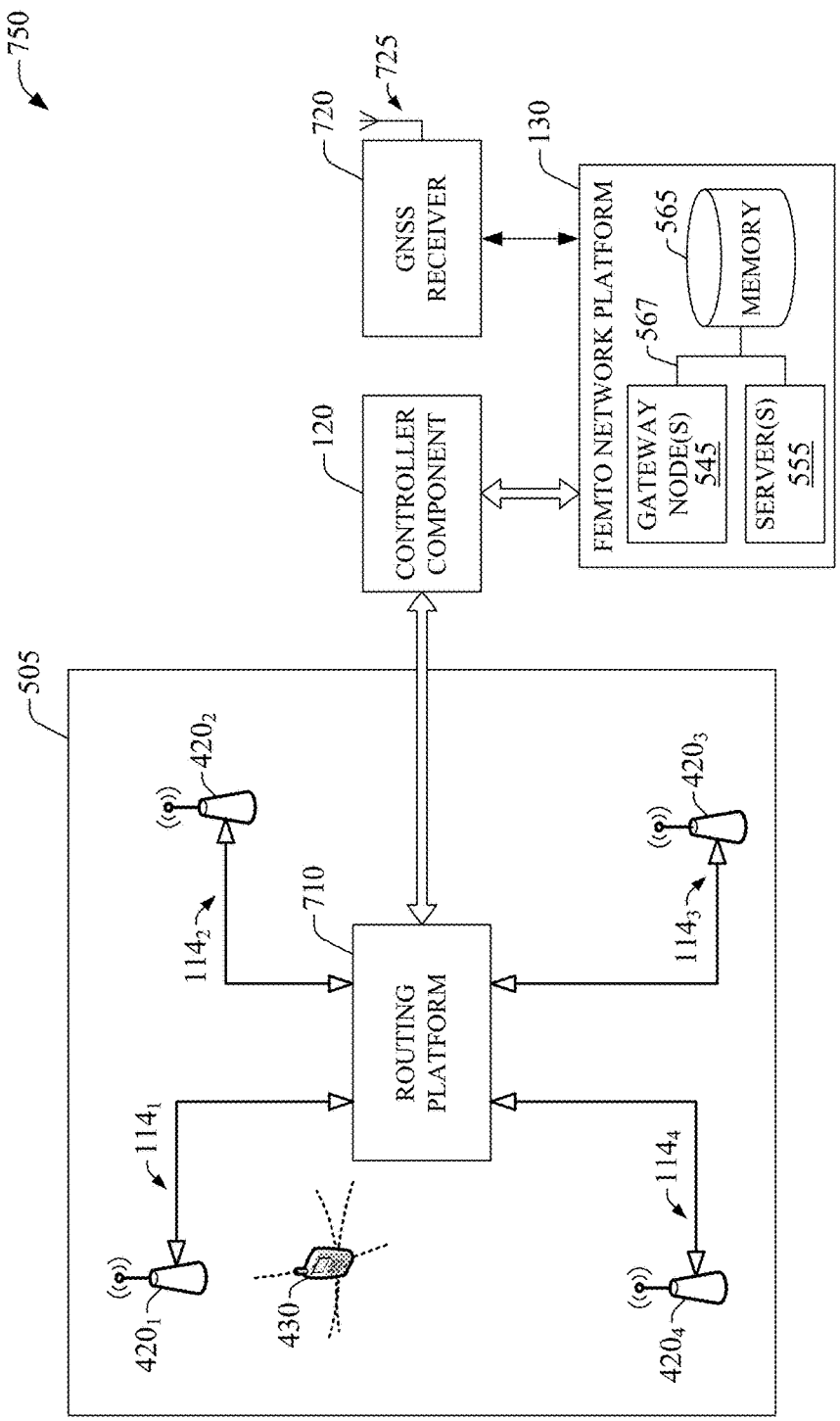

FIG. 7B displays a diagram of an embodiment 650 of a femto enterprise network architecture that enables collection of location data of a mobile in accordance with aspects of the subject embodiments. In an aspect, timing message(s) GNSS receiver 620 is functionally connected to femto network platform 660, which can relay the timing message(s) via gateway node(s) 545. It should be appreciated that GNSS receiver 620 can be part of assisted GPS (AGPS) infrastructure provided by a network operator that administer femto network platform 660 and femto APs $520_1$-$520_4$.

Figure 8:
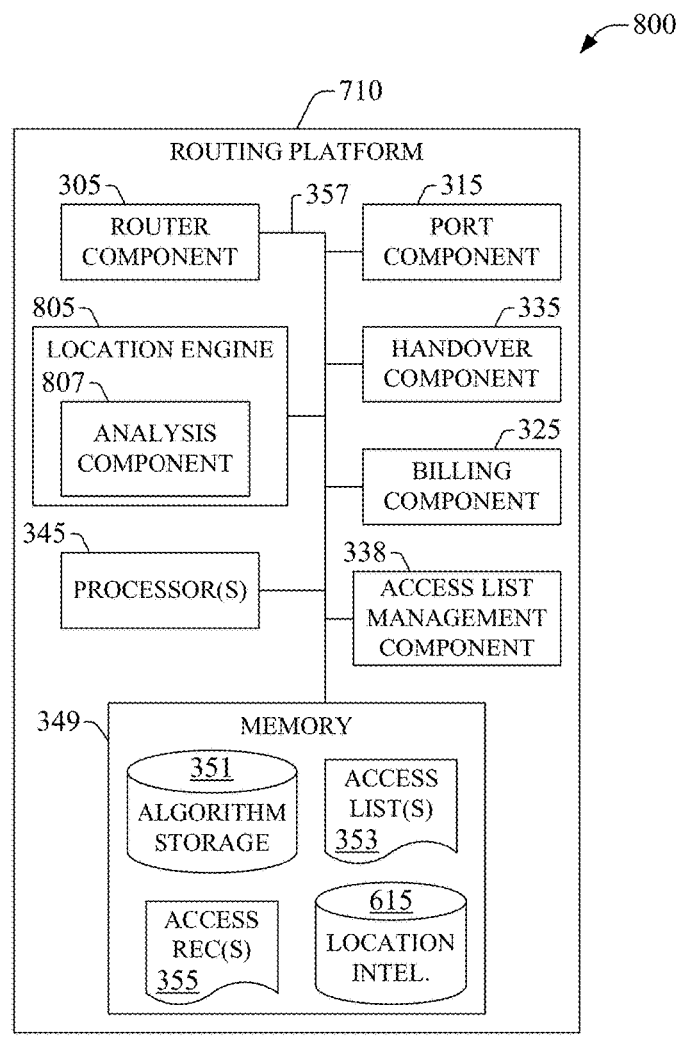
FIG. 8 illustrates an example embodiment of a routing platform that can be part of an enterprise femto network architecture in accordance with aspects of the disclosure.

In embodiments 700 and 750, routing platform 710 exhibits less complexity than routing platform 510. As illustrated in FIG. 8, location engine 805 does not include a timing component, but rather location engine 805 operates as a pass-through of timing message(s) received from GNSS receiver 720. Analysis component 807 can operate in substantially the same manner as analysis component 809. In particular, analysis component 807 can receive timing signaling, e.g., records of time-stamped messages, originated at a plurality of femto APs and utilize such signaling to perform triangulation and associated location estimate(s) of mobile device 530.

Figure 9:
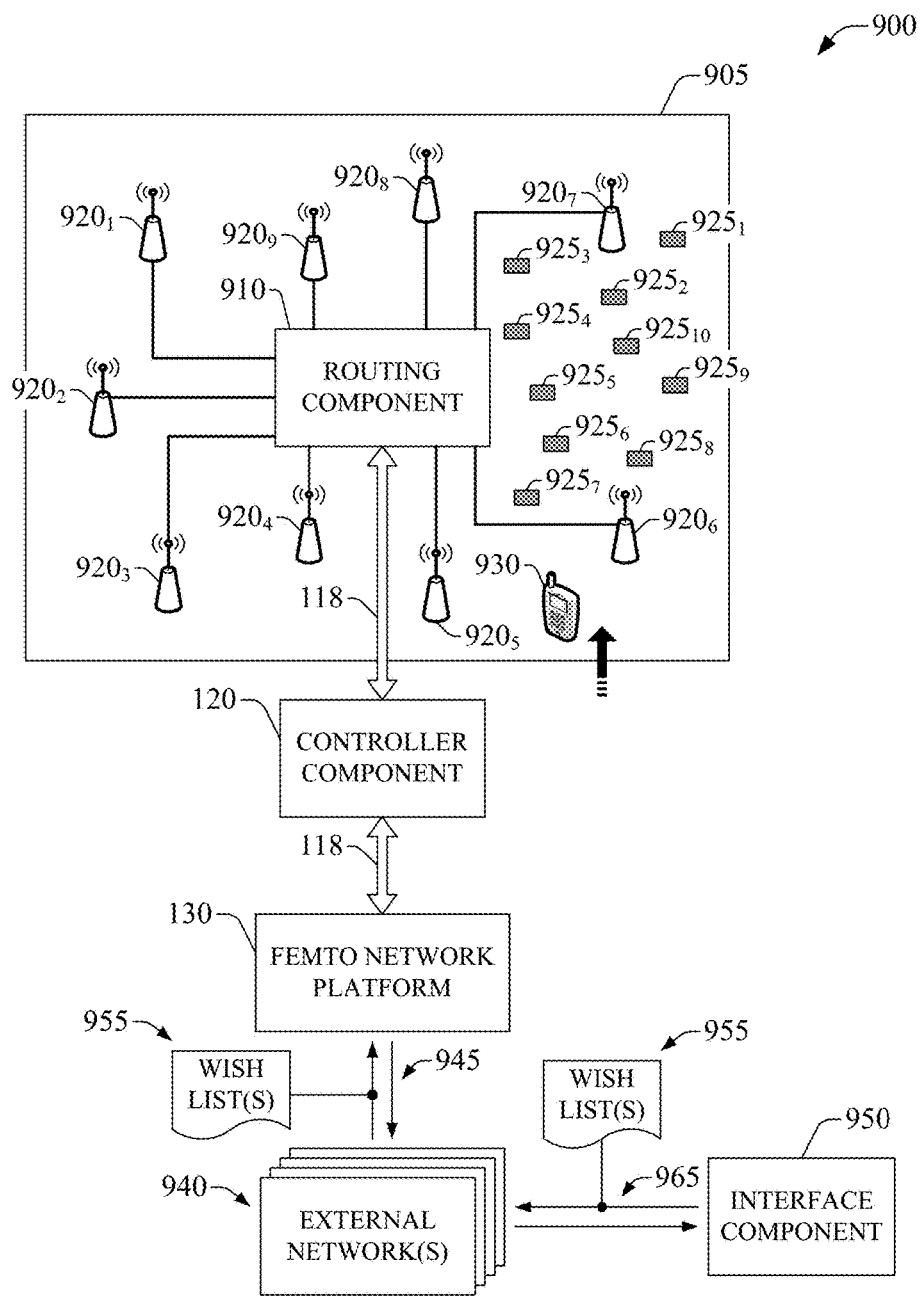
FIG. 9 represents an example system that enables customized item navigation at least in part through an example enterprise femto network in accordance with aspects described herein.

FIG. 9 represents an example system 900 that enables customized item navigation at least in part through an example femto network architecture in accordance with aspects described herein. Interface component 950 enables a subscriber or prosumer to configure wish list(s) 955 of items to be identified within a remote site 905 that includes an enterprise femto network architecture. Interface component can deliver wish list 955 through link(s) 965, which can be broadband backhaul link(s), to external network(s) 940. For instance, external network(s) can be a broadband non-mobile network that provides internet service. External network(s) 940 can convey wish list(s) 955 to femto network platform 130, which can relay the wish list(s) 955 to controller node 120—e.g., a radio network controller in a 3GPP UMTS telecommunication architecture.

Controller component 120 can deliver the wish list(s) 955 to routing component 910, which can generate a set of locations of item(s) listed in wish list(s) 955 for which RFID tag(s), e.g., $925_1$-$925_{10}$, are contacted to the item(s). Accordingly, the generated set of location estimate(s) can be mapped to the tagged item(s). In an aspect, routing component 910 can resolve location estimates for the item(s) in the wish list(s) 955 in response to entrance, illustrated with a black arrow FIG. 9, of mobile device 930 into the coverage area 905 of the enterprise femto network and attachment of the mobile device 930 to a femto AP therein; wherein mobile device 930 is linked to the subscriber or prosumer that configured the wish list(s) 955. Alternatively or additionally, routing component 910 can generate the set of location estimate(s) in accordance with at least one of a schedule, retained as part of location intelligence, e.g., 615, within routing platform 910; or an event such as a relocation or RFID tags $925_1$-$925_{10}$ within coverage area 905.

Figure 10:
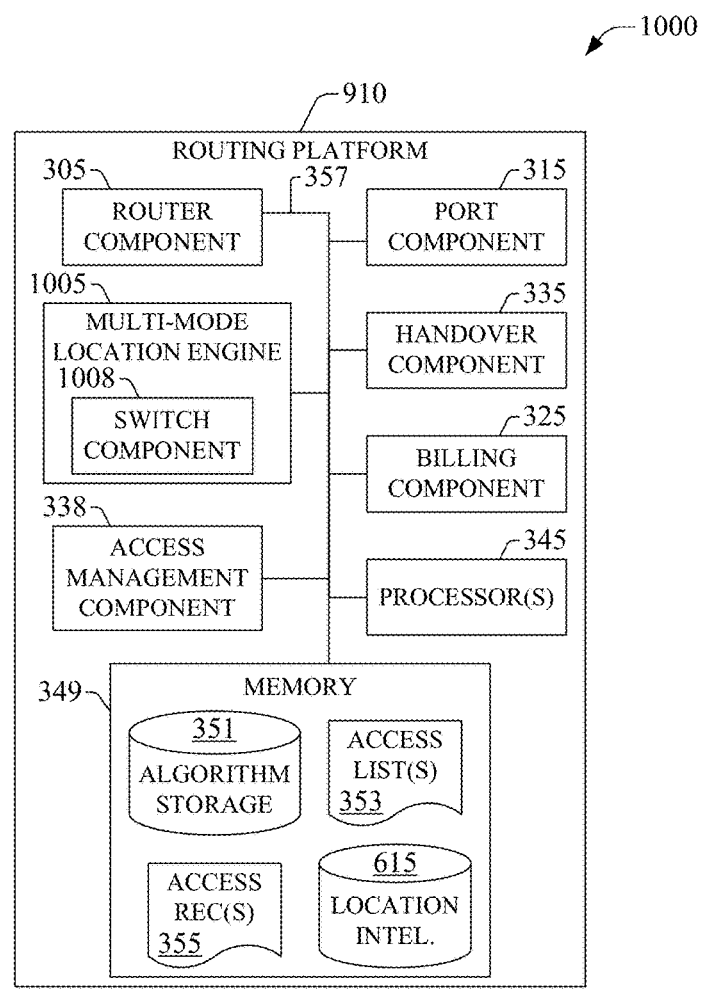
FIG. 10 illustrates an example embodiment of a routing platform that can operate within an enterprise femto network in accordance with aspects described herein.

Generation of location estimates for items within wish list 955 can be accomplished at least in part through RFID actuator 465, which can remotely probe the RFID tag(s) $925_1$-$925_{10}$ via pilot signal(s) delivered through a set of femto APs, e.g., $920_6$, $920_7$, and $920_8$. Probing of RFID tag(s) can enable triangulation of each tag and thus generation of respective location estimate(s); triangulation can be implemented via a location engine within routing component 910 in accordance at least in part with aspects described herein. In an example embodiment 1000 of routing platform 910, illustrated in FIG. 10, a multi-mode location engine 1005 can perform triangulation of location of an RFID tag. Multi-mode location engine 1005 includes a switch component 1008 that can toggle functionality of the multi-mode location engine based at least in part on timing capabilities of routing platform 910. In an aspect, when routing platform 910 can supply timing configuration to one or more femto APs, switch component 1008 can configure operation of multi-mode location engine in a mode of operation substantially the same or the same as location engine 605. Alternatively, when routing platform 910 exploits external timing information to configure timing of a set of femto APs that provide wireless service to the enterprise femto network, switch component 1008 can set multi-mode location engine to operation that is substantially the same or the same as location engine 805. It should be appreciated that that multi-mode location engine 1005 includes analysis component 807 (not shown in FIG. 10), and timing component 607 and analysis component 609 (neither one shown in FIG. 10).

Femto AP(s) $920_1$-$920_9$ can include RFID actuation logic, e.g., 496, retained in a memory therein, that enables delivery of a pilot signal to an RFID tag and performs TOF measurement(s) to collect timing data and allow triangulation. The pilot signal can be conveyed in a frequency carrier disparate from a band of EM radiation employed for communication through the femto AP(s); thus, RFID tag(s) $925_1$-$925_{10}$ can be interrogated without inflicting substantive interference. Femto AP(s) also can decode information retained in the interrogated RFID tag(s), and relay such information to routing platform 810, which can perform at least one of the following: retain the information in memory, e.g., memory 349, or adjust the information. It is noted that the information can include at least one of product identification or pricing point of the product. In an aspect, adjustment of information can be directed to adjusting pricing of the item(s) identified through the probed RFID tag(s).

Figure 11:
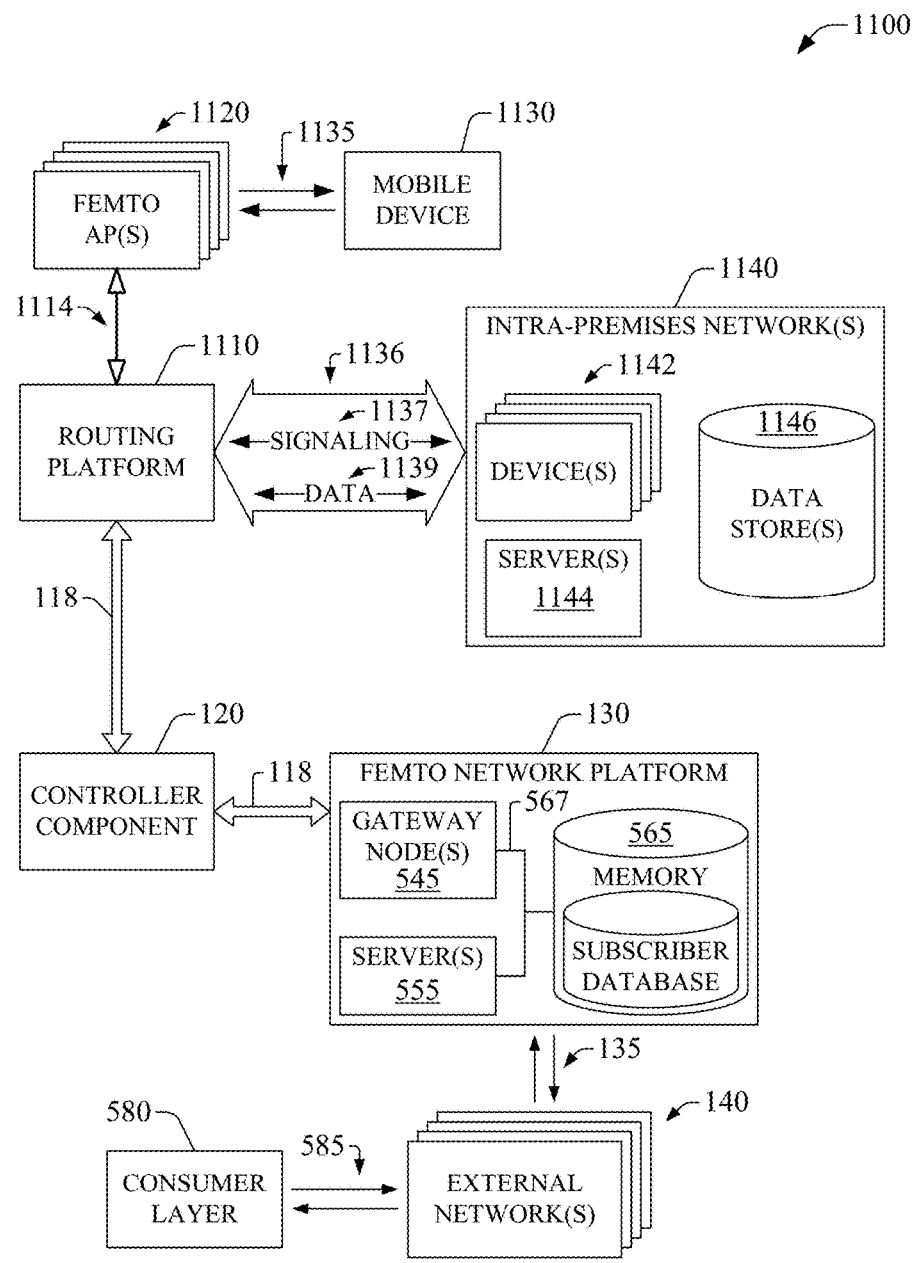
FIG. 11 is a block diagram of an example system that enables intra-premises networking through an enterprise femto network in accordance with aspects described herein.

FIG. 11 is a block diagram of an example system that enables intra-premises networking through an enterprise femto network in accordance with aspects described herein. Routing platform 1110 is functionally linked through a set of one or more links 1114 to a set of respective one or more femto APs 1120, which span a coverage area that can be a single-floor or multi-floor confined or nearly confined space. Based on at least one of location within the coverage area or access privilege(s) or right(s) established through access list(s), e.g., 353 or 498, a femto AP within the set of femto APs 1120 can serve mobile device 1130 through wireless link 1135. Routing platform 1110 also is functionally connected to intra-premises network(s) 1140 via link(s) 1136, which can be reference link(s) or interface(s), or conventional wired or wireless link(s). It is noted that link(s) 1136 can include one or more links that functionally connect respective apparatuses, e.g., devices 1142, in the intra-premises network(s) 1140 to routing platform 1110. It is noted that routing platform 1110 has substantially the same, or the same functionality as routing platform 910 described herein.

Functional coupling amongst a deployed enterprise femto network and intra-premises network(s), e.g., 1140, can enable, at least in part, management of operations associated with an enterprise, e.g., a residence, a hospital, a hotel, or a small business, in which the enterprise femto network is deployed. Intra-premises network(s) 1140 can be deployed at least in part within the coverage area spanned by femto AP(s) 1120, and can be include at least one of a set of device(s) 1142, one or more server(s) 1144, or data storage 1146. In an aspect, the set of devices 1142 can be functionally coupled to one or more server(s) 1144 or with data storage 1146; a bus (not shown) can enable such functional connectivity. The set of one or more device(s) 1142 can include various types of apparatuses associated with specific aspect(s) of the deployed enterprise femto network; one or more devices within the set of device(s) 1142 can have wireless capability. For example, for a femto enterprise network deployed within a residence, device(s) 1142 can include one or more of an IPTV set, a high-definition TV (HDTV); a digital media frame; a DVD player; a personal computer (PC), a gaming console; a satellite radio tuner; home-office appliances such as photocopies, fax machines, scanners, or the like; one or more kitchen appliances; heating, ventilating and air conditioning (HVAC) equipment and controllers thereof such as thermostats; or the like. In addition, device(s) 1142 can include security equipment and controller(s) thereof, the controller(s) can be enabled or embodied, at least in part, through server(s) 1144. Security equipment can include on or more cameras, e.g., IR-sensitive or visible-radiation sensitive; a set of locks; IR and laser detectors or triggers; or the like.

Routing platform 1110 can enable content exchange among a mobile device 1130 that is served through a femto AP within the set of femto AP(s) 1120 that are part of the femto enterprise network, and any or substantially any of device(s) 1142, server(s) 1144, or data store(s) 1146. In an aspect of the subject embodiments, when a mobile device 1130 attaches to an authorized femto AP within femto AP(s) 1120, routing platform 1110 can signal available networked equipment, e.g., device(s) 1142, that is part of intra-premises network(s) 1140; access authorization to a femto AP is dictated at least in part by an access list associated therewith. Mobile device 1130 can allow an end user to manipulate content within the available equipment, wherein manipulation includes content transfer among disparate pieces of equipment or within disparate portions of a single piece of equipment; deletion of content within equipment; retrieval of content from equipment; and delivery of content to equipment. Content includes digital material such as records, files, media, or the like; in an aspect, content can include feature movies in Moving Picture Experts Group Phase 4 (MPEG-4), recommendation (Rec.) 601, or substantially any other video format; photos in Joint Photographic Experts Group (JPEG) format or substantially any digital frame image format; MPEG-1 audio layer 3 (MP3) files; recorded television shows. As an example, when a handset 1130 is attached to a femto AP within the set of femto AP(s) 1120 and when the handset 1130 is authorized for access to a personal computer (PC) and an internet protocol (IP) television (TV) included within device(s) 1142, video or photo(s) captured on the handset 1130 can be pushed to the PC for storage, or uploaded on near real-time or real-time for rendering on the IPTV. As another example, a subscriber of mobile device 1130 authorized to attach to a femto AP within the set of femto AP(s) 1120, can retrieve a movie recorded on a digital video recorder (DVR) or purchased through a pay-per-view service available via an IPTV, and provided at least in part through external network(s) 140, and upload the movie into the mobile device 1130 for later consumption, e.g., viewing the movie at a later time.

Availability of networked equipment can be dictated by an access list, e.g., a white list, which configures access privileges for mobile device 1130. In an example, an administrator, leaser, or owner of femto AP(s) 1120 and routing platform 1110, or a subscriber responsible for contracting service(s) provided through enterprise femto network can have unrestricted access to device(s) 1142, server(s) 1144, data store(s) 1146 or other equipment comprised within intra-premises network(s) 1140. Alternatively or additionally, a subscriber included within access list(s) linked to one or more femto AP(s) 1120 but without administrative privileges to configure access list(s), e.g., 353 or 498, can have access to a restricted portion of equipment within intra-premises network(s) 1140.

Routing platform 1110, through one or more of femto AP(s) 1120, also can enable control of equipment, e.g., device(s) 1142, within intra-premises network(s). To control equipment within intra-premises network(s) 1140, routing platform 1110 can receive instruction(s), relayed through a femto AP, within femto AP(s) 1120, that serves the mobile device 1130, and direct such instruction(s) to an intended equipment within intra-premises network(s) 1140. Configuration or authorization to control a device that is part of an intra-network can be supplied by at least one of a mobile device or a networked device within intra-premises network(s) 1140. The mobile device or the networked device is associated with a subscriber that can administer operation of routing platform 1110.

Control of equipment in intra-premises network(s) 1140 can be active or passive. Active control includes delivery of instructions that can determined operation of the equipment. Passive control can include monitoring of equipment. Routing platform 1110 enables passive control or monitoring, through delivery of information on operational condition(s), of equipment that is part of intra-premises network(s) 1140. Monitoring of operational condition(s) can be implemented in accordance with a predetermined, configurable monitoring profile; an end-user, a network operator, or an administrator of intra-premises network(s) can configure the monitoring profile. Routing of operation condition(s) information within the enterprise femto network can incur no costs, whereas delivery of such information to a recipient external to the femto enterprise network can be billed in accordance with a predetermined, configurable rate. Operational condition(s) can include ON/OFF status, alarm indication(s), e.g., associated with intrusion monitoring device(s) within device(s) 1142; operational metrics or set points such as temperature of one or more areas within the intra-premises network; or the like. It is noted that monitoring of intra-premises network equipment, e.g., device(s) 1142, can be exploited through a mobile device 1130 that operates within the coverage area of the enterprise femto network, or via consumer layer 580 through one or more external network(s) 140. As an example, an HVAC technician performing maintenance on a piece of equipment in a first section of a multi-floor office building can receive information on operation condition(s) of related equipment in a second section of the office building; typically, the second section disparate from the first section. As another example, when enterprise femto network is deployed within a healthcare facility and one or more devices within the set of devices 1142 are monitoring devices that collect vitals from one or more patients, routing platform 1110 can deliver such information to consumer layer 580 via an external network within external network(s) 140; e.g., consumer layer 580 can be embodied in a mobile device of a physician responsible for the one or more patients, and the external network can be a macrocell network platform.

It is noted that each of femto AP(s) 1120 in example system 1100, and other example system(s) described herein, can receive and convey or relay signaling and traffic from and to served mobile device(s) such as mobile 1130, and from and to routing platform 1110 as well. Such reception and delivery enables, at least in part, various aspects or features described herein.

Figure 12A:
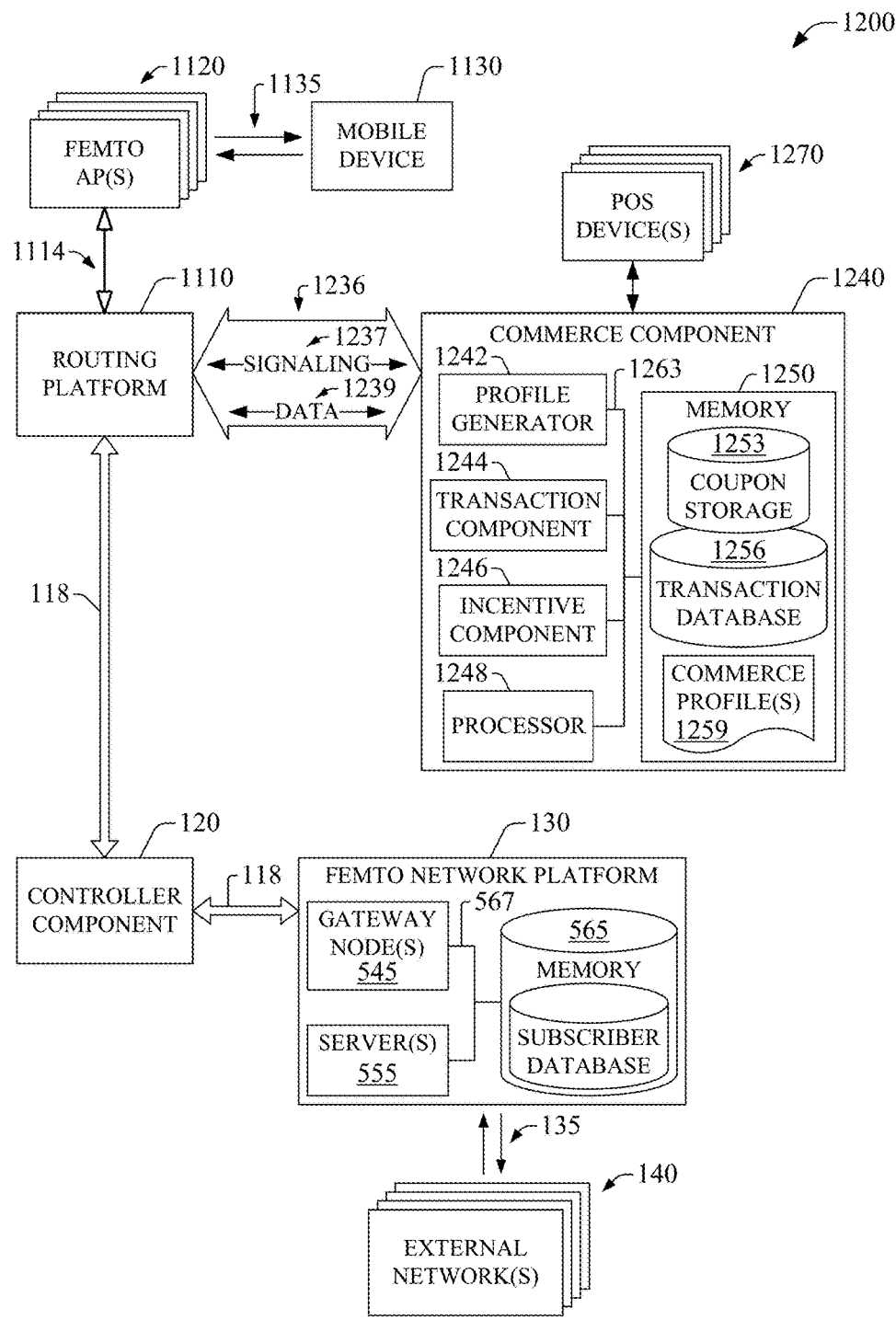
FIGS. 12A-12B are block diagrams of example systems that enable commercial transactions in an enterprise femto network in accordance with aspects described herein.

FIG. 12A is a block diagram of an example system 1200 that enables commercial transactions in an enterprise femto network in accordance with aspects described herein. Routing platform 1110 is functionally linked to a set of one or more femto APs 1120, which span a coverage area that can be a single-floor or multi-floor confined or nearly confined space. Based on at least one of location within the coverage area or access privilege(s) or right(s) established through access list(s), e.g., 353 or 498, a femto AP within the set of femto APs 1120 can serve mobile device 1130 through wireless link 1135. Routing platform 1110 also is functionally coupled to a commerce component 1240 through link(s) 1236, which can be reference link(s) or interface(s), or conventional wired or wireless link(s). The commerce component 1240 can enable, at least in part, commercial transaction(s) or service(s) consumption. In addition, commerce component 1240 can supply, e.g., deliver or credit, monetary incentive(s) to a device, mobile or otherwise, wherein the monetary incentive(s) can be utilized in at least one of the commercial transaction(s) or service(s) consumption as described herein.

Commerce component 1240 includes a profile generator 1242 that configures a commerce profile 1259, which can be linked to a single subscriber or a group of multiple subscribers, e.g., a consumer segment, and to a mobile device employed by the single subscriber or a subscriber within a consumer segment. Configuration can include generation of attributes and persistence of the same in memory 1250. In an aspect, a commerce profile 1259 can include at least one of billing account(s) to which charges related to commercial transactions or service(s) consumption are authorized to be billed; incentive program(s) associated with a subscriber for which the commerce profile is configured; or preferred brands or product features. Profile generator 1242 can receive, e.g., via data 1239, commercial information associated with the single subscriber or the consumer segment. In addition, profile generator 1242 can exploit machine learning methodologies, as those described supra, in order to generate autonomously a commerce profile 1259 based at least in part on historical commercial transactions effected by devices, mobile or otherwise, served through one or more of the femto APs within the set of femto AP(s).

Transaction component 1244 can enable, at least in part, the commercial transaction(s) via the femto enterprise network. In addition, transaction component 1244 can monitor and record commercial transactions; records can be retained in transaction database 1256. Moreover, transaction component 1244 can deliver monetary incentive(s) or coupon(s) to mobile device 1130, through at least in part data 1239; the incentive(s) or coupon(s) are relayed by routing platform 1110 to a femto AP in the set 1120 that serves mobile device 1130. It is noted that incentive(s) also can be delivered to a non-mobile device or apparatus with wireless capabilities. Delivery of the incentive(s) or coupon(s) also can be directed towards a coupon storage 1253 and linked, e.g., logically associated, or credited to a device recipient of the incentive(s) or coupon(s) for subsequent utilization in a commercial transaction. In an aspect, incentive(s) or coupon(s) can be delivered or credited based at least in part on at least one of location of mobile device 1130 within the coverage area of an enterprise femto network. As an example, in a scenario in which the femto enterprise network, e.g., 100, is deployed within a supermarket store, when a mobile device 1130 attaches to a femto AP that provides wireless service to a portion of the supermarket, e.g., the meat section, coupon(s) for specific meat(s) can be supplied, e.g., delivered or credited, to mobile 1130 or a consumer linked therewith.

To deliver or credit incentive(s) or coupon(s), transaction component 1244 can instruct, or command, incentive component 1246 to generate a set of incentive(s) or coupon(s). Generation of incentive(s) or coupon(s) can be based at least in part on the location of the mobile device 1130 or any other device that receives coupon(s). In an aspect, as part of the directive to generate incentive(s) or coupon(s), transaction component 1244 can supply location estimate(s) of mobile device 1130. In addition, transaction component 1244 can process, at least in part, billing charges for purchases or services incurred through mobile device 1130. The processing of billing charges can include redemption of coupon(s) presented or conveyed, via mobile device 1130, at the time of purchase or credited to the mobile device 1130. In an aspect, point of sales (POS) device(s) 1270 can provide with proof of transaction, e.g., a digital code or token, to commerce component 1240. Alternatively or additionally, POS device(s) 1270 can convey proof of transaction signaling to a femto AP within the set of femto APs 1120 that serves the area of the femto enterprise network wherein POS device(s) 1270 reside; for instance, in a supermarket store, such femto AP can be the one that serves the area where cash registers, e.g., POS devices, are located. In an aspect, POS device(s) 1170 can be deployed by a service provider that manages the enterprise femto network. Alternatively or additionally, a subset of POS device(s) 1170 can be deployed by a business operator that exploits, e.g., contracts, wireless service through the enterprise femto network.

It is noted that in one or more additional or alternative embodiments, commerce component 1240 can reside within routing platform 1110. In such scenario, link(s) 1236 can be part of a bus that functionally couples components or any other functional elements or circuitry within routing platform 1110.

It is noted that in example system 1200, commerce component 1240 can be administered by at least one of a business operator that owns or leases premises in which the enterprise femto network is deployed, or a network operator. Accordingly, the business operator can control level of monetary incentive(s) or coupon(s) that are supplied, conversion rate(s) among disparate types of monetary incentive(s), time span of promotional campaign(s), or the like. Such control can be substantially independent from management or control exerted by a network operator.

Figure 12B:
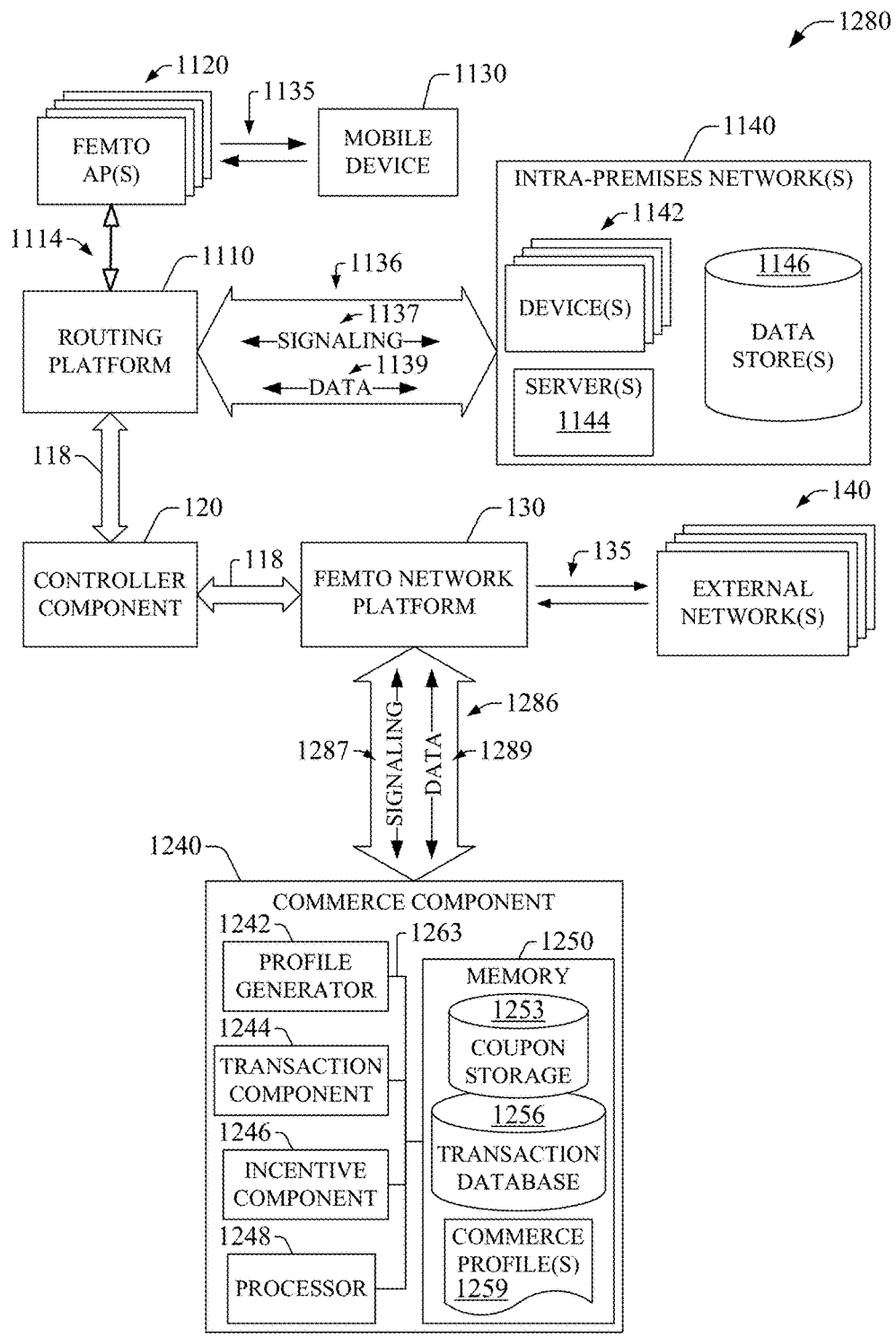

FIG. 12B is a block diagram of an example system 1280 that enables commercial transactions in an enterprise femto network and intra-premises network(s) linked thereto in accordance with aspects described herein. Commerce component 1240 is functionally coupled to femto network platform 130 through link(s) 1286, which can be reference link(s) or interface(s), or conventional wireless or wired link(s). In addition, it is noted that in example system 1280, in an aspect, commerce component 1240 can be part of one or more of external network(s) 140; for instance, commerce component 1240 can be part of an application server within an IMS network.

Commerce component 1240 operates as described supra; however, delivery of monetary incentive(s) or coupon(s) is effected through femto network platform, e.g., via gateway node(s) 545. It is noted that while such delivery can incur higher signaling among routing component 1110 and commerce component 1240, it has at least the advantage that a set of disparate enterprise femto networks (not shown in FIG. 12B) and respectively associated intra-premises network(s) (not shown), can be provisioned with monetary incentive(s) or coupon(s). Increased storage demand related to utilization of a larger number of commerce profiles 1259 to enable, at least in part, delivery of monetary incentive(s) or coupon(s) can be traded-off by the memory resources, e.g., memory 565, available to femto network platform 130; for instance, memory 565 can retain at least a portion of content(s) stored in memory 1250. A larger number of commerce profiles 1259 can arise from the larger set of disparate enterprise femto networks that can be served with monetary incentive(s) or coupon(s).

It is noted that in example system 1280, commerce component 1240 can be administered by the network operator that provides communication services, e.g., via femto network platform, and deploys at least in part the enterprise femto network. Accordingly, in an aspect, provision of monetary incentive(s) and coupon(s) related to communication service(s) can be directly managed by the network operator.

In example systems 1200 and 1280, commerce component 1240 includes processor(s) 1248 configured to confer, and that confers, at least in part, functionality to substantially any or any component within commerce component 1240 in accordance with one or more aspects of the subject embodiments. Processor 1248 is illustrated as external to the various functional elements or components of commerce component 1240; however, processor 1248 can be distributed amongst such various functional elements or components. Processor 1248 is functionally coupled to each functional element or component and to memory 1250 through bus 1263, which can be embodied in at least one of a memory bus, a system bus, an address bus, or one or more reference link(s) or interface(s). Processor 1248 can store information in, and retrieve information from, memory 1250 necessary to operate and/or confer at least in part functionality to each of the components that reside within commerce component 1240. The information can include at least one of code instructions, data structures, program modules, or the like. It is noted that in one or more alternative embodiments, processor 1248 can be external to commerce component 1240; for instance, such processor 1248 can reside within routing platform 1110.

Figure 13:
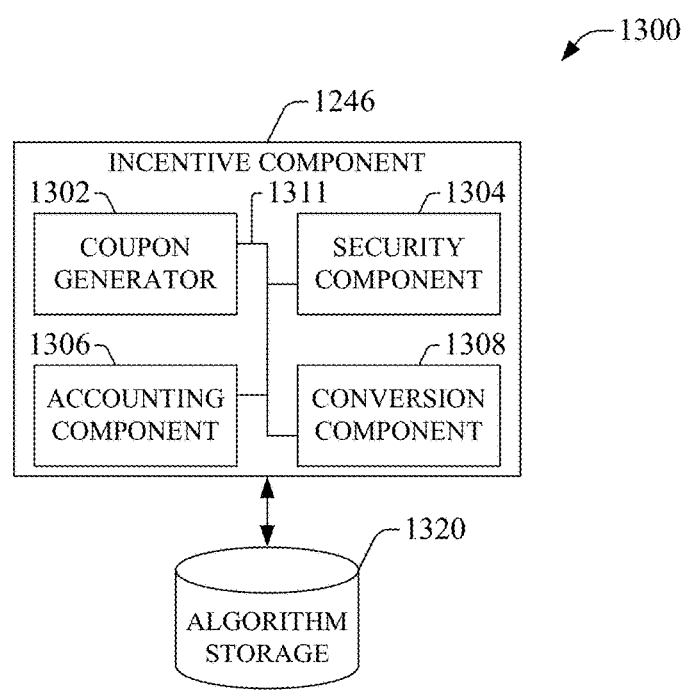
FIG. 13 is a block diagram of an example embodiment of an incentive component that enables one or more features of a commerce component that operates within an enterprise femto network in accordance with aspects described herein.

FIG. 13 is a block diagram of an example embodiment 1300 of an incentive component 1246 that enables one or more aspects of a commerce component 1240 that operates within an enterprise femto network. A coupon generator 1302 issues one or more type of monetary incentive(s) based at least in part on at least one of location of a recipient device or subscriber associated therewith. In an aspect, coupon generator 1302 can issue and supply, at least in part, monetary incentive(s) when a mobile device enters a coverage area of a deployed enterprise femto network, and attaches to a provisioned femto AP therein; the coverage area can be a commercial venue or a residence. In aspect, at least three classes of incentive(s) can be produced: (i) Loyalty-program incentives; (ii) brand development coupons; and (iii) consumer base development. With respect to (i), loyalty-program incentives can be based at least in part on a selection effected by a consumer linked to user equipment, e.g., mobile device 1130. In an aspect, loyalty programs can be based at least in part on historical data on commercial transactions retained in transaction database 1256. It is noted that utilized historical data can be directed to transactions associated with a pool of consumers, wherein the pool of consumers spans disparate scope of customers; commerce component 1240 can generate such pool of consumers based at least in part on a set of enterprise femto networks to which commerce component 1240 delivers monetary incentive(s). For example, historical data can include transactions effected by a set of consumers in a predetermined period of time; a segment of consumer can be grouped in accordance with a set of commercial metrics such as level of expenditure on a quarterly basis, demographics, etc.; consumers in a specific access list; or a single consumer.

In connection with (ii), coupon(s) or monetary incentive(s) are directed to raise awareness of a product or service, and can be part of a promotional campaign for the product or service. In an aspect, coupon(s) or monetary incentive(s) can be issued to a subscriber associated with a mobile device upon attachment of the mobile to a femto AP in the set of femto APs 1120.

In connection with (iii), coupon(s) or monetary incentive(s) are directed to elicit a direct response from a consumer or subscriber; e.g., increase consumer traffic or consumer interaction with a retailer or department within a store, wherein consumer interaction can include return of one or more subscribers to one or more retailers within an enterprise femto network. Coupon(s) or monetary incentive(s) can be issued based at least in part of on a pool of consumers such as all or nearly all consumers, a segment of consumers, or a single consumer. In an aspect, value or rate of issuance of coupon(s) or monetary incentive(s) can be based at least in part on commercial desirability of a segment of subscribers or a single subscriber, wherein commercial desirability can include predetermined, solid credit history, high-volume of purchases, high loyalty as revealed trough longevity of commercial relationship, etc. Such commercial desirability can be gleaned or determined, at least in part, from historical data on commercial transaction or through one or more external network(s) 140. In addition, a coupon or monetary incentive can be issued based at least in part on the time a subscriber station attaches to a femto AP in the set of femto APs 1120. As an example, in a scenario in which the femto enterprise network is deployed in a shopping mall, coupon generator 1202 can issue coupon(s) or incentive(s) for one or more restaurants in a food court within the shopping mall between the hours of 11:30 a-1:00 p, or any lunchtime hours. As another example, a coupon or monetary incentive associated with pizza delivery, or any other food delivery service, can be supplied to a subscriber that enters his or her residence at dinnertime Coupon(s) or monetary incentive(s) generated through incentive component 1246 can be subscriber centric and can be customized to various granularities, as described above in connection with loyalty programs. In an aspect, coupon(s) or monetary incentive(s) can be customized at a single subscriber level based at least in part on historical data on commercial transaction(s) or extracted pattern(s) thereof. It is noted that, in an aspect, pattern(s) of commercial transaction(s) can be identified by transaction component 1144 through machine learning methodologies discussed supra.

Security component 1304 can mitigate fraud related to coupon(s) or monetary incentive(s) consumption or redemption. In an aspect, security component 1304 can provide security features to issued coupon(s), wherein the features can include encryption, password protection, biometric-based protection, or substantially any security mechanism for digital content(s). Security component 1304 can generate security credentials such as passwords; encryption keys; digital certificates; biometric keys, e.g., voice recordings, iris patterns, fingerprints; or the like. Security credentials can be retained in memory 1250. To provide security features or credentials, security component 1304 can exploit one or more algorithms retained in algorithm storage 1320, which can be part of memory 1250.

In embodiment 1300, incentive component 1146 also can include an accounting component 1306 that can enable, at least in part, billing processing and redemption of issued coupon(s) or monetary incentive(s). Accounting component 1306 can record coupon(s) or incentive(s) collection or utilization, and such record(s) can be retained as part of transaction database 1256. In an aspect, accounting component 1306 can monitor coupon(s) or monetary incentive(s) associated with an access list and subscribers related thereto.

Conversion component 1208 can exchange a first type of issued coupon(s) or monetary incentive(s) to a second type of coupon(s) or monetary incentive(s). The first and second type of coupon(s) can be extracted from a commercial profile retained in memory element 1259 and associated with a set of one or more subscribers. Exchange rate(s) can be determined based at least in part on a segment of consumers or a single consumer that can be issued the first and second type of coupon(s) or monetary incentive(s). In addition, exchange rate(s) can be adjusted dynamically or based upon specific events. Conversion of coupon(s) or monetary incentive(s) can be signaled by accounting component 1306 as part of billing processing or coupon(s) or monetary incentive(s) redemption.

Figure 14A:
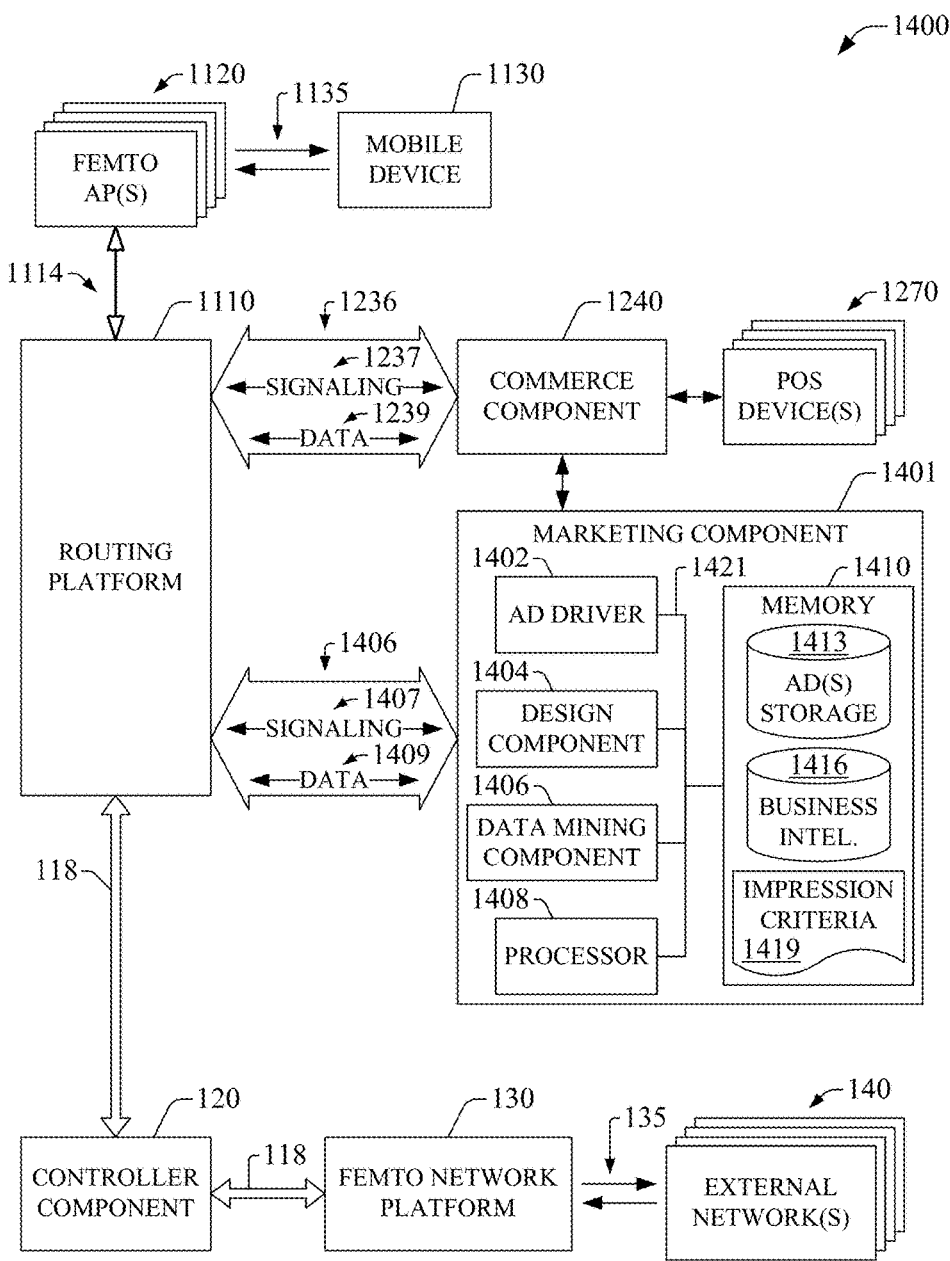
FIGS. 14A-14B illustrates a block diagram of an example system that enables marketing within an enterprise femto network in accordance with aspects described herein.

FIG. 14A illustrates a block diagram of an example system 1400 that enables marketing within an enterprise femto network in accordance with aspects described herein. Routing platform 1110 is functionally coupled with marketing component 1401 through link(s) 1406, which can allow exchange of signaling 1407 and data 1409. Link(s) 1406 can be reference link(s) or interface(s), or conventional wired or wireless link(s). Marketing component 1401 allows delivery of advertisement to mobile device 1130 based at least in part on at least one of location thereof or a subscriber associated with the mobile device 1130. In addition, marketing component 1310 can exploit pattern(s) of commercial transactions associated with a subscriber linked to mobile device 1130. Advertisement can be conveyed as part of data 1409, and routing platform 1110 can relay the advertisement to a femto AP that serves mobile device 1130; accordingly, advertisement delivery can be implemented without cost to a subscriber associated with mobile device 1130. Advertisement can be delivered as a SMS communication, an MMS communication, an email communication, an IM communication, a USSD message, or the like.

To deliver advertisement, marketing component 1401 can utilize advertisement driver component 1402, also herein referred to as ad driver 1402, which can extract advertisement content in accordance with a location estimate of mobile device 1130; the location estimate delivered by routing platform 1110 via data 1409. In addition, ad driver 1402 can convey advertisement based at least in part on the time mobile device 1130 attaches to a femto AP within the set of femto APs 1120. As an example, when enterprise femto network is deployed within a supermarket store, ad driver 1402 can deliver a frozen-dinner advertisement to a mobile device 1130 that attaches to a femto AP within the set of femto APs 1120 at dinnertime or a later time.

Ad driver 1402 can deliver advertisement in accordance with advertisement impression criteria 1419, also termed herein impression criteria 1419, which can include opt-out indicator(s), which can be configured through signaling delivered by mobile device 1130. Such signaling can be received by a femto AP that serves the mobile device 1130 and relayed, via signaling 1407, to marketing component 1401 by routing platform 1110. Opt-out indicators or flags can be embodied in at least one of a logical variable or a set of bits retained in impression criteria 1419. In addition, ad driver 1402 can deliver advertisement based at least in part on a list of items, e.g., wish list 955, received from a subscriber associated with a mobile device 1130. Routing platform 1110 can convey the list of items via data 1409.

Marketing component 1401 also can exploit advertisement to generate business intelligence and design customized advertisement campaign(s) or service(s) for consumers that conduct commercial transactions within a business in which the enterprise femto network is deployed. Design component 1404 can receive signaling to implement a specific advertisement campaign in accordance with specific impression criteria 1419. In addition, data mining component 1406 can identify response(s) to specific advertisement and generate information related to advertised product(s) or service(s), the information can be retained in memory element (e.g., a register, one or more files, a database or portion thereof) business intelligence 1416.

Design component 1404 can exploit business intelligence 1416 to adjust autonomously the advertisement campaign or advertised product(s) or service(s); adjusted advertisement(s) can be retained in ad(s) storage 1413. Autonomous adjustment can be implemented through utilization of machine learning techniques described supra. The adjusted advertisement campaign or product(s) or service(s) can be delivered through ad driver 1402 for further collection of business intelligence. In an aspect, upon completion of an adjustment cycle, which can be defined as at least one of a set of advertisement campaigns, a predetermined time of advertisement, at least one of a business that utilizes the enterprise femto network or a network operator that administers the enterprise femto network can employ collected business intelligence 1416.

Figure 14B:
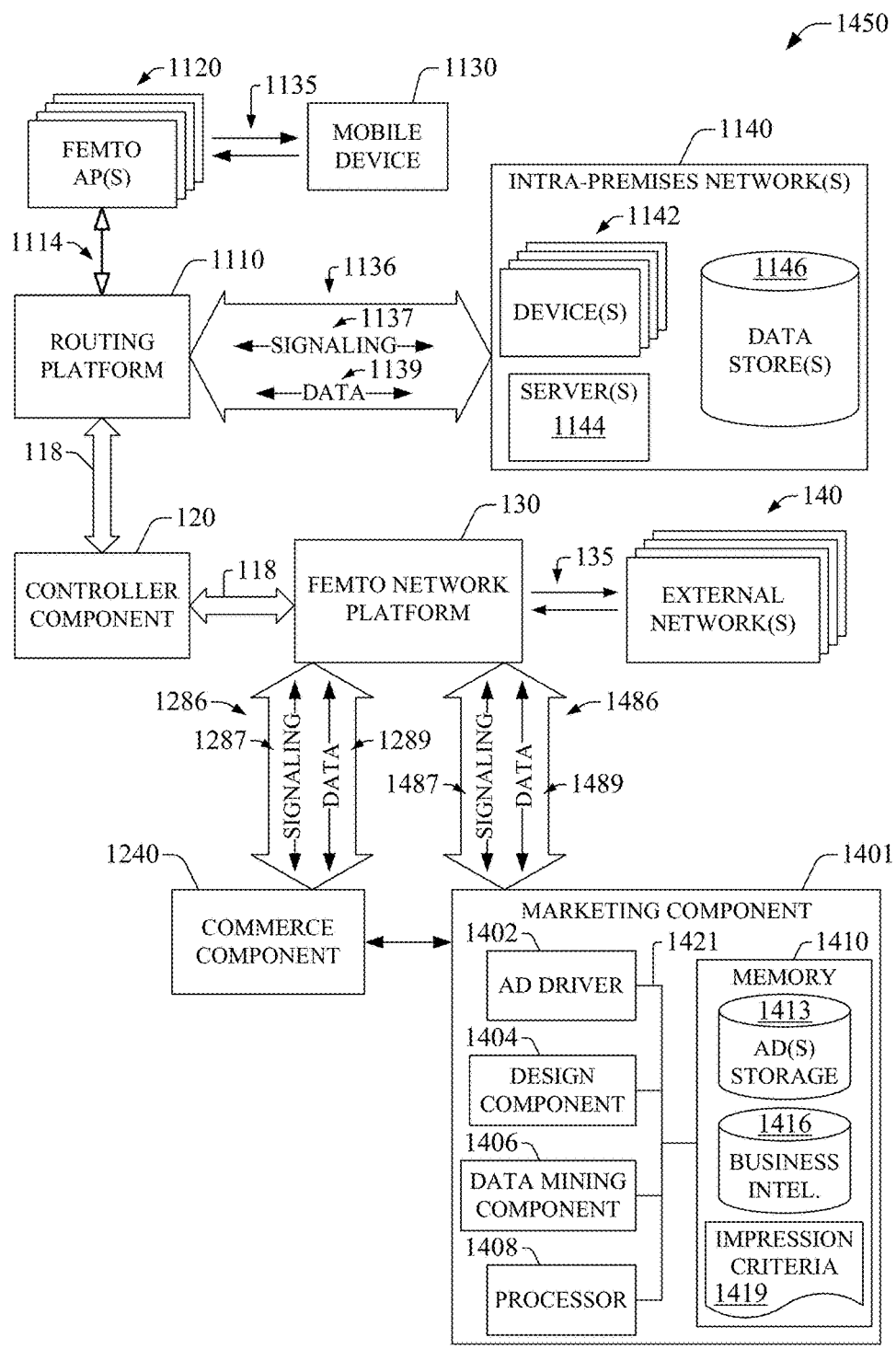

FIG. 14B is a block diagram of an example system 1450 that enables marketing within an enterprise femto network and intra-premises network(s) linked thereto in accordance with aspects described herein. Marketing component 1401 is functionally coupled to femto network platform 130 through link(s) 1486, which can be reference link(s) or interface(s), or conventional wireless or wired link(s). In addition, it is noted that in example system 1450, in an aspect, marketing component 1240 can be part of one or more of external network(s) 140; for instance, marketing component 1401 can be part of an application server within an IMS network.

Marketing component 1401 operates as described supra; however, delivery of advertisement is effected through femto network platform, 130 e.g., via gateway node(s) 545. It is noted that while such delivery can incur higher signaling among routing component 1110 and marketing component 1401, it has at least the advantage that a set of disparate enterprise femto networks (not shown in FIG. 14B) and respectively associated intra-premises network(s) (not shown), can be supplied with advertisement. Increased storage demand related to utilization of a larger number of impression criteria 1419 that regulate exposure of a mobile device within an enterprise femto network can be compensated, at least in part, by memory resources, e.g., memory 565, available to femto network platform 130. Similarly, increased volume of business intelligence 1416 can be side-loaded to storage resources, e.g., memory 565. As described in connection with commerce component 1240, increased volume of business intelligence 1416 can arise from the larger set of disparate enterprise femto networks that can be exposed to advertisement and collected response thereto.

In an aspect, for targeted advertisement, marketing component 1401, e.g., via design component 1404, can identify or categorize a residential location in which an enterprise femto network is deployed as "at home" network or "home" network; it should be appreciated that other labeling can be employed, such as "residence" or "dwelling," etc. Alternatively or additionally, the same or substantially the same categorization can be employed to distinguish business intelligence generated through residential enterprise femto network from business intelligence collected through a commercial enterprise femto network. It should be appreciated that categorization, e.g., either "residence" or "business," can reveal substantially disparate patterns of responses to advertisement. Thus, design component 1404 can adjust development parameters employed to produce advertisement campaigns suitable for a specific categorization; such development parameters can include rate of ad delivery, privacy metric or considerations, length of advertisement campaigns, specific content(s) of advertisement campaign such as adult-oriented material or general content; or the like.

For "home" enterprise femto networks, marketing component 1401, e.g., through design component 1404, can exploit access list(s) and associated opt-in/opt-out flags to determine scope of an advertisement campaign, wherein the scope includes at least one of content, length, frequency, advertised products or brands, etc. In addition, for a specific access list and based at least in part on privacy metrics or indicators, data mining component 1406 can extract subscriber information linked to unique mobile device identifier(s) within the specific access list. Moreover, data mining component 1406 can exploit one or more of external network(s) 140 to extract information related to the unique identifier such as community membership, public records, and so forth.

Based on privacy settings related to equipment in intra-premises network(s) associated with an enterprise femto network, data mining component 1406 can collect information on activity or processing load associated with the equipment through exchange of signaling with routing platform 1110—e.g., signaling 1487 as a probe and signaling 1137 as a response. Data mining component 1406 can provide the collected information to ad driver 1402 to elicit delivery of advertisement targeted or customized for the specific information. In an example, equipment in intra-premises network associated with a home enterprise femto network can include a vehicular navigation system with wireless capability. In addition, an access list for one or more femto APs in a home enterprise femto network can disclose that traffic and signaling communicated from the vehicular navigation system to the one or more femto AP can be disclosed or conveyed to a marketing component 1401 in response to an inquiry there from. In such scenario, data mining component 1406 can poll, e.g., inquiry for information at a predetermined rate, the vehicular navigation system, such polling can be enabled by routing platform 1110, in order to extract information associated with configured destinations. Based on a configured destination, ad driver 1402 can select and deliver advertisement to the vehicular navigation system through the routing platform; for instance, the advertisement can include announcement of sponsored activities in a destination. Moreover, ad driver 1402 can request coupon(s) from commerce component 1240 and deliver such coupon(s) to the vehicular navigation system; delivery of coupon(s) or other monetary incentive(s) can occur in conjunction with delivery of advertisement.

It is noted that in example system 1450, marketing component 1401 can be administered by the network operator that provides communication services, e.g., via femto network platform 130, and deploys at least in part the enterprise femto network. Accordingly, in an aspect, advertisement content(s) and delivery thereof can be directly managed by the network operator.

In example systems 1400 and 1450, marketing component 1401 includes processor 1408 configured to confer, and that confers, at least in part, functionality to substantially any or any component within marketing component 1401 in accordance with one or more aspects of the subject embodiments. Processor 1408 is illustrated as external to the various functional elements or components of marketing component 1401; however, processor 1408 can be distributed amongst such various functional elements or components. Processor 1408 is functionally coupled to each functional element or component and to memory 1401 through bus 1421, which can be embodied in at least one of a memory bus, a system bus, an address bus, or one or more reference link(s) or interface(s). Processor 1408 can store information in, and retrieve information from, memory 1410 necessary to operate and/or confer at least in part functionality to each of the components that reside within marketing component 1401. The information can include at least one of code instructions, data structures, program modules, or the like. It is noted that in one or more alternative embodiments, processor 1408 can be external to marketing component 1301; for instance, such processor 1408 can reside within routing platform 1110 or commerce component 1240.

Figure 15:
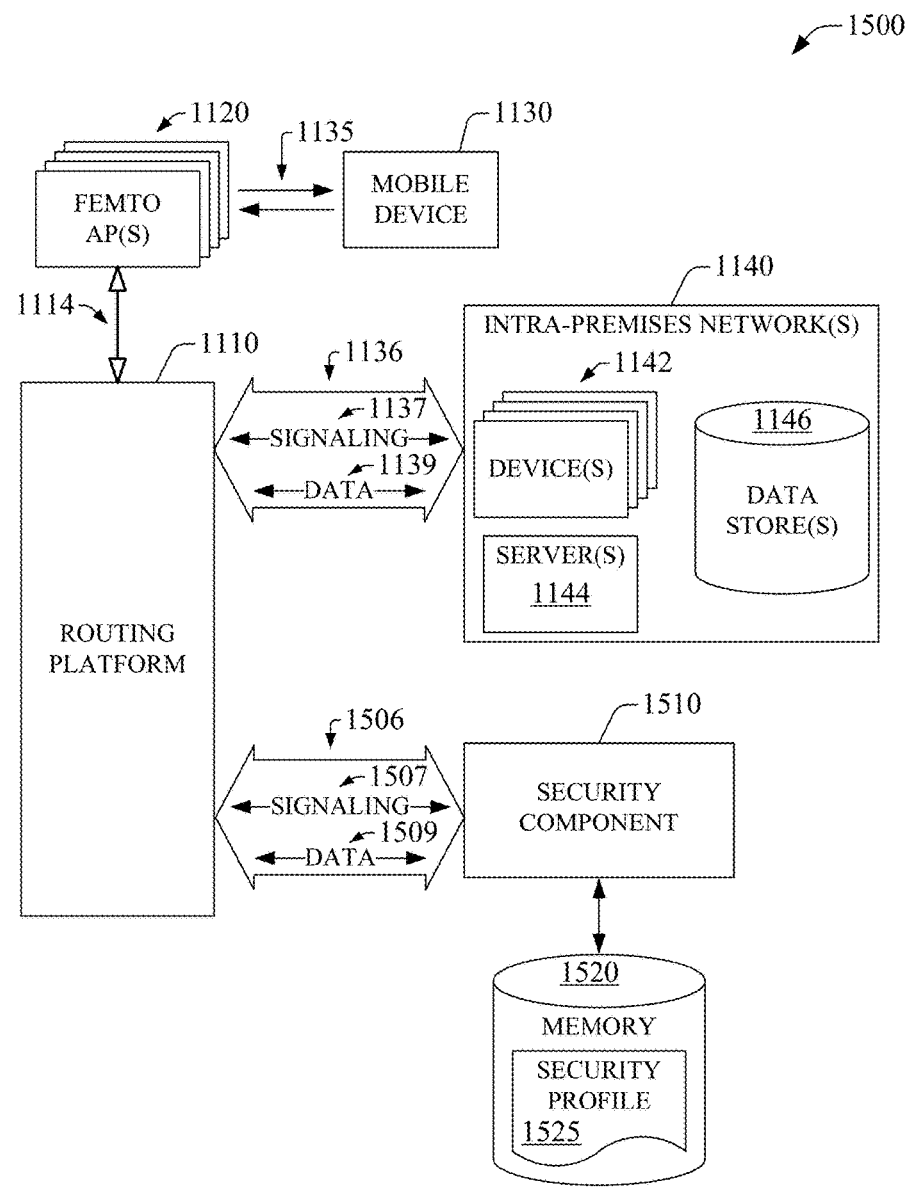
FIG. 15 illustrates, respectively, a block diagram of an example system that can enable security features within at least one of an enterprise femto network or an intra-premises network coupled thereto in accordance with aspects described herein.

FIG. 15 illustrates, respectively, a block diagram of an example system that can enable security features within at least one of an enterprise femto network or an intra-premises network coupled thereto in accordance with aspects described herein. Security component 1510 is coupled to routing platform 1110 through link(s) 1506, which can be reference link(s) or interface(s), or conventional wired or wireless link(s). Security component 1510 can control access to wireless service, or voice or data available there from, for mobile device 1130 based at least in part on subscriber information linked thereto. To effect such control, security component 1510 can configure a set of access lists for a set of respective femto APs, e.g., femto AP(s) 1120. For a specific subscriber, security profile 1525 can indicate or establish a set of security clearances to one or more areas covered through the set of femto APs for which access to wireless service is configured. Based on the security clearances, control parameters that can be included in an access list and that control logic of access to wireless service such as allocated bandwidth, service priority, allowed period of service, service category such as "voice only," voice and data," or "data only," allowed quality of service, and so forth. In addition, security component 1510 also can configure access, e.g., through mobile device 1130, to at least one of device(s) 1142, server(s) 1144, or data storage 1146, based at leas in part on security clearance for a subscriber linked to mobile device 1130. In an aspect, access can be dictated through logical flag(s) set by security component 1510 through communication of data 1509 or signaling 1507. Logical flag(s) can be retained within security profile 1525 or each of the configured device(s), server(s), or data storage.

Furthermore, based at least in part of location of mobile device 1130 within the enterprise femto network, security component 1510 can control, through signaling 1509, one or more security devices that can be part of an intra-premises network within the set of intra-premises networks 1140. In an aspect, control of the security devices is aimed at monitoring activities of an operator of mobile device 1130, or allowing or denying physical access to specific areas of coverage of femto enterprise network served through femto AP(s) 1120. As an example, security component can allow or deny physical access through delivery of signaling 1507 to routing platform 1110 to switch close or open one or more locks that are part device(s) 1142; in an aspect, routing platform 1110 can relay such signaling to one or more femto APs, which can deliver the switching signaling to one or more specific locks.

Security profile 1525 can be retained in memory 1520, which can be accessed by security component 1520 to implement at least part of the security features described herein. It is noted that in one or more additional or alternative embodiments, security profile 1525 can reside within routing platform 1110. In an aspect of the subject embodiments, security profile 1525 is associated, e.g., logically linked to one or more access list(s) 353, which can be stored in routing platform 1110 and regulate access to wireless service provided through femto AP(s) 1120.

Processor(s) (not shown) that can reside within security component 1510 can provide at least part of the functionality of such component. To operate or confer at least in part functionality to security component 1510, the processor(s) can store information in, and retrieve information from, a memory such as memory 1520. The information can include at least one of code instructions, data structures, program modules, or the like. In one or more alternative embodiments, the processor(s) that provide functionality, through execution of code, for example, to security component 1510 can reside within routing platform 1110.

Figure 16:
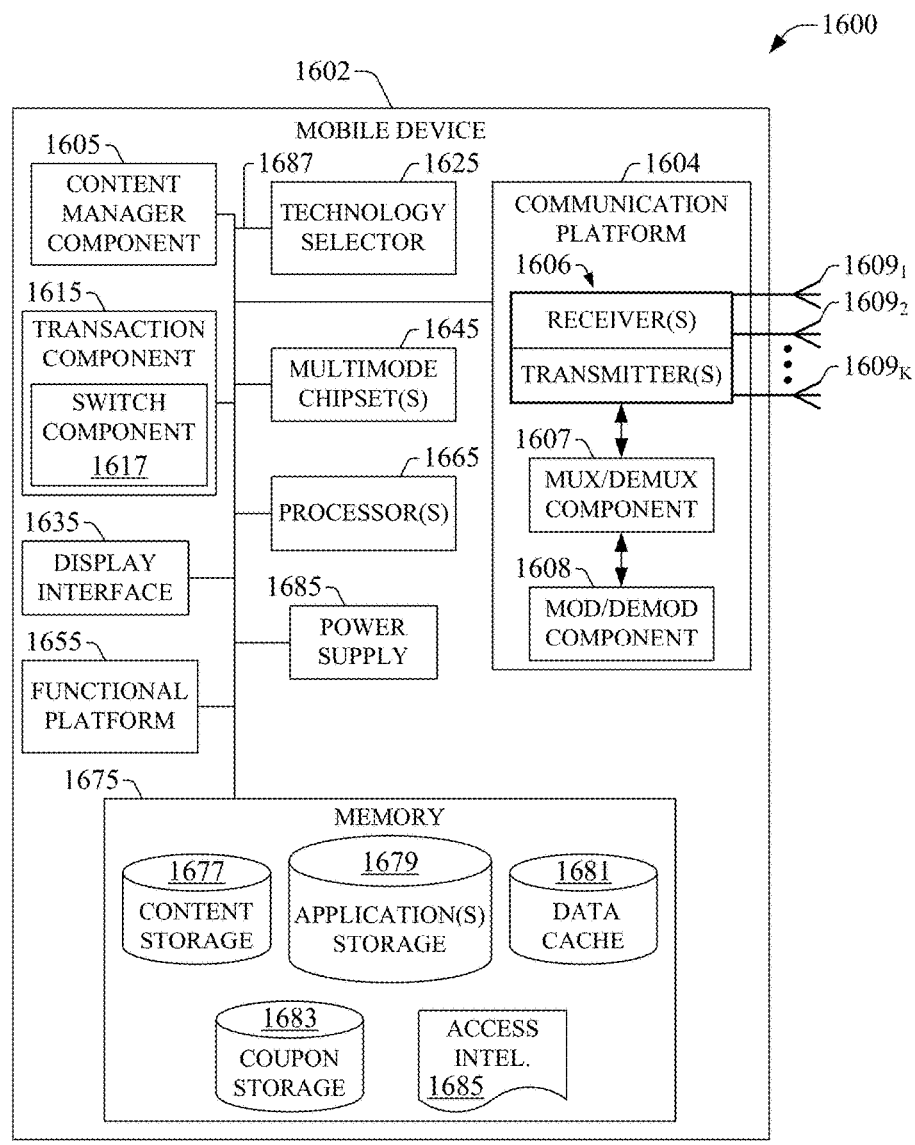
FIG. 16 is a block diagram of an example embodiment of a mobile device that can enable and exploit various aspects of the subject embodiments described herein.

FIG. 16 is a block diagram of an example embodiment 1600 of a mobile device 1602 that can enable and exploit various aspects of the subject application described herein. Mobile device 1602 can embody, and operate in substantially the same or the same manner as, mobile device 1130 or any other mobile device described in the subject specification. Mobile device 1602 can include a content manager component 1605 that enables manipulation of content retained in memory element 1677, or content storage 1677. Such manipulation can include exchange of content with a networked device to which mobile device 1602 is allowed access; exchange can include extraction of content from the networked device, or delivery of content to such networked device. The networked device can be part of an intra-premises network deployed within the coverage area of an enterprise femto network. In an aspect, such content can comprise digital material such as records, files, media, or the like; in an aspect, content can include feature movies in Moving Picture Experts Group Phase 4 (MPEG-4), recommendation (Rec.) 601, or substantially any other video format; photos in Joint Photographic Experts Group (JPEG) format or substantially any digital frame image format; MPEG-1 audio layer 3 (MP3) files; text files or document files such as documents in portable document format (PDF); or the like. In an aspect, content retained in content storage 1677 can be generated through the mobile device, e.g., through functional platform 1655.

Alternatively or additionally, content can include monetary incentive(s), such as coupon(s), which can be received over the air via communication platform 1604. In a commercial transaction, content manager component 1605 can select and push the coupon(s) as part of purchase of goods such as groceries, appliances, digital content, or the like. In an aspect, content retained in content storage 1677 can include digital signature(s) secured through one or more mechanisms such as encryption or biometric tagging, e.g., the digital signature(s) can be embedded with voice recordings, iris or fingerprint patterns, DNA sequences, etc., to provide security; the digital signatures can be employed in commercial transaction(s) as well.

Mobile device 1602 also includes a transaction component 1615 that can receive, through communication platform 1604, signaling that authorizes the mobile device 1602 to manipulate content with a disparate networked device. In addition, transaction component 1615 can receive and convey, through communication platform 1604, signaling and data that enables at least in part commercial transaction(s) or service(s) consumption. Transaction component 1615 can communicate control information, as part of signaling, to effect or complete a commercial transaction, e.g., a purchase, or to convey a command to equipment, e.g., device(s) 1142, within intra-premises network(s) 1140. In an aspect, transaction component 1615 can exploit technology selector 1625 to configure, at least in part, communication platform 1604 to operate in a predetermined frequency band or carrier and in accordance with a specific radio technology. For instance, transaction component 1615 can set communication platform 1604 to deliver wireless signal(s) in an infrared (IR) portion of the electromagnetic (EM) spectrum to communicate signaling and traffic within a point-to-point (PTP) short-range mode of operation. Such PTP communication can enable delivery of purchase or service request(s) to a POS device, e.g., 1460. In addition, transaction component 1615 can deliver purchase or service request(s) to a femto AP. Transaction component 1615 can exploit at least one of display interface 1635, which can include a data entry component (not shown), or an application within application(s) storage 1679, to generate and deliver purchase or service request(s), or to generate directive(s) to control equipment within intra-premises network(s) 1140. For packet-based communication, access intelligence 1685 can include logical address(es), e.g., an internet protocol (IP) address, and related PDP context(s) associated with the mobile device 1602 and the utilized application.

Transaction component 1615 also can include switch component 1617 that accepts or rejects prompt(s) to receive promotional content(s) such as advertisement, or coupon(s) or other type of monetary incentive(s). A prompt to receive promotional content(s) can be received by communication platform 1604, which can relay the prompt, after decoding thereof, to transaction component 1615. In an aspect, switch component 1617 can exploit at least one of display interface 1635 and an application within application(s) storage 1679 to convey the prompt to an end-user and to collect a response to the prompt. Switch component 1617 can configure an opt-in flag or variable in accordance with a received response to the prompt. In an aspect, switch component 1617 can retain the opt-in flag within a configuration file (not shown) that is part of access intelligence 1683.

Additionally, when a prompt to receive promotional content(s) is accepted, transaction component 1615 via at least one of display interface or an application within application(s) storage 1679 can convey a response to received advertisement(s) or monetary incentive(s). Such response can be delivered through communication platform 1604, and can be collected by a recipient, such as marketing component 1401, to generate business intelligence as discussed supra. In an aspect, switch component 1617 can exploit machine learning techniques, indicated supra, to perform a cost-utility analysis to determine a financial gain, or utility, from receiving a predetermined volume of coupons or incentives with respect to a cost, e.g., battery drain, of receiving the predetermined volume of coupons.

In mobile device 1602, which can operate in multi-technology multimode, a set of antennas $1609_1$-$1609_K$ (K is a natural number) can receive and transmit signal(s) from and to network elements such as femto access points, access terminals, wireless ports and routers, or the like, within an enterprise femto network. It is noted that antennas $1609_1$-$1609_K$ also can allow communication with base stations within a macrocell radio access network. Antennas $1609_1$-$1609_K$ are a part of communication platform 1604, which can comprise electronic components and associated circuitry that enable processing and manipulation of received wireless signal(s) and wireless signal(s) to be transmitted. Wireless signal(s) can include traffic, e.g., at least a portion of data 1512 or 1554, and signaling such as at least a portion of signaling 1514 or 1552. In an aspect, communication platform 1604 can receive and deliver signaling that allows commercial transactions or navigation throughout a coverage area of an enterprise femto network in accordance with aspects described herein.

In an aspect, communication platform 1604 includes receiver(s)/transmitter(s) 1606 that can convert signal from analog to digital upon reception, and from digital to analog upon transmission. Receiver/transmitter 1606 also can divide a single data stream into multiple, parallel data streams, or perform the reciprocal operation; such operations typically conducted in various multiplexing schemes. Functionally coupled to receiver(s)/transmitter(s) 1606 is a multiplexer/demultiplexer (mux/demux) component 1607 that facilitates manipulation of signal in time and frequency space or domain. Electronic mux/demux component 1607 can multiplex information (data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1607 can scramble and spread information (e.g., codes) according to substantially any code; e.g., Hadamard-Walsh codes, Baker codes, Kasami codes, polyphase codes, and so on. A modulator/demodulator (mod/demod) component 1608 also is a part of communication platform 1604, and can modulate information according to various modulation techniques, such as frequency modulation (e.g., frequency-shift keying), amplitude modulation (e.g., M-ary quadrature amplitude modulation (QAM), with M a positive integer; amplitude-shift keying (ASK)), phase-shift keying (PSK), and the like. In an aspect of embodiment 1600, mod/demod component 1608 is functionally coupled to mux/demux component 1607.

In addition, it is noted that a network operator that manages at least one of a macrocell network platform, which can be embodied in one of external network(s) 140 or femtocell network platform 130, can configure, e.g., as part of provisioning of mobile device 1602, a set of electromagnetic (EM) frequency bands and a set of radio technologies that communication platform 1604 and components therein can exploit for communication. The set of EM frequency bands can comprise radio frequency (RF) portion(s) and microwave portion(s) of the EM spectrum, although other spectral regions such as infrared (IR) can be included. It is noted that as part of over-the-air upgrades, the service provider can add frequency bands, or frequency carriers therein, to the set of EM frequency bands as such bands or carriers become available for communication, e.g., auctioned for utilization or authorized for free-of-charge utilization. Similarly, as new radio technologies become standardized, or available, the network operator can introduce such technologies in the set of radio of technologies that can be utilized for communication.

In embodiment 1600, processor(s) 1665 enables, at least in part, mobile device 1602 to process data (e.g., symbols, bits, or chips) for multiplexing/demultiplexing, modulation/demodulation, such as implementing direct and inverse fast Fourier transforms, selection of modulation rates, selection of data packet formats, inter-packet times, etc.

Additionally, in embodiment 1600, multimode chipset(s) 1645 can allow mobile device 1602 to operate in multiple communication modes through various radio network technologies (e.g., second generation (2G), third generation (3G), fourth generation (4G)) or deep-space satellite-based communication in accordance with disparate technical specifications, or standard protocols, for the radio network technologies or satellite communication. In an aspect, multimode chipset(s) 1645 can utilize communication platform 1604 in accordance with standard protocols specific to a mode of operation, e.g., GNSS-based communication or LTE-based communication. In another aspect, multimode chipset(s) 1645 can be scheduled to operate concurrently (e.g., when K>1) in various modes or within a multitask paradigm in which the multimode chipset(s) 1645 operate in a dedicated mode for a specific time interval.

Technology selector 1625 can drive operation of multimode chipset(s) 1645 through configuration of one or more radio network technologies for communication in a specific telecommunication mode. In an aspect, when mobile device 1602 is enabled with GNSS service, which can be effected through execution of an application retained in application(s) storage 1679, technology selector 1625 can exploit multimode chipset(s) 1645 and communication platform 1604 to receive and process GNSS timing messages to extract a location estimate for the mobile device 1602. Processing of GNSS timing messages includes implementation of a triangulation procedure of available or "visible" satellites to generate the location estimate. In another aspect, technology selector 1625 can switch operation of mobile device 1602 to deliver and receive, via communication platform 1604, at least one of short-range infrared (IR), RF, or microwave wireless signal(s). To switch to such mode of operation, technology selector 1625 can receive signaling, through communication platform 1604, from at least one of a femto AP within set 1120 or a device with wireless capabilities within the set of device(s) 1142 that are part of intra-premises network(s).

Mobile device 1602 also includes a functional platform 1655 that comprises a set of components (not shown) that provide, at least in part, one or more specific functionalities that complement or supplement wireless communication. As an example, when mobile device 1602 is a telephone, functional platform 1655 can include functional elements such as a data entry interface (e.g., a touch screen, a keyboard, a biometric pad for biometric-based access, a microphone, a loud speaker), a camera, peripheral connectors (e.g., a universal serial bus (USB) port or an IEEE 1394 port for transferring data to a disparate device), a voice coder-decoder; intelligent component(s) that can respond to voice activated command(s); and so on. It should be appreciated that functional platform 1655 can exploit applications retained, e.g., in application(s) storage 1679 within memory 1675 in order to provide one or more functionalities of mobile device 1602. In an aspect, application(s) storage 1679 also can include an application that when executed by at least processor(s) 1665 can interface a subscriber with GNSS-based location estimates and associated data such as maps, landmarks, related businesses, etc. In another aspect, application(s) storage 1679 can include an application that when executed by at least processor(s) 1665 can process navigation instruction(s) received from a routing platform, e.g., 1110, within an enterprise femto network, and supply such instructions in a format, e.g., a floor plan with visual or aural indicia that indicate at least origin and destination locations, that can be rendered in a graphic user interface (GUI) that can be implemented through display interface 1635. In yet another aspect, an application within application(s) storage 1679 also can supply at least one of received advertisement(s) or coupon(s) to display interface 1635 for rendition thereof; processor(s) 1665 can enable, at least in part, such rendition of advertisement(s) or coupon(s).

In a further aspect, application(s) storage 1679 can include an application that when executed by a processor, e.g., 1665, enables, at least in part, display of device(s) within an intra-premises network, e.g., one network within set 1140, to which mobile device 1602 has access for content consumption or manipulation, or for control of one or more of such device(s). In addition, the application that when executed by a processor enables display of available networked device(s) also can enable transaction component 1516 to convey, e.g., through at least in part through display interface 1635, a set of available commands to manipulate operation of the one or more device(s). The set of available commands (not shown) can be specific to the device that mobile device 1602 is authorized to control, and can be retained in memory 1675. For such device, signaling specification(s) such as modulation features, e.g., constellations, modulation format; coding rate; or EM radiation frequency band(s) for implementation of the set of available commands can be received over-the-air (OTA), via communication platform 1604, at the time mobile device 1602 is configured to control the device. As an example, mobile device 1602 can be allowed to control an IPTV set, and thus the mobile device 1602 can become a remote control for the IPTV.

Display interface 1635, which in one or more disparate or additional embodiments of mobile device 1602 can reside within functional platform 1655, allows gestures for subscriber-device interaction via at least one of a touch-responsive screen or otherwise such as a liquid crystal display (LCD), a plasma panel, a monolithic thin-film based electrochromic display; a sound interface; or the like. Additionally, display interface 1635 can render content(s) that control functionality of mobile device 1602 as available in functional platform 555, or reveal operational conditions of the mobile device 1602.

Mobile device 1602 also can retain access intelligence 1683, e.g., navigation instructions; configuration file(s) that contain one or more variable(s) that regulate reception of at least one of advertisement(s) or incentive(s); access list(s), handover log(s), or the like, in memory 1675. At least a portion of such access intelligence 1683 can be collected by the mobile device 1602, or can be received as part of provisioning proceeding(s).

In addition, mobile device 1602 includes processor(s) 1665 configured to confer, and that confer, at least in part, functionality to substantially any or any component, platform, interface, selector, and so forth within mobile device 1602 in accordance with one or more aspects of the subject application. In embodiment 1600, processor(s) 1665 is illustrated as external to the various functional elements (e.g., component, interface, platform, selector) of mobile device 1602; however, processor(s) 1665 can be distributed amongst such various functional elements. Processor(s) 1665 is functionally coupled to each functional element and to memory 1675 through bus 1683, which can be embodied in at least one of a memory bus, a system bus, an address bus, or one or more reference link(s) or interface(s). Processor(s) 1665 can store information in and retrieve information from memory 1675 necessary to operate and/or confer functionality, at least in part, to communication platform 1604, transaction component 1615, technology selector 1625, display interface 1635, multimode chipset(s) 1645, functional platform 1655 and component(s) therein, as well as other operational components (not shown) of multimode mobile device 1604. The information can include at least one of code instructions, code structure(s), data structures, or the like.

Memory 1675 can retain, at least in part in application storage(s) 1679, at least one of data structures (e.g., objects, classes, metadata); code structure(s) (e.g., modules, procedures) or instructions; or substantially any type of software or firmware that processor(s) 1665 can execute to provide functionality associated with substantially any or any component, platform, interface, selector, and so forth, within mobile device 1602 in accordance with aspects of the subject application. As indicated supra, memory 1675 can include content storage 1677. Moreover, memory 1675 can include coupon storage 1683, which can retain coupon(s) or other digital incentive(s) or indicators of availability thereof. Coupon(s) or incentive(s) can be received when an opt-in flag or variable has a logic value, e.g., 'coupon.receive=TRUE', that indicates that coupon(s) or incentive(s) can be received. In an aspect, the opt-in flag or variable can be an entry in a configuration file (not shown) retained in access intelligence 1685 or data cache 1681. Similarly, an advertisement opt-in flag or variable, e.g., 'ads.receive' can dictate if advertisement can be received by mobile device 1602; such opt-in flag also can be retained within the configuration file stored in access intelligence 1685 or data cache 1681. Access intelligence 1685 also can include logical variables or flags that indicate mobile device 1602 has been included in an access list, e.g., a white list, to access a specific femto AP within an enterprise femto network; e.g., a femto access point within set of femto APs 1120. It is noted that data cache 1681 also can retain received advertisement(s); data cache 1681 can be flushed, by transaction component 1615, for example, on at least one of a schedule basis or an event basis, such as handover from enterprise femto network to macrocell coverage.

Furthermore, memory 1675 can retain network or device information (not shown) such as encoded pilot signal(s) (e.g., encoded sounding reference signal(s)); one or more communication protocol(s) or technical specification(s); code sequences for scrambling or spreading; blind decoding hypotheses; semi-persistent scheduling parameters; frequency offsets, macrocell identifiers (IDs); address book(s); or the like. Moreover, memory 1675 can retain content(s) such as multimedia files or subscriber-generated data; security credentials (e.g., passwords, encryption keys, digital certificates, biometric keys such as voice recordings, iris patterns, fingerprints); hardware identifying tokens or codes such as at least one of an international mobile subscriber identity (IMSI), a temporary mobile subscriber identity (TMSI), packet TMSI (P-TMSI), an international mobile equipment identifier (IMEI), a mobile directory number (MDN), a mobile identification number (MIN), a Telecommunications Industry Association (TIA) electronic serial number (ESN), or a multi-bit identification number like the mobile identity number (MEID). It is noted that memory 1675 can include stationary or removable elements such as a subscriber identification module (SIM) card storage, a universal integrated circuit card (UICC) storage, or a removable user identity module (RUIM).

Mobile device 1602 also includes power supply 1685, which can power up components or functional elements within mobile device 1602. Power supply 1685 can be a rechargeable power supply, e.g., a rechargeable battery, and it can include one or more transformers to achieve power level(s) that can operate mobile device 1602 and components, functional elements, and related circuitry therein. In an aspect, power supply 1685 can attach to a conventional power grid to recharge and ensure mobile device 1602 is operational; power supply 1685 can include an I/O interface (not shown) to connect operationally to the conventional power grid. Moreover, power supply 1685 can include an energy conversion component (not shown), such as a solar panel, to provide additional or alternative power resources or autonomy to mobile device 1602.

In view of the example systems described above, example methods that can be implemented in accordance with the disclosed subject matter can be better appreciated with reference to flowcharts in FIGS. 17-36. For purposes of simplicity of explanation, example methods disclosed herein are presented and described as a series of acts; however, it is to be understood and appreciated that the claimed subject matter is not limited by the order of acts, as some acts may occur in different orders and/or concurrently with other acts from that shown and described herein. For example, one or more example methods disclosed herein alternatively or additionally can be represented as a series of interrelated states or events, such as in a state diagram. Moreover, interaction diagram(s) may represent methods in accordance with the disclosed subject matter when disparate entities enact disparate portions of the methodologies. Furthermore, not all illustrated acts may be required to implement a described example method in accordance with the subject specification. Further yet, two or more of the disclosed example methods can be implemented in combination with each other, to accomplish one or more features or advantages herein described. It should be further appreciated that the example methods disclosed throughout the subject specification are capable of being stored on an article of manufacture to facilitate transporting and transferring such methodologies to computers for execution, and thus implementation, by a processor or for storage in a memory.

Figure 17:
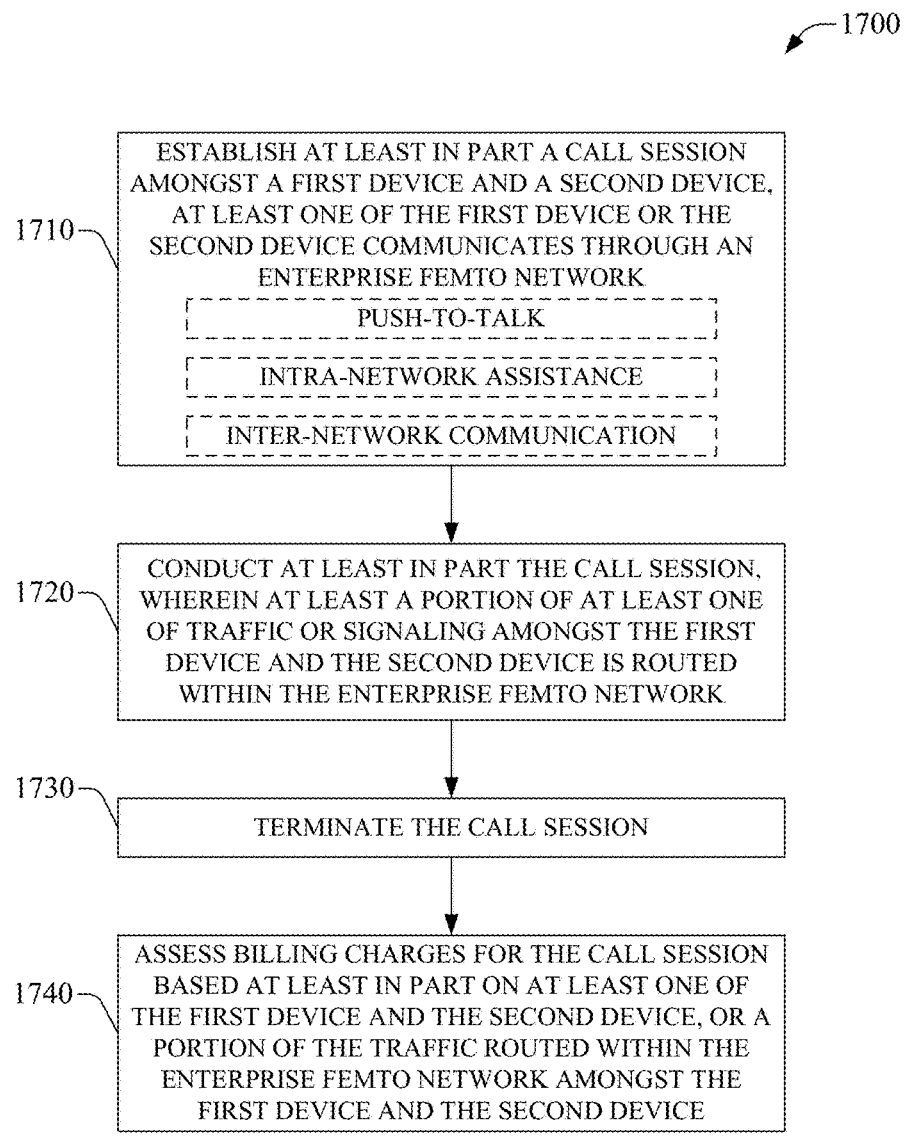
FIG. 17 displays a flowchart of an example method for communicating within a femto mesh network according to aspects disclosed in the subject specification.

FIG. 17 displays a flowchart of an example method 1700 for communicating within a femto mesh network according to aspects disclosed in the subject specification. A routing platform or one or more component therein can enact, or implement, the subject example method 1700. Alternatively or additionally, one or more processors that confer at least part of the functionality of the routing platform can effect the subject example method 1700. At act 1710, a call session is established, at least in part, amongst a first device and a second device. At least one of the first device or the second device communicates through an enterprise femto network. In an aspect, the first device or the second device can be mobile device(s); however, either the first device or the second device can be a stationary device with wireless capabilities, such as a printer, a digital video recorder (DVR) box, an IPTV tuner, a fridge, or the like. In another aspect, the call session can be a push-to-talk session; and intra-network assistance session, wherein either the first of second device is an apparatus that enables customer support; or an inter-network communication. At act 1720, the call session is conducted at least in part, wherein at least a portion of at least one of traffic or signaling amongst the first device and second device is routed within the enterprise femto network. At act 1730, the call session is terminated. Termination can include releasing radio resources allocated within one or more femto APs that enabled, at least in part, the communication amongst the first and second device. In addition, reassigning routing path configuration(s) such as logical addresses, and deactivating radio bearers and packet data protocol (PDP) context(s) also can be included in termination of the call session. Moreover, data buffers or caches can be flushed as part of termination of the call session. At act 1740, billing charges are assessed for the call session based at leas in part on at least one of the first device and the second device, or a portion of the traffic or signaling routed within the enterprise femto network amongst the first device and the second device. Billing charges also can be assessed at least in part based on at least one of customer segments associated, respectively with the first and second device; or promotional campaign(s) related to utilization of enterprise femto network.

Figure 18:
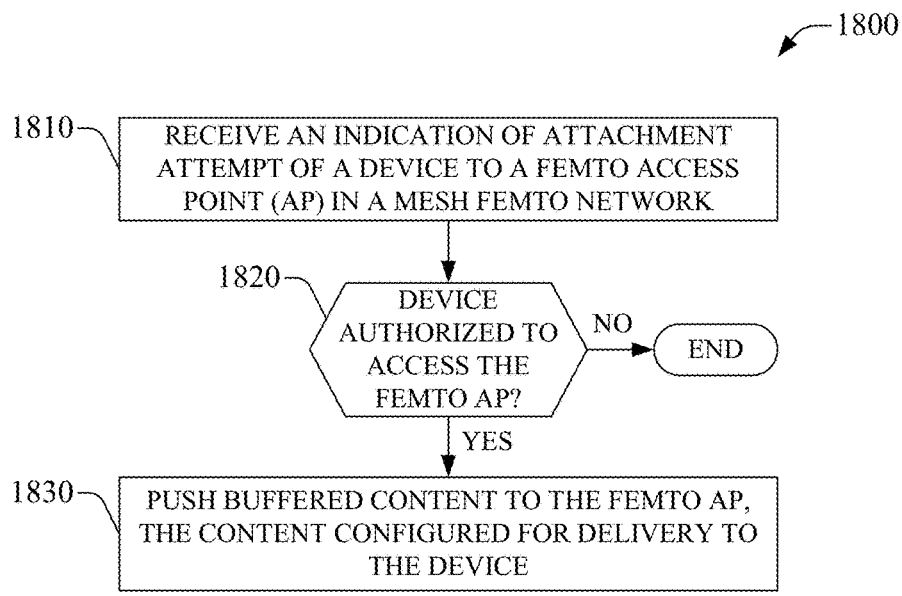
FIG. 18 represents a flowchart of an example method for delivering content within a femto mesh network according to aspects described herein.

FIG. 18 represents a flowchart of an example method 1800 for delivering content within a femto mesh network according to aspects described herein. A routing platform or one or more component therein can enact, or implement, the subject example method 1800. Alternatively or additionally, at least one or more processors that confer at least part of the functionality of the routing platform can effect the subject example method 1800. At act 1810, an indication of attachment attempt of a device to a femto AP in a mesh femto network is received. At act 1820, it is determined if the device is authorized to access the femto AP. In the negative case, the subject example method ends. Conversely, buffered content is pushed to the femto AP at act 1830. The content is configured for delivery to the device; as an example, the content can be a set of digital item(s) such as song album(s), games, books, collection(s) of published articles, or movies, which can be resource-intensive to download OTA. Content can be tagged for delivery to the device by a network operator that administers the femto mesh network at the time of sale of the content(s).

Figure 19:
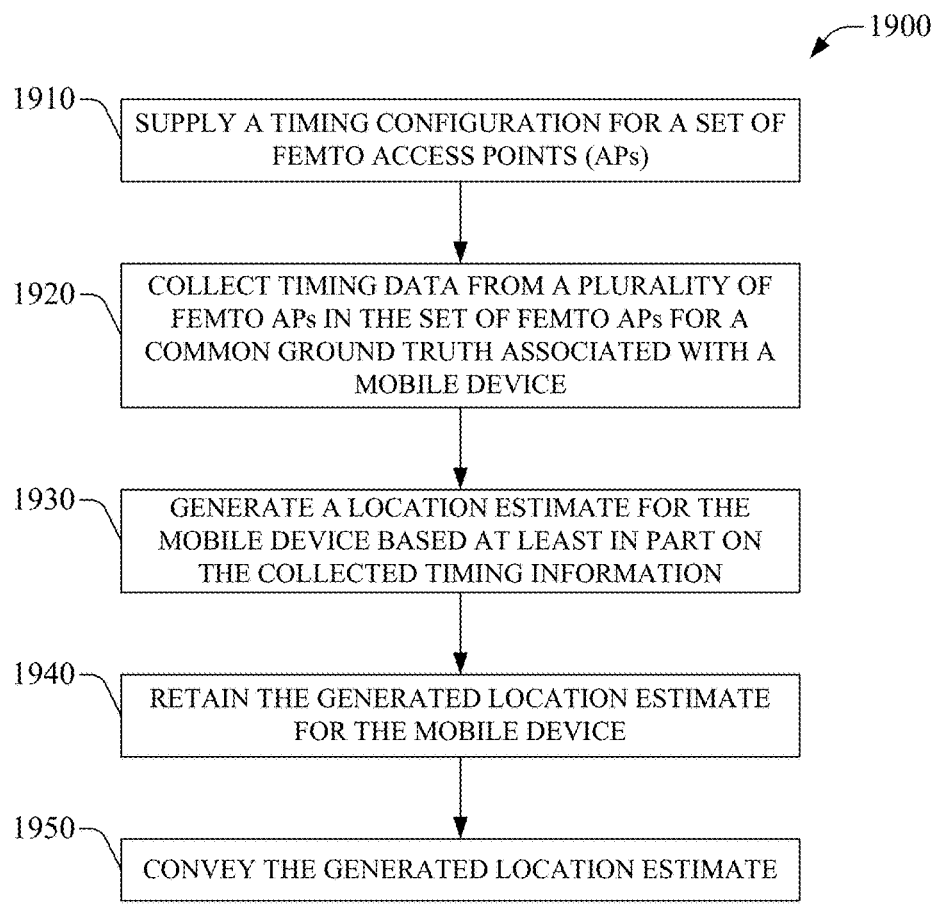
FIG. 19 is a flowchart of an example method for locating a mobile device that operates within a femto network according to aspects described herein.

FIG. 19 is a flowchart of an example method 1900 for locating a mobile device that operates within an enterprise femto network according to aspects described herein. One or more network components within a routing platform can enact, or implement, the subject example method 1900. Alternatively or additionally, at least one or more processors that confer at least part of the functionality of the routing platform can effect the subject example method 1900. At act 1910, timing configuration for a set of femto APs is supplied. Timing configuration can be based on at least one of a set of clock sources selected, for example, through a timing component (e.g., component 407); or timing message(s) generated via a GNSS receiver (e.g., receiver 720). At act 1920, timing data, or propagation timing data, from the set of femto APs is collected for a common ground truth associated with a mobile device. At act 1930, a location estimate for the mobile device is generated based at least in part on the collected timing information, or timing data. At act 1940, the generated location estimate for the mobile device is retained. At act 1950, the location estimate is conveyed.

Figure 20:
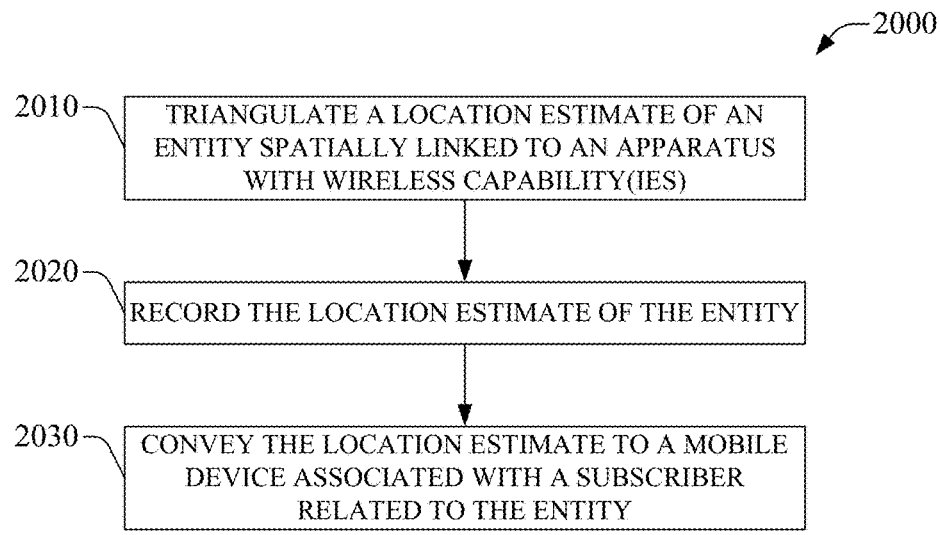
FIG. 20 displays a flowchart of an example method for identifying a location of an entity according to aspects described herein.

FIG. 20 displays a flowchart of an example method 2000 for location identification of an entity according to aspects described herein. One or more network components within a routing platform can enact, or implement, the subject example method 2000. Alternatively or additionally, at least one or more processor(s) that confer at least part of the functionality of the routing platform can effect the subject example method 2000. At act 2010, a location estimate of an entity spatially linked to an apparatus with wireless capability(ies) is triangulated. Criteria to determine if the entity is spatially linked to the apparatus can be established by the one or more networks that can enact the subject example method. At act 2020, the location estimate of the entity is recorded. At act 2030, the location estimate of the entity is conveyed to a mobile device associated with a subscriber related to the entity. The location estimate can be delivered as at least one of a short message service (SMS) communication, an unstructured supplementary service data (USSD) message, or as part of a navigation or location-service application executed in the mobile device.

Figure 21:
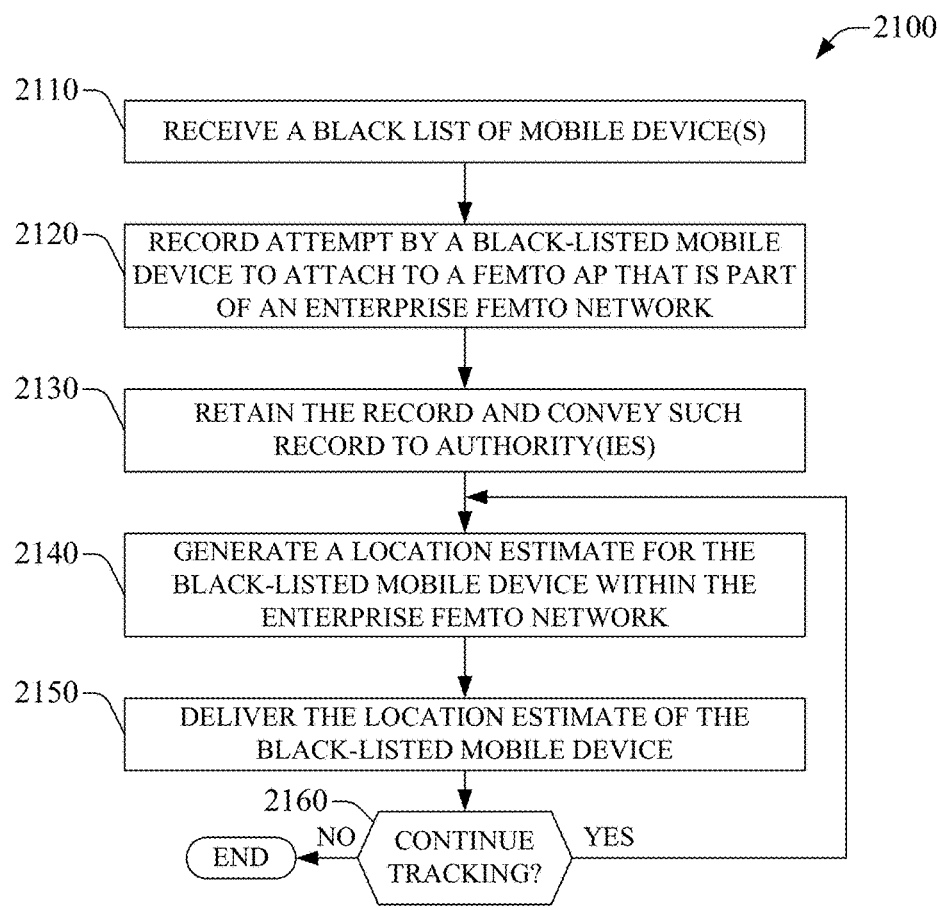
FIG. 21 displays a flowchart of an example method for tracking a location estimate for selected mobile device(s) according to aspects described herein.

FIG. 21 displays a flowchart of an example method 2100 for tracking a location estimate for selected mobile device(s) according to aspects described herein. A routing platform or one or more component therein can enact, or implement, the subject example method 2100. Alternatively or additionally, at least one or more processors that confer at least part of the functionality of the routing platform can effect the subject example method 2100. In an aspect, the subject example method can be part of mechanism for information delivery associated with the Communications Assistance to Law Enforcement Act (CALEA). At act 2110, a black list of mobile device(s) is received. As an example, the mobile device(s) can be an ankle shackle with wireless capability attached to an individual that is a fugitive. As another example, mobile device can be user equipment of a person restricted from accessing the coverage area of an enterprise femto network. As a further example, mobile device(s) can be a subscriber station associated with one or more assailant(s) in a hostage situation within the coverage area of the enterprise femto network. At act 2120, an attempt by a blacklisted device to attach to a femto AP that is part of an enterprise femto network is recorded. Attempted attachment can be part of pilot signal(s) transmission while the blacklisted device is in idle mode, and detection of the pilot signal(s) by the femto AP. At act 2130, the record is retained and conveyed to authority(ies). In an aspect, the authority(ies) can be at least one of one or more law enforcement agencies, or a set of emergency first responders (e.g., paramedics, police officers, special weapons and tactic (SWAT) units).

At act 2140, location of the blacklisted device within the enterprise femto network is generated. In an aspect, generation of the location estimate can proceed in accordance with example subject method 1000. At act 2150, location estimate of the blacklisted device is delivered. As an example, location can be delivered to one or more wearable devices, e.g., a helmet-mounted display, that are part of law-enforcement officers or first emergency responders operations gear or equipment. As another example, location estimate can be provided to an operation control center related to the authority(ies). At act 2160, it is determined if location tracking is to be continued. Various criteria can be employed to determine continuation of location tracking. In the affirmative case, flow is directed to act 2140. Conversely, the subject example method is terminated.

Figure 22:
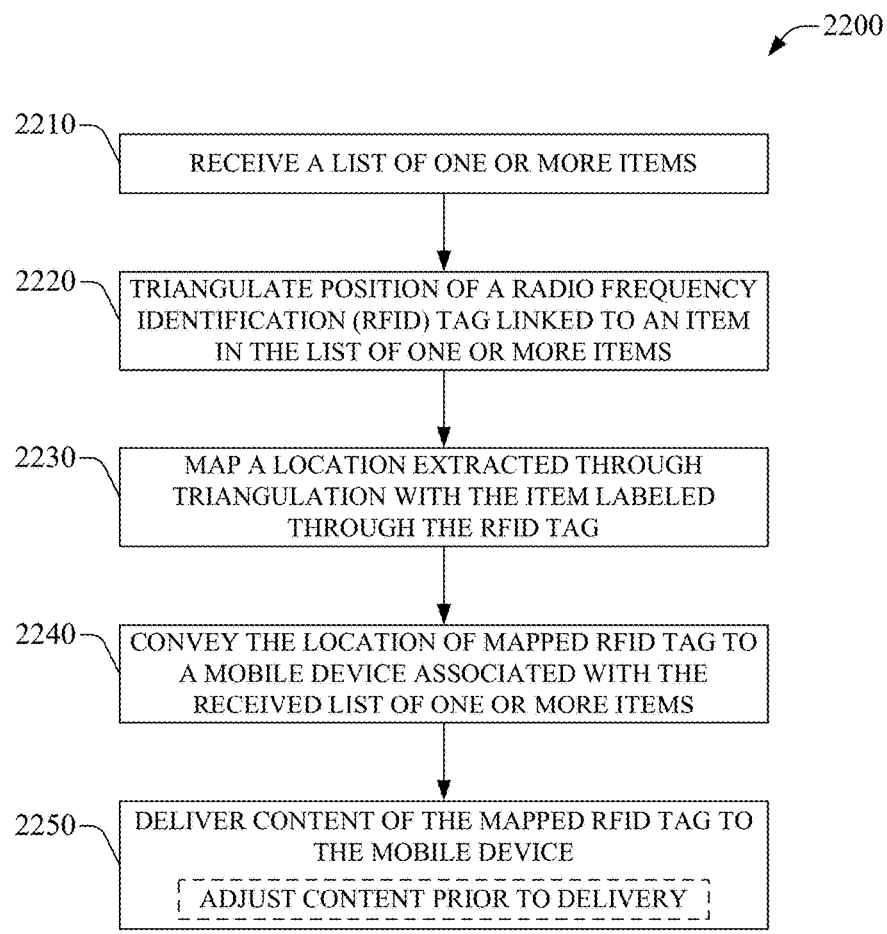
FIG. 22 displays a flowchart of an example method for associating an item with a mobile device according to aspects described herein.

FIG. 22 is a flowchart of an example method 2200 for associating an item with a mobile device according to aspects described herein. The subject example method can be effected by at least one of a femto AP or routing platform. In an aspect, one or more processors that confer functionality to the femto AP or the routing platform can implement, at least in part, the subject example method. At act 2210, a list of one or more items is received. At act 2220, position of an RFID tag linked to an item in the list of one or more items is triangulated. Triangulation of the position can be performed through TOF measurements based on at least one of a predetermined configurable timing advance, or timing information received through a GNSS receiver. At act 2230, a location extracted through triangulation is mapped to the item labeled through the RFID tag. At act 2240, the location of the mapped RFID tag is conveyed to a mobile device associated with the received list of one or more items; for instance, the mobile device can be linked to a subscriber that generated the list. In an aspect, a femto network platform relaying the list or a network external the femto network platform can exploit subscriber information to link unique identifier of the mobile device to credentials, e.g., password(s) or passkey(s), employed by the subscriber to access a service or application that enables generation of the list of one or more items. At act 2250, content of the mapped RFID tag is delivered to the mobile device. Delivering the content can include adjusting the content prior to delivery, such adjustment can allow to customize features of the content such as pricing of the item labeled through the RFID tag.

Figure 23:
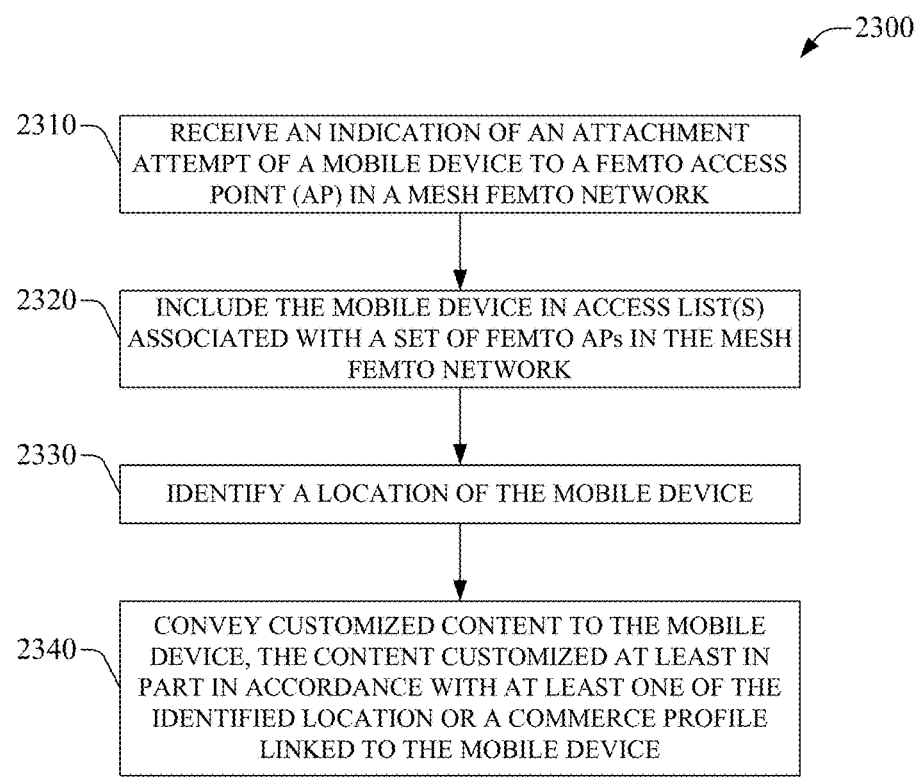
FIG. 23 is a flowchart of an example method for supplying custom content according to aspects described herein.

FIG. 23 is a flowchart of an example method 2300 for supplying custom promotional content according to aspects described herein; the promotional content can include at least one of monetary incentive(s) or coupon(s), or advertisement. One or more network components such as a routing platform or a commerce component 1140, or one or more components therein, can implement the subject example method 2300. Alternatively or additionally, one or more processors that confer at least part of the functionality of the routing platform can implement the subject example method 2300. At act 2310, an indication of an attachment attempt of a mobile device to a femto AP in a mesh femto network, or enterprise femto network, is received. At act 2320, the mobile device is included in access list(s) associated with a set of femto APs in the mesh femto network. In an aspect, an access list management component within a routing platform that can enact, at least in part, the subject example method, can configure or populate the access list(s). At act 2330, a location of the mobile device is identified. Identification of the location can proceed in accordance at least in part with example method 1900 described herein. At act 2340, content customized at least in part in accordance with at least one of the identified location or a commerce profile linked to the mobile device is conveyed to the mobile device.

Figure 24:
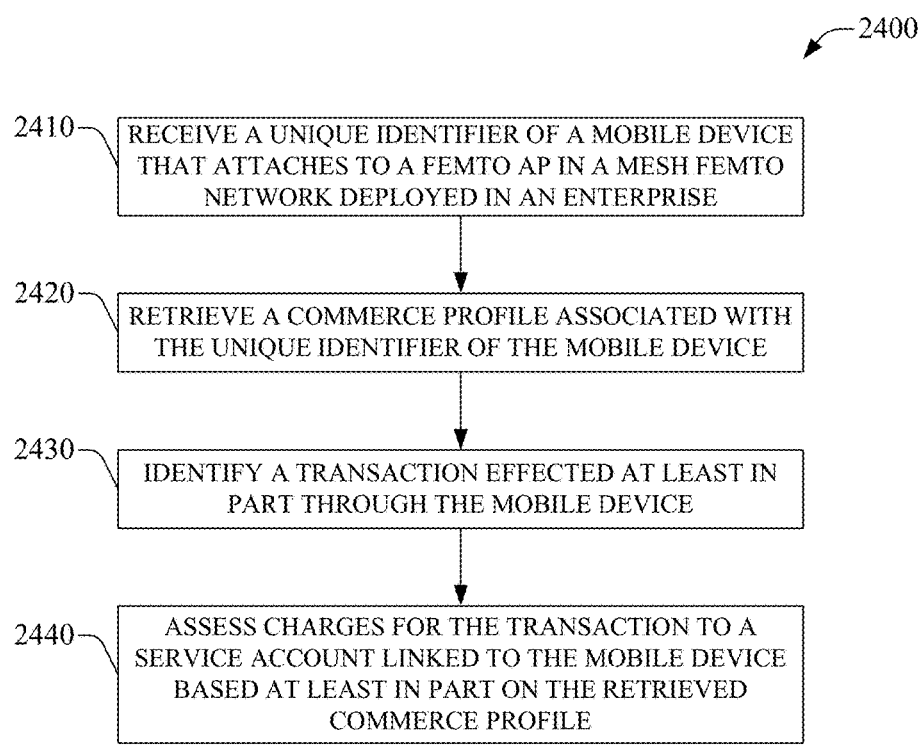
FIG. 24 is a flowchart of an example method for effecting a commercial transaction at least in part through an enterprise femto network according to aspects described herein.

FIG. 24 is a flowchart of an example method 2400 for effecting a commercial transaction at least in part through an enterprise femto network according to aspects described herein. A commerce component or one or more component therein can enact, or implement, the subject example method 2400. Alternatively or additionally, one or more processors that confer at least part of the functionality of the routing platform can effect the subject example method 2400. At act 2410, a unique identifier of a mobile device that attaches to a femto AP in a mesh femto network deployed in an enterprise. At act 2420, retrieve a commerce profile associated with the unique identifier of the mobile device. At act 2430, a transaction effected at least in part through the mobile device is identified. At act 2440, charges for the transaction are assessed to a service account linked to the mobile device based at least in part on the retrieved commerce profile and information therein. The assessment of charges includes accounting for accrued monetary incentives or coupon(s) associated with the mobile device.

Figure 25:
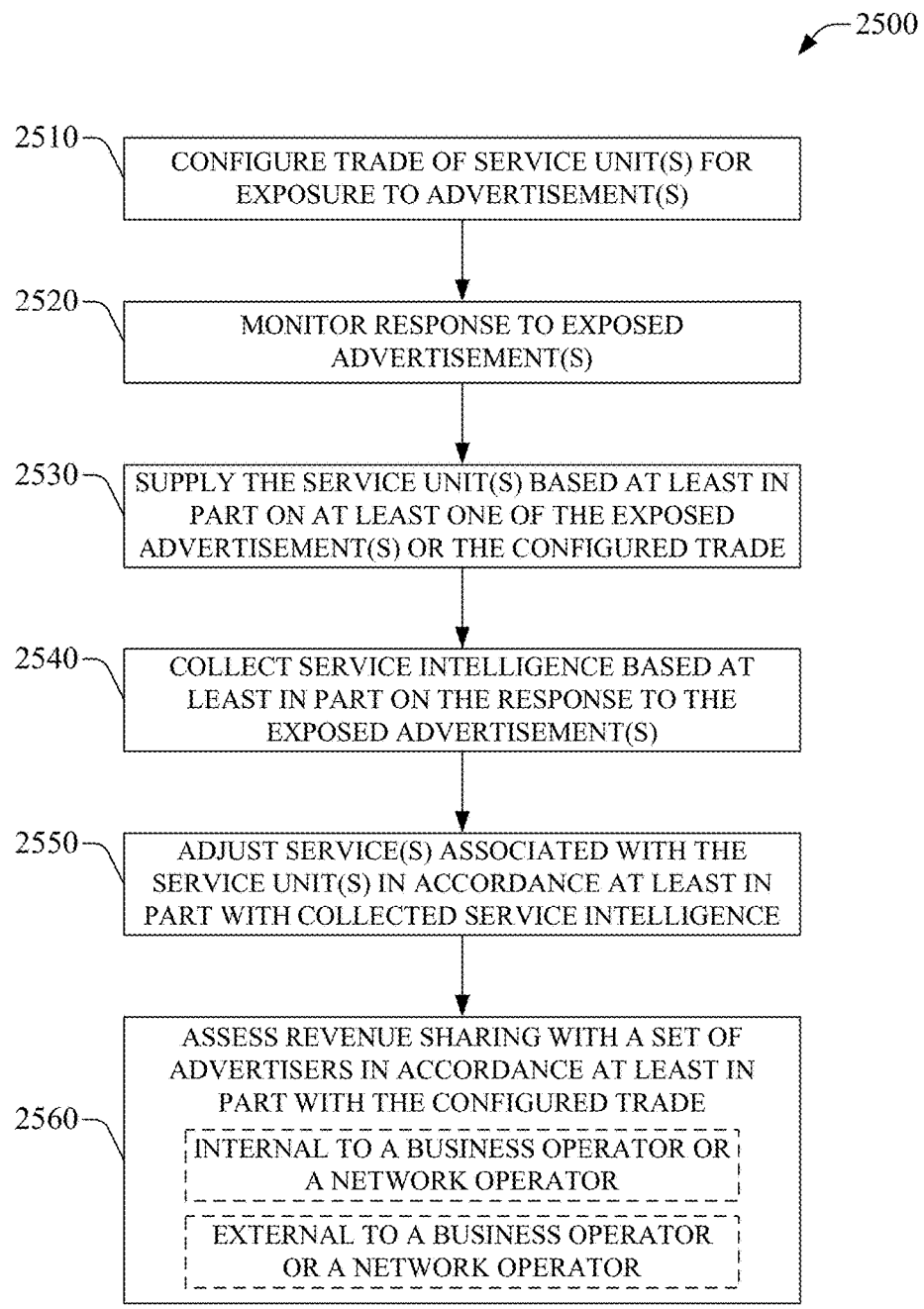
FIG. 25 displays a flowchart of an example method developing business intelligence through advertisement within an enterprise femto network according to aspects described herein.

FIG. 25 displays a flowchart of an example method 2500 for developing business intelligence through advertisement within an enterprise femto network according to aspects described herein. One or more network components such as commerce component 1140 or routing platform 1110 can enact the subject example method 2500. In an aspect, at least one or more processor(s) that confer functionality to the network component can implement, at least in part, the subject example method 2500. At act 2510, trade of service unit(s) for exposure to advertisement(s) is configured. Configuration can include rate of exchange of service unit(s) for advertisement(s) type. For instance, direct response advertisement can provide a higher volume of traded service units than advertisement directed to brand development or product penetration. At act 2520, response to exposed advertisement(s) is monitored. In an aspect, monitoring can be accomplished through collection of transaction information directly related to the exposed advertisement(s). At act 2530, the service unit(s) are supplied based at least in part on at least one of the exposed advertisement(s) or the configured trade. Service unit(s) can be credited to an service account associated with a subscriber exposed to the advertisement(s) or can be redeemed as coupons or vouchers when a commercial transaction related at least in part to the advertisement(s) is effected.

At act 2540, based at least in part on response to the exposed advertisement(s), service intelligence is collected. At act 2550, service(s) associated with the service unit(s) is adjusted in accordance at least in part with the collected service intelligence. For instance, if a rate of action linked to a specific class of advertisement(s) and related first type of service unit(s), e.g., text message(s), ringtone(s), song(s), is higher compared to action elicited through the specific class of advertisement(s) when linked to a second type of service unit(s), e.g., stock-market trade instance, a service provider can generate a service or a product based at least in part on the first type of service unit(s). At act 2560, revenue sharing with a set of advertisers is assessed in accordance at least in part with the configured trade. Advertisers can be internal or external, or a combination thereof, to a network operator that administers the enterprise femto network. In an example, an internal advertiser can be a business department or a portion thereof that develops new product(s) or researches subscriber commercial behavior. In another example, external advertisers can include clients, vendors, or business partners of the network operator.

Figure 26:
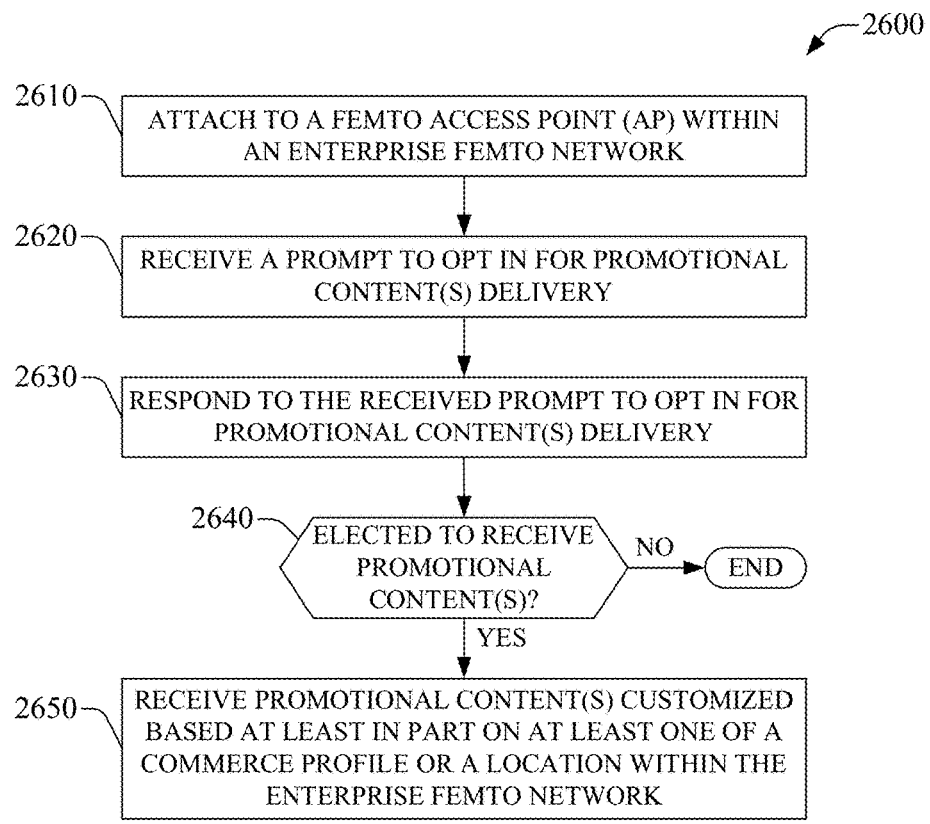
FIG. 26 displays a flowchart of an example method for consuming promotional content(s) according to aspects described herein.

FIG. 26 displays a flowchart of an example method 2600 for consuming promotional content(s) according to aspects described herein. Promotional content(s) can include advertisement or incentive(s) such as coupon(s). A mobile device can enact the subject example method 2600. In an aspect, at least one or more processor(s) that confer functionality to the mobile device can implement, at least in part, the subject example method 2600. At act 2610, attachment to a femto AP within an enterprise network is effected. For instance, the femto AP can be an access point that covers at least in part a point of entry entrance to a coverage area of the enterprise femto network (see FIG. 9). At act 2620, a prompt to opt in for promotional content(s) delivery is received. In an aspect, the prompt can be embodied in at least one of a SMS communication, an MMS communication, a USSD message, an email message, or an IM message. At act 2630, a response to the received prompt is effected. Responding to the received prompt can include conducting a cost-utility analysis to determine a financial gain from receiving a predetermined volume of promotional content(s), e.g., coupons or monetary incentives, with respect to a cost of receiving the predetermined volume of promotional content(s). The cost can include a battery drain or battery charge consumption level of the mobile device that enacts the subject example method. At act 2640 it is determined if it has been elected to receive promotional content(s). Such determination can be enabled by at least one of a variable, logic or otherwise, or an entry in a configuration file retained in memory of the mobile device that enacts the subject example method. At act 2650, promotional content(s) are received, wherein the promotional content(s) are customized based at least in part on at least one of a commerce profile or a location within the enterprise femto network.

Figure 27:
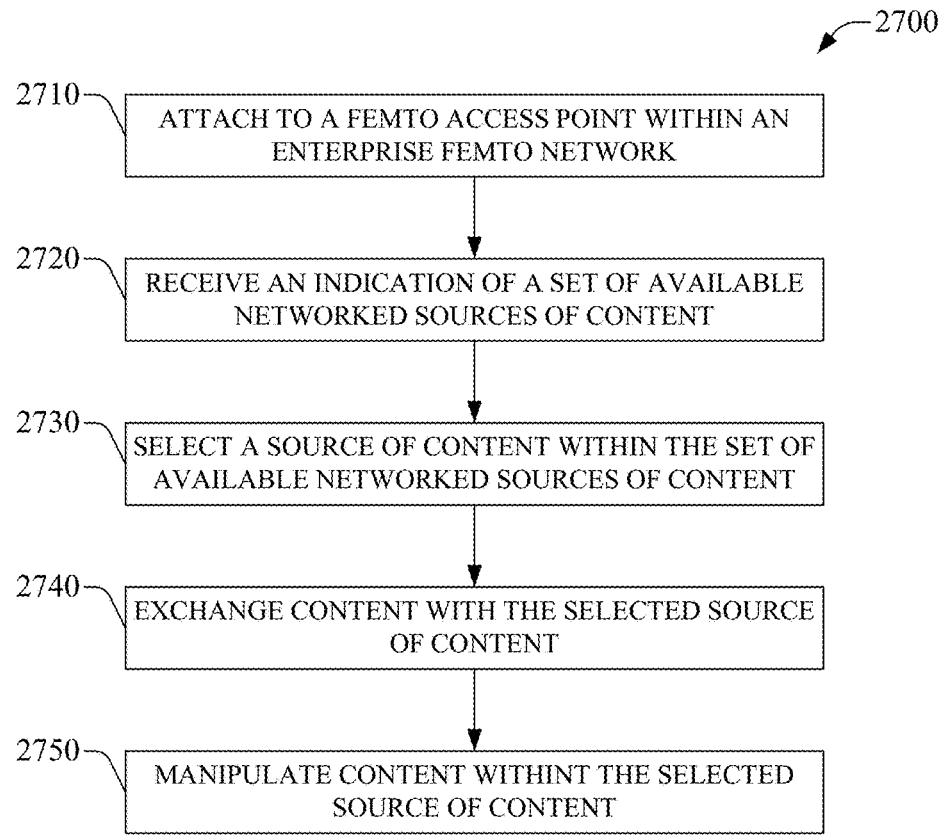
FIG. 27 displays a flowchart of an example method for administering content within an intra-premises network that is part of an enterprise femto network according to aspects described herein.

FIG. 27 displays a flowchart of an example method 2700 for administering content within an intra-premises network that is part of an enterprise femto network according to aspects described herein. A mobile device can enact the subject example method 2700. In an aspect, at least one or more processor(s) that confer functionality to the mobile device can implement, at least in part, the subject example method 2700. At act 2710, attachment to a femto AP within an enterprise femto network is effected. At act 2720, an indication of a set of available networked sources of content is received. The available networked sources can include a set of devices or servers within the intra-premises network. Data mass storage also can be part of the networked sources of content. The indication can be received through a graphical user interface (GUI) rendered as part of a display interface that is included within the mobile device that enacts the subject example method Alternatively or additionally, the indication can be received as an SMS communication, a MMS communication, an IM, an email message, or the like. Moreover, or as another alternative, the indication can be received through aural indicia.

At act 2730, a source of content within the set of available networked sources of content is selected. In an aspect, selection can be effected through data entry in within a display interface that is part of the mobile device that can enact the subject example method. At act 2740, content is exchanged with the selected source of content. Exchange of content includes pushing content from the mobile device that enacts the subject example method to the selected source of content, e.g., a device such as an IPTV or a digital picture frame within a home network. The content can be pushed wirelessly to the femto AP that is part of the enterprise femto network and that the mobile device that enacts the subject example method is authorized to access, e.g., as determined by an access list, or white list. The femto AP relays the received content to a routing platform, e.g., 1110, that is functionally connected to an intra-premises network that includes the source of content. It is noted that for selected sources of content that have wireless capability, exchanging content can comprise including the selected source of content within an access list linked to the femto AP that receives content form the mobile device, and conveying the content OTA from the femto AP to the selected source of content. At act 2750, content within the selected source of content can be manipulated. Manipulation of content includes deletion, addition, or edition of files, digital documents such as songs, movies, photos, or the like.

Figure 28:
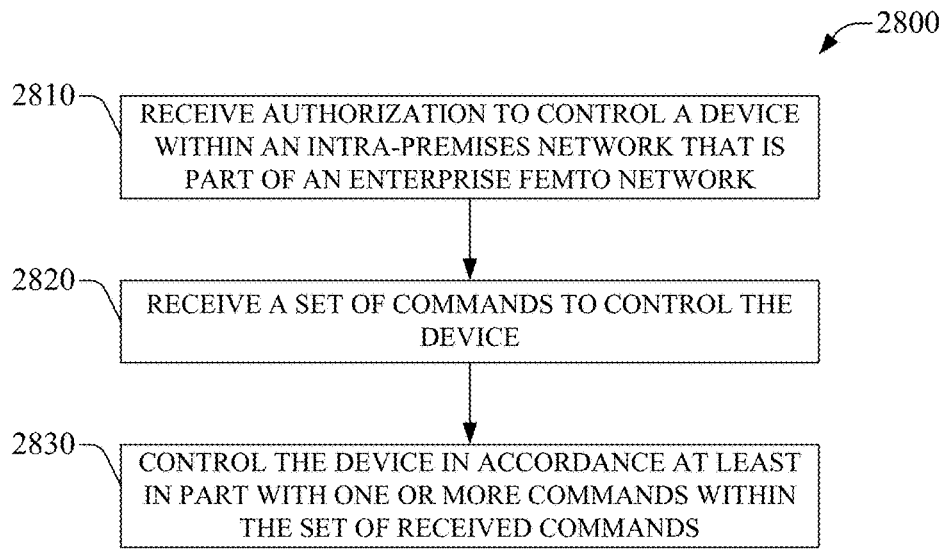
FIG. 28 illustrates a flowchart of an example method for controlling a device that is part of an intra-premises network functionally connected to an enterprise femto network according to aspects described herein.

FIG. 28 illustrates a flowchart of an example method 2800 for controlling a device that is part of an intra-premises network functionally connected to an enterprise femto network according to aspects described herein. A mobile device can enact the subject example method 2800. In an aspect, at least one or more processor(s) that confer functionality to the mobile device can implement, at least in part, the subject example method 2800. At act 2810, authorization to control a device within an intra-premises network that is part of the enterprise network is received. Authorization can be received OTA via a femto AP that can serve the mobile device that enacts the subject example method. At act 2820, a set of commands to control the device is received. The scope, e.g., type and number, of the set of commands can be based at least in part on the mobile device that receives the set of commands or a subscriber linked to the mobile device. At act 2830, the device is controlled in accordance at least in part with one or more commands within the set of received commands.

Figure 29:
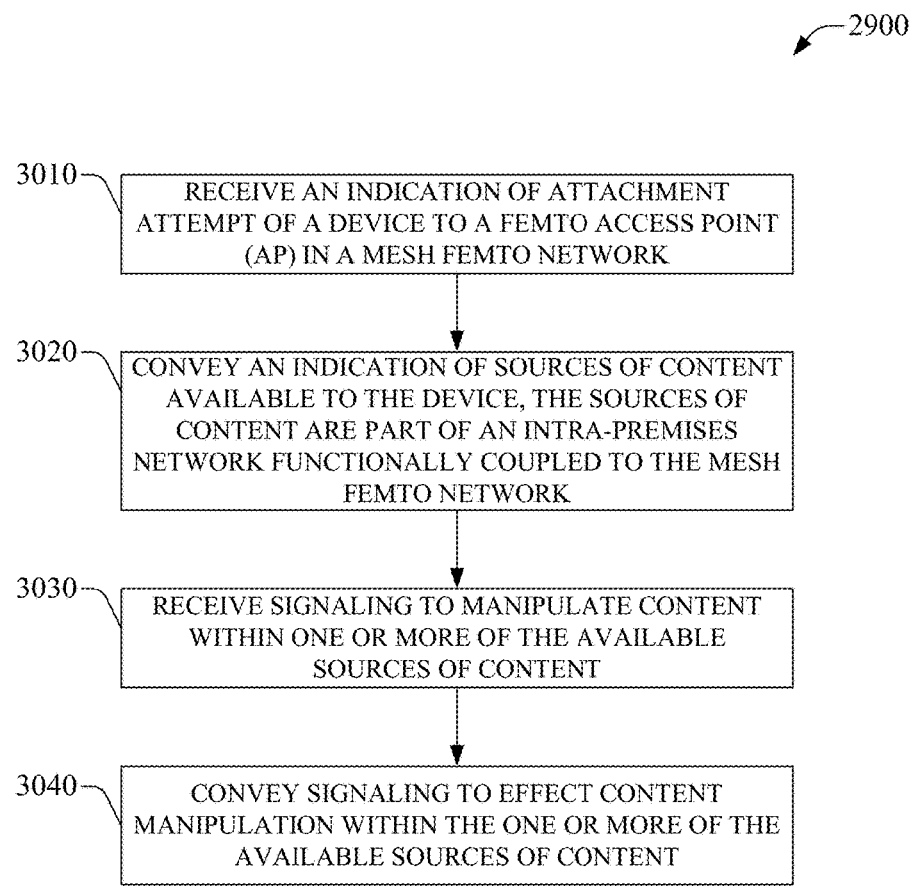
FIG. 29 is a flowchart of an example method for administering content within an intra-premises network that is part of an enterprise femto network, or mesh femto network, according to aspects described herein.

FIG. 29 is a flowchart of an example method 2900 for administering content within an intra-premises network that is part of an enterprise femto network, or mesh femto network, according to aspects described herein. One or more network components such as routing platform 1110 can enact the subject example method 2900. In an aspect, at least one or more processor(s) that confer functionality to the network component can implement, at least in part, the subject example method 2900. At act 2910, an indication of attachment attempt of a device to a femto AP in a mesh femto network is received. At act 2920, an indication of sources of content available to the device are conveyed, the sources of content are part of the intra-premises network functionally coupled to the mesh femto network. At act 2930, signaling to manipulate content within one or more of the available sources of content is received. At act 2940, signaling to effect content manipulation within the one or more of the available sources of content is conveyed.

Figure 30:
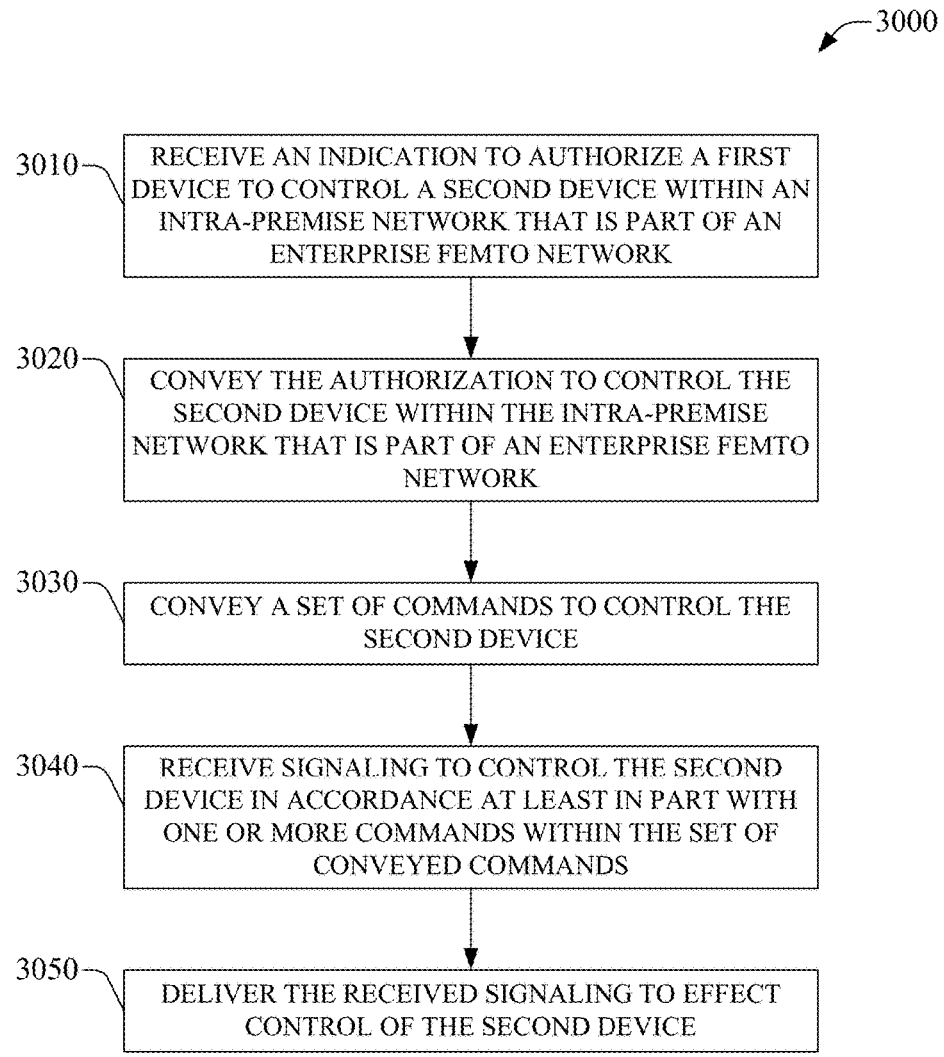
FIG. 30 displays a flowchart of an example method for controlling of a device within an intra-premises network to a disparate device according to aspects described herein.

FIG. 30 displays a flowchart of an example method 3000 for allowing control of a device within an intra-premises network to a disparate device according to aspects described herein. One or more network components such as, for example, routing platform 1110 can enact the subject example method 3000. In an aspect, at least one or more processor(s) that confer functionality to the network component can implement, at least in part, the subject example method 3000. At act 3010, an indication to authorize a first device to control a second device within the intra-premises network is received; the intra-premises network is part of, or functionally coupled to, an enterprise femto network. At act 3020, the authorization to control the second device within the intra-premises network is conveyed. At act 3030, a set of commands to control the second device is conveyed. At act 3040, signaling to control the second device in accordance at least in part with the one or more commands within the set of conveyed commands is received. At act 3050, the received signaling is delivered to effect control of the second device.

Figure 31:
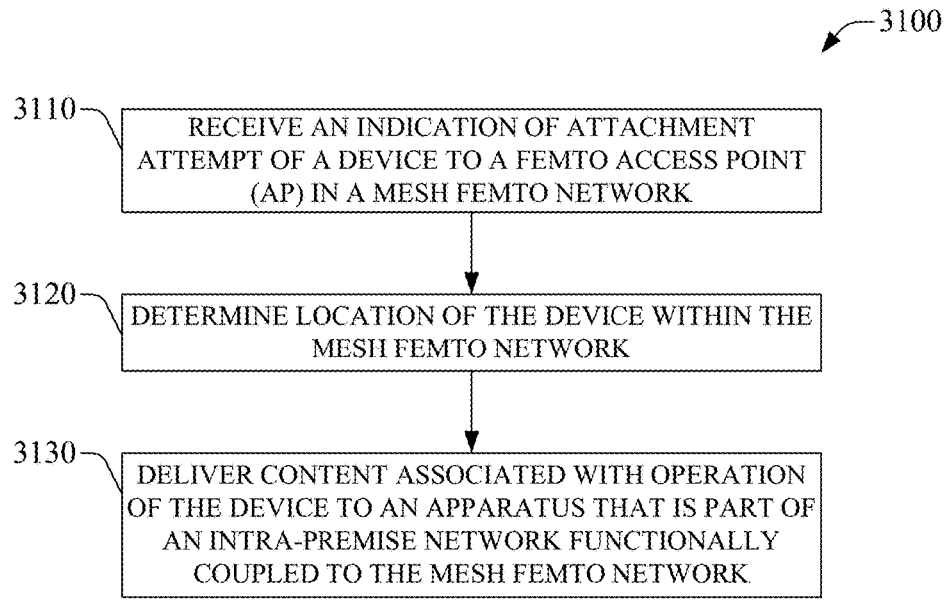
FIG. 31 displays a flowchart of an example method for supplying content to a mobile device within a mesh femto network, or enterprise femto network, according to aspects described herein.

FIG. 31 displays a flowchart of an example method 3100 for supplying content to a mobile device within a mesh femto network, or enterprise femto network, according to aspects described herein. One or more network components such as, for example, routing platform 1110 can enact the subject example method 3100. In an aspect, at least one or more processor(s) that confer functionality to the network component can implement, at least in part, the subject example method 3100. At act 3110, an indication of attachment attempt of a device to a femto AP in a mesh femto network is received. At act 3120, location of the device within the mesh femto network is determined. Location can be determined in accordance with aspects described herein. At act 3130, content associated with operation of the device is delivered to an apparatus that is part of an intra-premises network functionally coupled to the mesh femto network. As an illustration, the device can be a handset of a resident of a home in which the mesh femto network is deployed. When a phone call is received at the handset, caller identification can be conveyed to an IPTV set that can be part of a network of equipment, e.g., devices 1142, deployed within the home. In an aspect, display of caller identification can proceed after a predetermined period of unresponsiveness to the phone call received at the handset.

Figure 32:
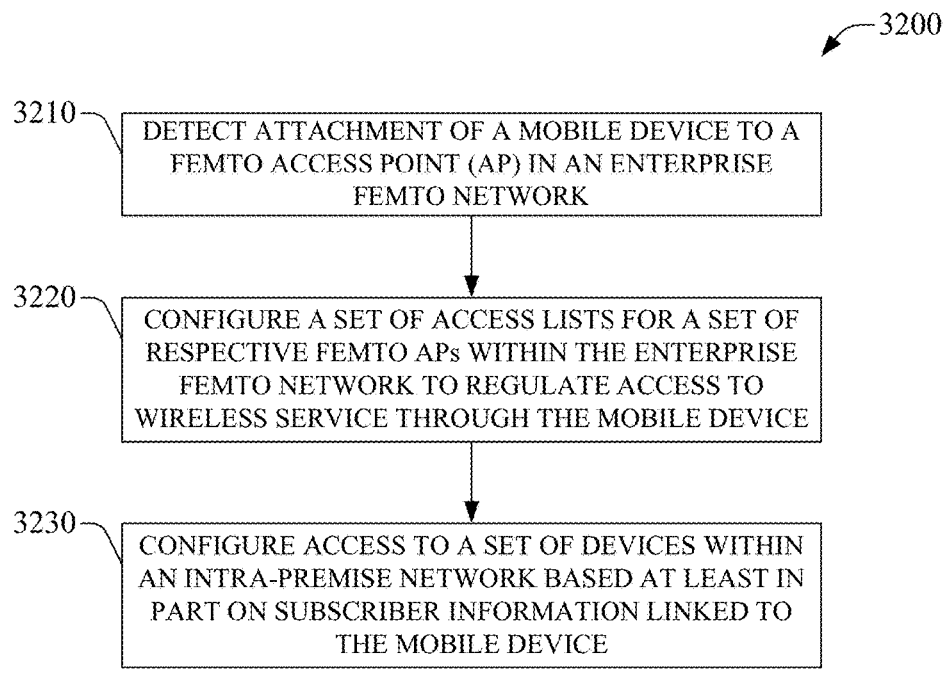
FIG. 32 displays a flowchart of an example method for regulating access to equipment that is part of an intra-premises network functionally coupled to an enterprise femto network, according to aspects described herein.

FIG. 32 displays a flowchart of an example method 3200 for regulating access to equipment that is part of an intra-premises network functionally coupled to an enterprise femto network, according to aspects described herein. One or more network components such as, for example, routing platform 1110 or security component 1510 can enact the subject example method 3200. In an aspect, at least one or more processor(s) that confer functionality to the network component can implement, at least in part, the subject example method 3200. At act 3210, attachment of a mobile device to a femto AP in an enterprise femto network is detected. At act 3220, a set of access lists for a set of respective femto APs within the enterprise femto network is configured to regulate access to wireless service through the mobile device. In an aspect, regulation can depend at least in part on the location of the femto AP for which the access list is configured. For instance, when the femto enterprise femto network is deployed in a hospital, voice and data service can be allowed in a lobby or waiting area, whereas only data may be allowed within bedroom(s) in a maternity section. In another aspect, configured access lists can regulate availability of specific services; for instance, instant messaging or texting application can be excluded from service. Such configuration can be advantageous in setting in which attention to detail can be mission critical and thus distraction generated via texting or other activities is to be mitigated.

At act 3230, access to a set of devices within an intra-premises network is configured based at least in part on subscriber information linked to the mobile device. Such access can be part of a security profile that controls, at least in part, operation of devices within the intra-premises network. As an example, when the intra-premises network comprised a set of manufacturing equipment, access to certain pieces of the manufacturing equipment can be declined to inexperienced end users, or end users with inadequate privileges to operate the equipment or be exposed to data produced by the equipment.

Figure 33:
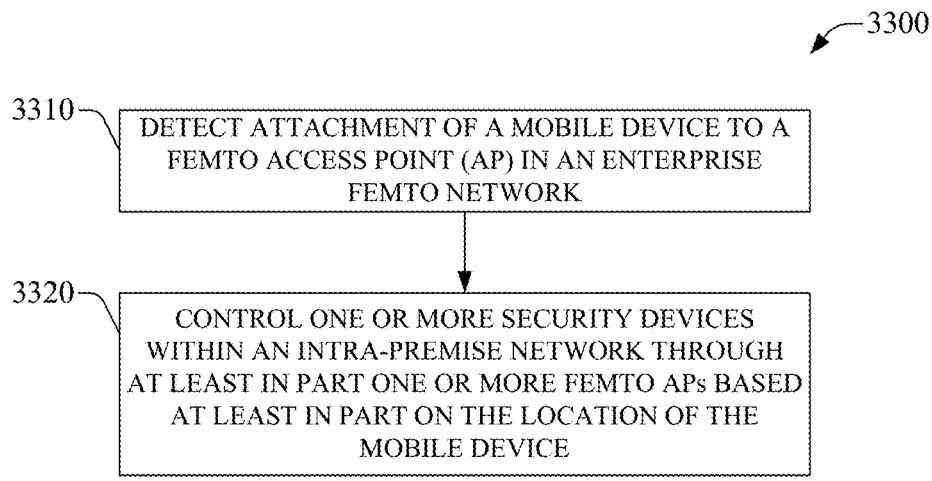
FIG. 33 displays a flowchart of an example method for supplying content to a mobile device within a mesh femto network, or enterprise femto network, according to aspects described herein.

FIG. 33 displays a flowchart of an example method 3300 for supplying content to a mobile device within a mesh femto network, or enterprise femto network, according to aspects described herein. One or more network components such as, for example, routing platform 1110 or security component 1510 can enact the subject example method 3300. In an aspect, at least one or more processor(s) that confer functionality to the network component can implement, at least in part, the subject example method 3300. At act 3310, attachment of a mobile device to a femto AP in an enterprise network is detected. At act 3320, one or more security devices within the intra-premises network are controlled at least in part through one or more femto APs based at least in part on the location of the mobile device. Control can be accomplished via communication of signaling that conveys directives for operation of the security devices, e.g., a set of cameras sensitive to visible or IR light.

Figure 34:
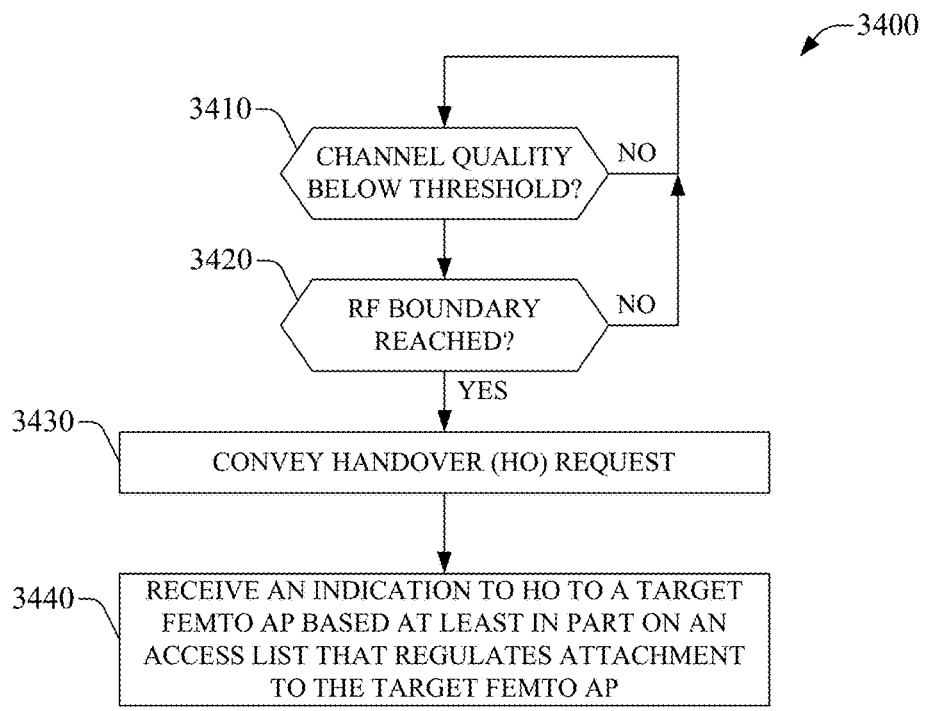
FIG. 34 represents a flowchart of an example method for handing off a mobile device within coverage areas within a femto enterprise network according to aspects described herein.

FIG. 34 is a flowchart of an example method 3400 for handing off a mobile device within coverage areas within a femto enterprise network according to aspects described herein. The subject example method can be effected by at least one of a femto AP or routing platform. In an aspect, at least one or more processor(s) that confer functionality to the femto AP or the routing platform can implement, at least in part, the subject example method 3400. At act 3410, it is evaluated if channel quality is below threshold. Channel quality can include FL and RL signal strength. In the negative case, evaluation is re-enacted. In the affirmative case, flow is directed to act 3420, in which it is probed whether an RF boundary is reached. A negative outcome results in flow being directed to act 3410. Conversely, a positive outcome results in conveying a handover request at act 3430. The RF boundary can be configurable and established in accordance at least in part with at least one of a schedule or one or more operation condition(s) of the femto enterprise network, wherein operation condition(s) can include at least one of network load such as number of served mobile devices; other-femto interference; available bandwidth; or channel quality. At act 3440, an indication to HO to a target femto AP is received based at least in part on an access list that regulated attachment to the target femto AP.

Figure 35:
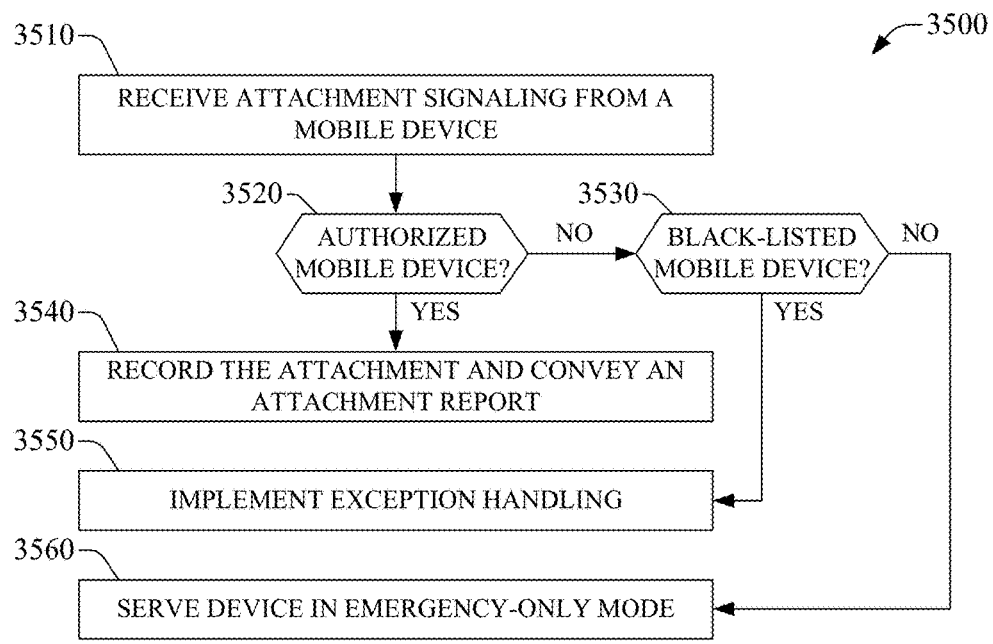
FIG. 35 displays a flowchart of an example method for signaling to a routing platform an attachment of a wireless device to a femto access point in a femto enterprise network according to aspects described herein.

FIG. 35 displays a flowchart of an example method 3500 for signaling to a routing platform an attachment of a wireless device to a femto access point in a femto enterprise network according to aspects described herein. A femto AP (e.g., femto $104_3$) functionally linked to a routing platform (e.g., 110 or 510) in a femto enterprise network as described herein can enact, or implement the subject example method. In an aspect, at least one or more processor(s) that confer functionality to the femto AP can implement, at least in part, the subject example method 3500. At act 3510 attachment signaling is received from a mobile device, the attachment signaling can include wireless pilot signal(s) which can be conveyed when the mobile device operates in idle mode. At act 3520, it is determined if the mobile device is authorized to access service through a femto AP, which can be the femto AP that enacts the subject example method. Authorization or access privilege(s) can be determined by an access list, e.g., access list(s) 353, that regulates at least a level of service provide to user equipment through the femto AP. When the mobile device is authorized, the attachment is recorded, e.g., as part of access record(s) 355, and an attachment report is conveyed at act 3540. In an aspect, the attachment report can deliver registration information such as a time stamp, UE identifier codes or tokens, or the like. A conveyed attachment report can be aggregated at the routing platform functionally linked to the femto AP that can enact the subject example method. Conversely, when the mobile device is not authorized, flow is directed to act 3530 in which it is established whether the mobile device is a blacklisted device. In the affirmative case, exception handling is implemented at act 3550. Exception handling can include delivering an alarm, e.g., a SMS communication, a USSD code, an email message, an instant message, etc., to an authority such as a law-enforcement agency. In the negative case, the mobile device is served in emergency-mode only at act 3560.

Figure 36:
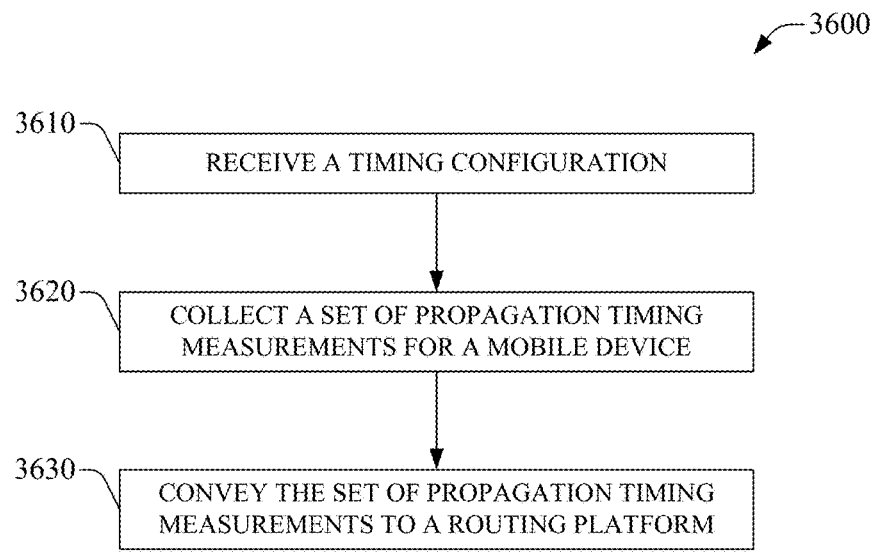
FIG. 36 is a flowchart of an example method for assisting localization of a mobile device that operates in the femto enterprise according to aspects described herein.

FIG. 36 is a flowchart of an example method 3600 for assisting localization of a mobile device that operates in the femto enterprise network according to aspects described herein. A femto AP (e.g., femto 104₃) functionally linked to a routing component (e.g., 110 or 510) in a femto enterprise network as described herein can enact, or implement the subject example method 3600. Alternatively or additionally, at least one or more processor(s) that confer functionality to the femto AP can implement, at least in part, the subject example method. At act 3610, a timing configuration is received. The timing configuration can synchronize time amongst a set of femto APs in a femtocell mesh network. In addition, the timing configuration can enable selection of a clock source, which can be part of a clock layer, e.g., 445, that determines a spatially resolution that can be attained through triangulation based at least in part on TOF measurements that can be effected by the femto AP the implements the subject example method. At act 3620, a set of propagation timing measurements is collected. The set includes one or more measurements. At act 3630, the set of timing measurements is conveyed to a routing platform. In an aspect, the routing platform can exploit timing data to generate a location estimate of a mobile device or an entity linked to an apparatus with wireless capability.

Figure 37:
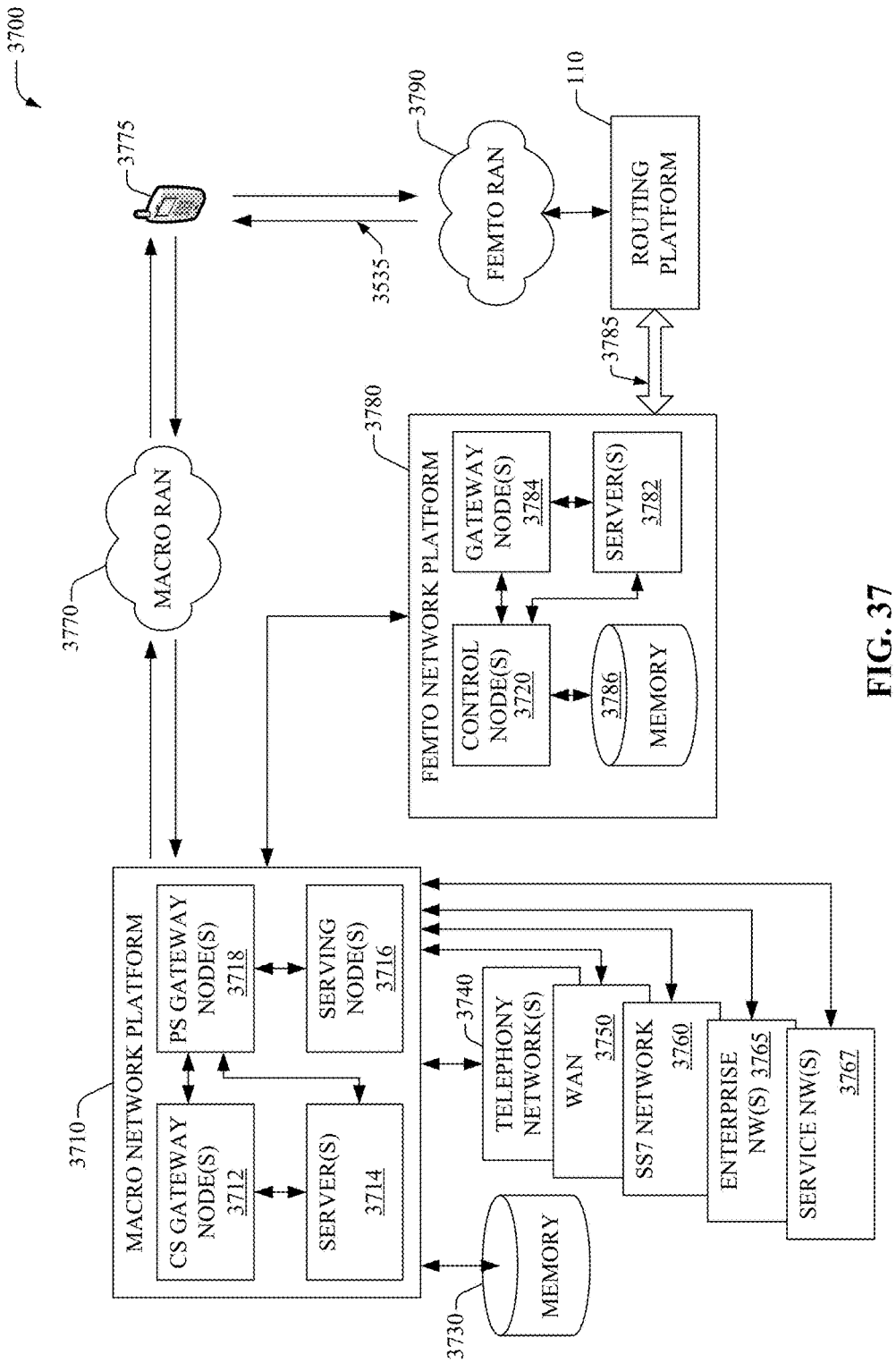
FIG. 37 illustrates an example wireless communication environment with associated components that can enable operation of a femtocell enterprise network in accordance with aspects described herein.

To provide further context for various aspects of the subject specification, FIG. 37 illustrates an example wireless communication environment 3700, with associated components that can enable operation of a femtocell enterprise network in accordance with aspects described herein. Wireless communication environment 3700 includes two wireless network platforms: (i) A macro network platform 3710 that serves, or facilitates communication) with user equipment 3775 via a macro radio access network (RAN) 3770. It should be appreciated that in cellular wireless technologies (e.g., 4G, 3GPP UMTS, HSPA, 3GPP LTE, 3GPP UMB), macro network platform 3710 is embodied in a Core Network. (ii) A femto network platform 3780, which can provide communication with UE 3775 through a femto RAN 3790, linked to the femto network platform 3780 through a routing platform 102 via backhaul pipe(s) 3785, wherein backhaul pipe(s) are substantially the same a backhaul link 3853 below. It should be appreciated that femto network platform 3780 typically offloads UE 3775 from macro network, once UE 3775 attaches (e.g., through macro-to-femto handover, or via a scan of channel resources in idle mode) to femto RAN.

It is noted that RAN includes base station(s), or access point(s), and its associated electronic circuitry and deployment site(s), in addition to a wireless radio link operated in accordance with the base station(s). Accordingly, macro RAN 3770 can comprise various coverage cells like cell 1205, while femto RAN 3790 can comprise multiple femto access points. As mentioned above, it is to be appreciated that deployment density in femto RAN 3790 is substantially higher than in macro RAN 3770.

Generally, both macro and femto network platforms 3710 and 3780 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject application, macro network platform 3710 includes CS gateway node(s) 3712 which can interface CS traffic received from legacy networks like telephony network(s) 3740 (e.g., public switched telephone network (PSTN), or public land mobile network (PLMN)) or a SS7 network 3760. Circuit switched gateway 3712 can authorize and authenticate traffic (e.g., voice) arising from such networks. Additionally, CS gateway 3712 can access mobility, or roaming, data generated through SS7 network 3760; for instance, mobility data stored in a VLR, which can reside in memory 3730. Moreover, CS gateway node(s) 3712 interfaces CS-based traffic and signaling and gateway node(s) 3718. As an example, in a 3GPP UMTS network, gateway node(s) 3718 can be embodied in gateway GPRS support node(s) (GGSN).

In addition to receiving and processing CS-switched traffic and signaling, gateway node(s) 3718 can authorize and authenticate PS-based data sessions with served (e.g., through macro RAN) wireless devices. Data sessions can include traffic exchange with networks external to the macro network platform 3710, like wide area network(s) (WANs) 3750; it should be appreciated that local area network(s) (LANs) can also be interfaced with macro network platform 3710 through gateway node(s) 3718. Gateway node(s) 3718 generates packet data contexts when a data session is established. To that end, in an aspect, gateway node(s) 3718 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 3714. It is to be noted that in 3GPP UMTS network(s), gateway node(s) 3718 (e.g., GGSN) and tunnel interface (e.g., TTG) comprise a packet data gateway (PDG).

Macro network platform 3710 also includes serving node(s) 3716 that convey the various packetized flows of information or data streams, received through gateway node(s) 3718. As an example, in a 3GPP UMTS network, serving node(s) can be embodied in serving GPRS support node(s) (SGSN).

As indicated above, server(s) 3714 in macro network platform 3710 can execute numerous applications (e.g., location services, online gaming, wireless banking, wireless device management . . . ) that generate multiple disparate packetized data streams or flows, and manage (e.g., schedule, queue, format . . . ) such flows. Such application(s), for example can include add-on features to standard services provided by macro network platform 3710. Data streams can be conveyed to gateway node(s) 3718 for authorization/ authentication and initiation of a data session, and to serving node(s) 3716 for communication thereafter. Server(s) 3714 can also effect security (e.g., implement one or more firewalls) of macro network platform 3710 to ensure network's operation and data integrity in addition to authorization and authentication procedures that CS gateway node(s) 3712 and gateway node(s) 3718 can enact. Moreover, server(s) 3714 can provision services from external network(s), e.g., WAN 3750, or Global Positioning System (GPS) network(s) (not shown). It is to be noted that server(s) 3714 can include one or more processor configured to confer at least in part the functionality of macro network platform 3710. To that end, the one or more processor can execute code instructions stored in memory 3730, for example.

In example wireless environment 3700, memory 3730 stores information related to operation of macro network platform 3710. Information can include business data associated with subscribers; market plans and strategies, e.g., promotional campaigns, business partnerships; operational data for mobile devices served through macro network platform; service and privacy policies; end-user service logs for law enforcement; and so forth. Memory 3730 can also store information from at least one of telephony network(s) 3740, WAN(s) 3750, or SS7 network 3760, enterprise NW(s) 3765, or service NW(s) 3767.

Femto gateway node(s) 3784 have substantially the same functionality as PS gateway node(s) 3718. Additionally, femto gateway node(s) 3784 can also include substantially all functionality of serving node(s) 3716. In an aspect, femto gateway node(s) 3784 facilitates handover resolution, e.g., assessment and execution. Further, control node(s) 3720 can receive handover requests and relay them to a handover component (not shown) via gateway node(s) 3784. According to an aspect, control node(s) 3720 can support RNC capabilities and can be substantially similar to the control component 320 (FIG. 3) and can include functionality thereof.

Server(s) 3782 have substantially the same functionality as described in connection with server(s) 3714. In an aspect, server(s) 3782 can execute multiple application(s) that provide service (e.g., voice and data) to wireless devices served through femto RAN 3790. Server(s) 3782 can also provide security features to femto network platform. In addition, server(s) 3782 can manage (e.g., schedule, queue, format . . . ) substantially all packetized flows (e.g., IP-based, frame relay-based, ATM-based) it generates in addition to data received from macro network platform 3710. It is to be noted that server(s) 3782 can include one or more processor configured to confer at least in part the functionality of macro network platform 3710. To that end, the one or more processor can execute code instructions stored in memory 3786, for example.

Memory 3786 can include information relevant to operation of the various components of femto network platform 3780. For example operational information that can be stored in memory 3786 can comprise, but is not limited to, subscriber information; contracted services; maintenance and service records; femto cell configuration (e.g., devices served through femto RAN 3790; access control lists, or white lists); service policies and specifications; privacy policies; add-on features; and so forth.

It is noted that femto network platform 3780 and macro network platform 3710 can be functionally connected through one or more reference link(s) or reference interface(s). In addition, femto network platform 3780 can be functionally coupled directly (not illustrated) to one or more of external network(s) 3740, 3750, 3760, 3765 or 3767. Reference link(s) or interface(s) can functionally link at least one of gateway node(s) 3784 or server(s) 3786 to the one or more external networks 3740, 3750, 3760, 3765 or 3767.

Figure 38:
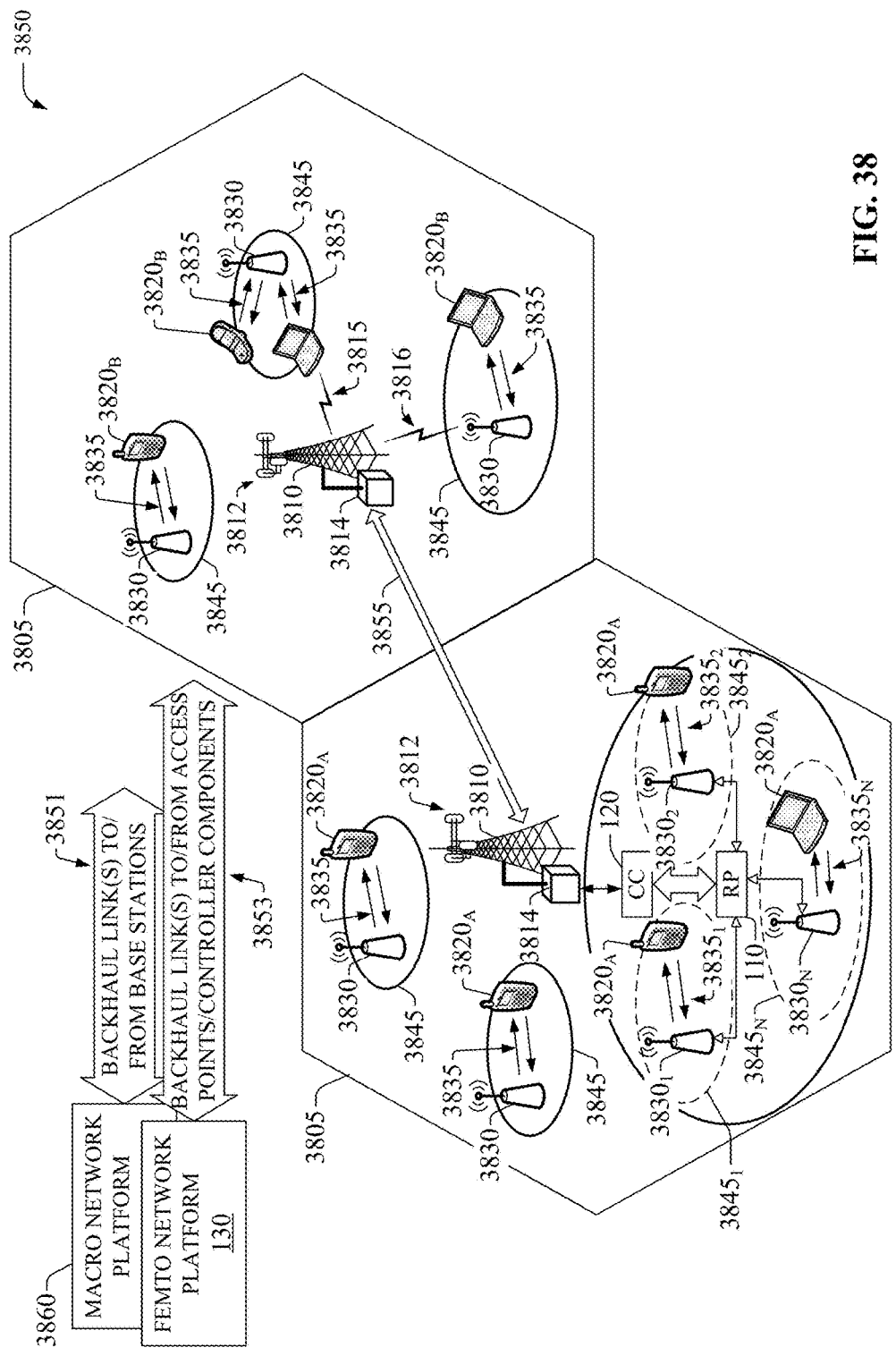
FIG. 38 illustrates a schematic deployment of a macro cell and a femto cell for wireless coverage in accordance with aspects of the subject specification.

FIG. 38 illustrates a wireless environment that includes macro cells and femtocells for wireless coverage in accordance with aspects described herein. In wireless environment 3850, two areas 3805 represent "macro" cell coverage, each macro cell is served by a base station 3810. It can be appreciated that macro cell coverage area 3805 and base station 3810 can include functionality, as more fully described herein, for example, with regard to system 3800. Macro coverage is generally intended to serve mobile wireless devices, like UE $3820_A$, $3820_B$, in outdoors locations. An over-the-air wireless link 115 provides such coverage, the wireless link 1215 comprises a downlink (DL) and an uplink (UL), and utilizes a predetermined band, licensed or unlicensed, of the radio frequency (RF) spectrum. As an example, UE $3820_A$, $3820_E$ can be a 3GPP Universal Mobile Telecommunication System (UMTS) mobile phone. It is noted that a set of base stations, its associated electronics, circuitry or components, base stations control component(s), and wireless links operated in accordance to respective base stations in the set of base stations form a radio access network (RAN). In addition, base station 3810 communicates via backhaul link(s) 3851 with a macro network platform 3860, which in cellular wireless technologies (e.g., 3rd Generation Partnership Project (3GPP) Universal Mobile Telecommunication System (UMTS), Global System for Mobile Communication (GSM)) represents a core network.

In an aspect, macro network platform 3860 controls a set of base stations 3810 that serve either respective cells or a number of sectors within such cells. Base station 3810 comprises radio equipment 3814 for operation in one or more radio technologies, and a set of antennas 3812 (e.g., smart antennas, microwave antennas, satellite dish(es) . . . ) that can serve one or more sectors within a macro cell 3805. It is noted that a set of radio network control node(s), which can be a part of macro network platform; a set of base stations (e.g., Node B 3810) that serve a set of macro cells 3805; electronics, circuitry or components associated with the base stations in the set of base stations; a set of respective OTA wireless links (e.g., links 3815 or 3816) operated in accordance to a radio technology through the base stations; and backhaul link(s) 3855 and 3851 form a macro radio access network (RAN). Macro network platform 3860 also communicates with other base stations (not shown) that serve other cells (not shown). Backhaul link(s) 3851 or 3853 can include a wired backbone link (e.g., optical fiber backbone, twisted-pair line, T1/E1 phone line, a digital subscriber line (DSL) either synchronous or asynchronous, an asymmetric ADSL, or a coaxial cable . . . ) or a wireless (e.g., line-of-sight (LOS) or non-LOS) backbone link. Backhaul pipe(s) 3855 link disparate base stations 3810. According to an aspect, backhaul link 3853 can connect multiple femto access points 3830 and/or controller components (CC) 120 to the femto network platform 130. In one example, multiple femto APs can be connected to a routing platform (RP) 110, which in turn can be connect to a controller component (CC) 120. Typically, the information from UEs $3820_A$ can be routed by the RP 102, for example, internally, to another UE $3820_A$ connected to a disparate femto AP connected to the RP 110, or, externally, to the femto network platform 130 via the CC 120, as discussed in detail supra.

In wireless environment 3850, within one or more macro cell(s) 3805, a set of femtocells 3845 served by respective femto access points (APs) 3830 can be deployed. It can be appreciated that, aspects of the subject application are geared to femtocell deployments with substantive femto AP density, e.g., $10^4$-$10^7$ femto APs 3830 per base station 3810. According to an aspect, a set of femto access points $3830_1$-$3730_N$, with N a natural number, can be functionally connected to a routing platform 110, which can be functionally coupled to a controller component 120. The controller component 120 can be operationally linked to the femto network platform 330 by employing backhaul link(s) 3853. Accordingly, UEs UE $3720_A$ connected to femto APs $3830_1$-$3830_N$ can communicate internally within the femto enterprise via the routing platform (RP) 110 and/or can also communicate with the femto network platform 130 via the RP 110, controller component 120 and the backhaul link(s) 3853. It can be appreciated that although only one femto enterprise is depicted in FIG. 38, multiple femto enterprise networks can be deployed within a macro cell 3805.

It is noted that while various aspects, features, or advantages described herein have been illustrated through femto access point(s) and associated femto coverage, such aspects and features also can be exploited for home access point(s) (HAPs) that provide wireless coverage through substantially any, or any, disparate telecommunication technologies, such as for example Wi-Fi (wireless fidelity) or picocell telecommunication. Additionally, aspects, features, or advantages of the subject application can be exploited in substantially any wireless telecommunication, or radio, technology; for example, Wi-Fi, Worldwide Interoperability for Microwave Access (WiMAX), Enhanced General Packet Radio Service (Enhanced GPRS), 3GPP LTE, 3GPP2 UMB, 3GPP UMTS, HSPA, HSDPA, HSUPA, or LTE Advanced. Moreover, substantially all aspects of the subject application can include legacy telecommunication technologies.

Various aspects or features described herein can be implemented as a method, apparatus, or article of manufacture using standard programming and/or engineering techniques. In addition, various aspects disclosed in the subject specification can also be implemented through program modules stored in a memory and executed by a processor, or other combination of hardware and software, or hardware and firmware. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disc (CD), digital versatile disc (DVD), blu-ray disc (BD) . . . ), smart cards, and flash memory devices (e.g., card, stick, key drive . . . ). Additionally, it should be appreciated that a carrier wave can be employed to carry computer-readable electronic data such as those used in transmitting and receiving electronic mail or in accessing a network such as the internet or a local area network (LAN). Of course, those skilled in the art will recognize many modifications may be made to this configuration without departing from the scope or spirit of the claimed subject matter.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor also can be implemented as a combination of computing processing units.

In the subject specification, terms such as "store," "data store," "data storage," "database," "repository," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory. In addition, memory components or memory elements can be removable or stationary. Moreover, memory can be internal or external to a device or component, or removable or stationary. Memory can include various types of media that are readable by a computer, such as hard-disc drives, zip drives, magnetic cassettes, flash memory cards or other types of memory cards, cartridges, or the like.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory What has been described above includes examples of systems and methods that provide advantages of the subject application. It is, of course, not possible to describe every conceivable combination of components or methodologies for purposes of describing the subject application, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A method, comprising:
   determining, by a routing device of an enterprise femto network that comprises a processor, that a mobile device is coupled to a femto access point device of femto access point devices that are deployed in the enterprise femto network, wherein the femto access point devices are coupled to a network gateway device of a cellular network via a common backhaul link;
   subsequent to the determining, receiving, by the routing device, status data indicative of an operational status of an intra-premises device of an intra-premises network that is coupled to the enterprise femto network and deployed within a coverage area of the femto access point devices, wherein the receiving comprises receiving the status data independently of utilizing the network gateway device; and facilitating, by the routing device, a transmission of the status data to the mobile device via the femto access point device and independently of utilizing the network gateway device, wherein a route for the transmission between the routing device and the mobile device is determined based on preference data indicative of a routing preference, and wherein the preference data is determined to be linked to a user identity of the mobile device.

2. The method of claim 1, further comprising:
based on analyzing information stored within an access control data structure associated with the femto access point device, verifying, by the routing device, that the mobile device is authorized to receive the status data.

3. The method of claim 1, wherein the receiving comprises receiving the status data in accordance with profile data associated with the mobile device.

4. The method of claim 3, further comprising:
receiving, by the routing device, configuration data that facilitates a configuration the profile data.

5. The method of claim 4, wherein the receiving the configuration data comprises receiving the configuration data from the mobile device.

6. The method of claim 4, wherein the receiving the configuration data comprises receiving the configuration data from a network device.

7. The method of claim 1, wherein the intra-premises device is a security device and the receiving comprises receiving alarm data determined by the security device.

8. The method of claim 1, wherein the receiving comprises receiving status data indicating that the intra-premises device has been switched on.

9. The method of claim 1, wherein the receiving comprises receiving status data indicating that the intra-premises device has been switched off.

10. The method of claim 1, further comprising:
selecting, by the routing device, the intra-premises device based on experience data associated with subscriber account information linked to the mobile device.

11. The method of claim 1, wherein the intra-premises device is a heating, ventilating, and air conditioning equipment and wherein the receiving the status data comprises receiving an operating status of the heating, ventilating, and air conditioning equipment.

12. A routing device, comprising:
a processor; and
a memory that stores executable instructions that, when executed by the processor, facilitate performance of operations, comprising:
subsequent to a determination that a communication device is coupled to a femto access point device of femto access point devices deployed in an enterprise femto network, receiving status data indicative of an operational status of an intra-premises device of an intra-premises network that is coupled to the enterprise femto network and deployed within a coverage area of the femto access point devices, wherein the routing device couples the femto access point devices to a network gateway device of a cellular network via a common backhaul link and couples the femto access point devices to the intra-premises device, and wherein the receiving comprises receiving the status data independent of utilizing the network gateway device, and facilitating a transmission comprising the status data from the routing device to the communication device via a route that is independent of utilization of the network gateway device, wherein the route for the transmission is selected based on preference data indicative of a routing preference associated with a user identity of the communication device.

13. The routing device of claim 12, wherein the operational status indicates that the intra-premises device is turned on.

14. The routing device of claim 12, wherein the operational status indicates that the intra-premises device is turned off.

15. The routing device of claim 12, wherein the intra-premises device is a security device and the status data comprises alarm data determined by the security device.

16. The routing device of claim 12, wherein the intra-premises device is a heating, ventilating, and air conditioning equipment and the status data comprises an operating status of the heating, ventilating, and air conditioning equipment.

17. The routing device of claim 12, wherein the intra-premises device is a medical device and the status data comprises vitals data captured via the medical device.

18. A non-transitory machine-readable storage medium comprising executable instructions that, when executed by a processor of a routing device of an enterprise femto network facilitate performance of operations, comprising:
after determining that a communication device is coupled to a femto access point device of femto access point devices deployed in the enterprise femto network, receiving status data from an intra-premises device of an intra-premises network that is coupled to the enterprise femto network and deployed within a coverage area of the femto access point devices, wherein the routing device couples the femto access point devices to a network gateway device of a cellular network via a common backhaul link and couples the femto access point devices to the intra-premises device, and wherein the status data is indicative of an operational status of the intra-premises device; and directing, from the routing device to the communication device, the status data via a route that is independent of transferring the status data via the network gateway device, wherein the route is determined based on preference data indicative of a routing preference defined by a user identity related to the communication device.

19. The non-transitory machine-readable storage medium of claim 18, wherein the intra-premises device is a security device and the status data comprises alarm data determined by the security device.

20. The non-transitory machine-readable storage medium of claim 18, wherein the operations further comprise:
selecting the intra-premises device based on experience data associated with subscriber account information linked to the user identity.

* * * * *